United States Patent
Schoeler et al.

(10) Patent No.: US 10,711,244 B2
(45) Date of Patent: Jul. 14, 2020

(54) MAMMALIAN NEURAL PLATE BORDER STEM CELLS CAPABLE OF FORMING NEURAL TUBE AND NEURAL CREST CELL LINEAGES INCLUDING CENTRAL AND PERIPHERAL NEURONS

(71) Applicant: Max-Planck-Gesellschaft zur Förderung der Wissenschaften E.V., Munich (DE)

(72) Inventors: Hans R. Schoeler, Muenster (DE); Jared L. Sterneckert, Muenster (DE); Michael Glatza, Hamma (DE); Peter Reinhardt, Muenster (DE)

(73) Assignee: MAX-PLANCK-GESELLSCHAFT ZUR FÖRDERUNG DER WISSENSCHAFTEN E.V., München (DE)

( * ) Notice: Subject to any disclaimer, the term of this patent is extended or adjusted under 35 U.S.C. 154(b) by 0 days.

(21) Appl. No.: 15/233,561

(22) Filed: Aug. 10, 2016

(65) Prior Publication Data
US 2017/0037367 A1 Feb. 9, 2017

Related U.S. Application Data

(63) Continuation of application No. 14/371,701, filed as application No. PCT/EP2013/050482 on Jan. 11, 2013, now abandoned.

(30) Foreign Application Priority Data

Jan. 11, 2012 (EP) .................................... 12000143

(51) Int. Cl.
*C12N 5/0797* (2010.01)
*C12N 5/0793* (2010.01)
(Continued)

(52) U.S. Cl.
CPC ............ *C12N 5/0623* (2013.01); *A61K 35/30* (2013.01); *C12N 5/062* (2013.01); *C12N 5/0619* (2013.01); *C12N 5/0622* (2013.01); *C12N 5/0647* (2013.01); *C12N 2500/38* (2013.01); *C12N 2501/01* (2013.01); *C12N 2501/119* (2013.01); *C12N 2501/13* (2013.01); *C12N 2501/148* (2013.01); *C12N 2501/15* (2013.01); *C12N 2501/155* (2013.01); *C12N 2501/16* (2013.01);
(Continued)

(58) Field of Classification Search
CPC .............. C12N 5/0623; C12N 2506/02; C12N 2501/148; C12N 2506/45; C12N 2501/119; C12N 2501/01; C12N 2501/13; C12N 2501/15; C12N 2501/41; C12N 2501/415; C12N 2501/155; C12N 2501/16; C12N 2501/385; A61K 35/30
See application file for complete search history.

(56) References Cited

U.S. PATENT DOCUMENTS

2015/0010515 A1* 1/2015 Schoeler ................ A61K 35/30
424/93.7

FOREIGN PATENT DOCUMENTS

WO 2004087879 A2 10/2004

OTHER PUBLICATIONS

Li et al., PNAS, 108(20):8299-8304; May 7, 2011. (Year: 2011).*
Li et al., PNAS, 108(20):8299-8304, May (Year: 2011).*
Gee et al., "Yes-Assocaited Protein 65 (YAP) Expands Neural Progenitors and Regulates PAX3 Expression in the Neural Plate Border Zone", PLoS ONE, vol. 6 (6), (2011), pp. 1-15.
Hernandez-Lagunas et al., "prdm1a and olig 4 Act Downstream of Notch Signaling to Regulate Cell Fate at the Neural Plate Border", Developmental Biology, vol. 356, (2011) pp. 496-505.
(Continued)

*Primary Examiner* — Kimberly Ballard
*Assistant Examiner* — Stacey N MacFarlane
(74) *Attorney, Agent, or Firm* — Roberts Calderon Safran & Cole P.C.

(57) ABSTRACT

The present invention relates to a method for producing mammalian neural plate border stem cells (NPBSCs), comprising: (a) differentiation of mammalian pluripotent stem cells by (a-i) culturing mammalian pluripotent stem cells in pluripotent stem cell medium for about 24 to about 96 hours, wherein the pluripotent stem cell medium comprises: (i) an inhibitor of the activin/TGF-β signalling pathway; (ii) an inhibitor of the BMP signalling pathway; (iii) an activator of the canonical WNT signalling pathway; and (iv) an activator of the Hedgehog signalling pathway; subsequently (a-ii) culturing the cells obtained in step (a-i) for about 24 to about 96 hours in a neural medium, wherein the neural medium comprises: (i) an inhibitor of the Activin/TGF-β signalling pathway; (ii) an inhibitor of the BMP signalling pathway; (iii) an activator of the canonical WNT signalling pathway; and (iv) an activator of the Hedgehog signalling pathway; subsequently (a-iii) culturing the cells obtained in step (a-ii) for about 24 to about 96 hours in a neural medium, wherein the neural medium comprises: (i) an activator of the canonical WNT signalling pathway; (ii) an activator of the Hedgehog signalling pathway; and (iii) an inhibitor of oxidation; and (b) plating the obtained differentiated mammalian pluripotent stem cells in NPBSCs expansion medium, wherein the NPBSCs expansion medium comprises (i) an activator of the canonical WNT signalling pathway; (ii) an activator of the Hedgehog signalling pathway; and (iii) an inhibitor of oxidation; and expanding the cells in the NPBSCs expansion medium for about 24 to about 96 hours; (c) splitting the cells obtained in (b) and further expanding the cells in the NPBSCs expansion medium; and (d) repeating step (c) at least two times. The present invention further relates to neural plate border stem cells obtainable by the method of the invention and the use of the cells of the invention in medicine.

12 Claims, 33 Drawing Sheets

Figure 1:
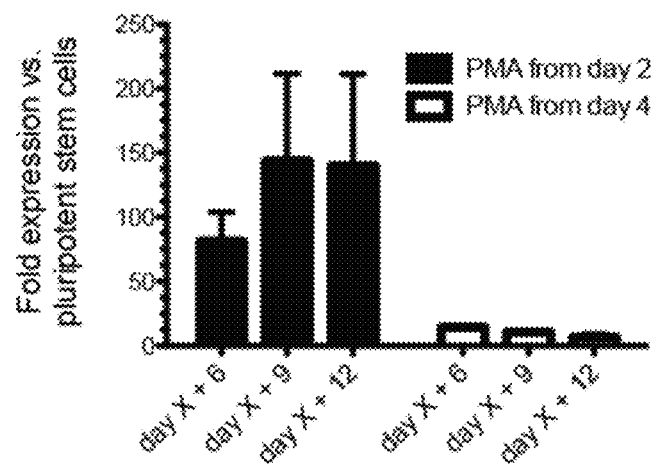
Figure 1:
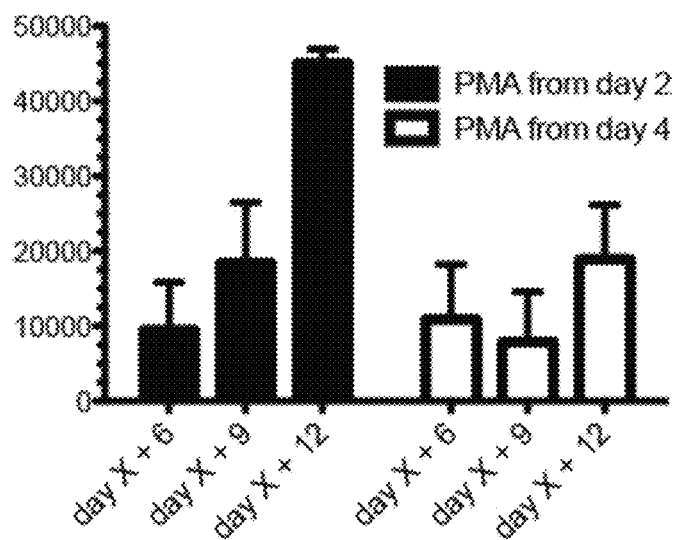

(51) Int. Cl.
  C12N 5/079   (2010.01)
  C12N 5/0789  (2010.01)
  A61K 35/30   (2015.01)
(52) U.S. Cl.
  CPC .... C12N 2501/385 (2013.01); C12N 2501/41 (2013.01); C12N 2501/415 (2013.01); C12N 2501/70 (2013.01); C12N 2501/999 (2013.01); C12N 2506/02 (2013.01); C12N 2506/45 (2013.01); C12N 2533/90 (2013.01)

(56) References Cited

OTHER PUBLICATIONS

Law et al., "prdm1a Regulates Rohon-Beard Neuron and Neural Crest Cell Fate at the Neural Plate Border", Developmental Biology, (2010) p. 500.
Ezin et al., "Fate Map and Morphogenesis of Presumptive Neural Crest and Dorsal Neural Tube", Developmental Biology, vol. 330, (2009) pp. 221-236.
Patthey et al., "Wnt-Regulated Temporal Control of BMP Exposure Directs the Choice Between Neural Plate Border and Epidermal Fate", Development, vol. 136 (1), (2009) pp. 73-83.
Alvarez-Medina et al., "Hedgehog Activation is Required Upstream of Wnt Signalling to Control Neural Progenitor Proliferation", Development, vol. 136 (19), (2009) pp. 3301-3309.
International Search Report of International Application No. PCT/EP2013050482 dated Apr. 29, 2013.
Bai et al., "Gli2, But Not Gli1, is Required for Initial Shh Signaling and Ectopic Activation of the Shh Pathway", Development, vol. 129, (2002) pp. 4753-4761.
Chambers et al., "Highly Efficient Neural Conversion of Human ES and iPS Cells by Dual Inhibition of SMAD Signaling", Nature Biotechnology, vol. 27 (3), (2009) pp. 275-280.
Coyne et al., "Neuropharmacological Properties of Neurons Derived From Human Stem Cells", Neurochemistry International, vol. 59, (2011) pp. 404-412.
Cummins et al., "Functional Properties of Rat and Human Neocortical Voltage-Sensitive Sodium Currents", Journal of Neurophysiology, vol. 71 (3), (1994) pp. 1052-1064.
Del Castillo et al., "Quantal Components of the End-Plate Potential", Journal of Physiology, vol. 124, (1954) pp. 560-573.
Edwards et al., "Quantal Analysis of Inhibitory Synaptic Transmission in the Dentate Gyrus of Rat Hippocampal Slices: A Patch-Clamp Study", Journal of Physiology, vol. 430, (1990) pp. 213-249.
Elkabetz et al., "Human ES Cell-Derived Neural Rosettes Reveal a Functionally Distinct Early Neural Stem Cell Stage", Genes Dev, vol. 22, (2008) pp. 152-165.
Goulding et al., "Pax-3, a Novel Murine DNA Binding Protein Expressed During Early Neurogenesis", The EMBO Journal, vol. 10 (5), (1991) pp. 1135-1147.
Fasano et al., "Efficient Derivation of Functional Floor Plate Tissue From Human Embryonic Stem Cells", Cell Stem Cell, vol. 6, (2010), pp. 336-347.
Gale et al., "Midbrain Dopaminergic Neuron Fate Specification: Of Mice and Embryonic Stem Cells", Molecular Brain, vol. 1, (2008) pp. 1-10.
Hamill et al., "Improved Patch-Clamp Techniques for High-Resolution Current Recording From Cells and Cell-Free Membrane Patches", Pflugers Arch, vol. 391, (1981) pp. 85-100.
Inenaga et al., "Glutamatergic Synaptic Inputs to Mouse Supraoptic neurons in Calcium-Free medium in Vitro", Journal of Neuroendocrinology, vol. 10, (1998) pp. 1-7.
Jessell, "Neuronal Specification in the Spinal Cord: Inductive Signals and Transcriptional Codes", Nature Reviews, Genetics, vol. 1, (2000) pp. 20-29.
Kiecker et al., "A Morphogen Gradient of Wnt/β-Catenin Signalling Regulates Anteroposterior Neural Patterning in Xenopus", Development, vol. 128, (2001) pp. 4189-4201.
Koch et al., "A Rosette-Type, Self-Renewing Human ES Cell-Derived Neural Stem Cell With Potential for in Vitro Instruction and Synaptic Integration", PNAS, vol. 106 (9), (2009) pp. 3225-3230.
Lee et al., "The Specification of Dorsal Cell Fates in the Vertebrate Central Nervous System", Annual Reviews of Neuroscience, vol. 22 (1999) pp. 261-294.
Li et al., "Rapid Induction and Long-Term Self-Renewal of Primitive Neural Precursors From Human Embryonic Stem Cells by Small Molecule Inhibitors", PNAS, vol. 108 (20), (2011) pp. 8299-8304.
Moe et al., "Multipotent Progenitor Cells From the Adult Human Brain: Neurophysiological Differentiation to Mature Neurons", Brain, vol. 128, (2005) pp. 2189-2199.
Nordstrom et al., "Progressive Induction of Caudal Neural Character by Graded Wnt Signaling", Nature Neuroscience, vol. 5 (6), (2002) pp. 525-532.
Novitch et al., "A Requirement for Retinoic Acid-Mediated Transcriptional Activation in Ventral Neural Patterning and Motor Neuron Specification", Neuron, vol. 40, (2003) pp. 81-95.
Patthey et al., "Early Deceloptment of the Central and Peripheral Nervous Systems is Coordinated by Wnt and BMP Signals", PLoS One, vol. 3 No. 2, (2008) pp. 1-10.
Selleck et al., "Effects of Shh and Noggin on Neural Crest Formation Demonstrate that BMP is Required in the Neural Tube but not Ectoderm", Development, vol. 125, (1998) pp. 4919-4930.
Simard et al., "Ionic Channel Currents in Cultured Neurons From Human Cortex", Journal of Neuroscience Research, vol. 34, (1993) pp. 170-178.
Tribulo et al., "Regulation of Msx Genes by a Bmp Gradient is Essential for Neural Crest Specification", Development, vol. 130 No. 26, (2003) pp. 6441-6452.
Ulloa et al., "Morphogens and the Control of Cell Proliferation and Patterning in the Spinal Cord", Cell Cycle, vol. 6 (21), (2007), pp. 2640-2649.
Westerlund et al., "Stem Cells From the Adult Human Brain Develop Into Functional Neurons in Culture", Experimental Cell Research, vol. 289, (2003) pp. 378-383.
Wichterle et al., "Directed Differentiation of Embryonic Stem Cells into Motor Neurons", Cell, vol. 110, (2002) pp. 385-397.
Wyllie et al., "A Rise in Postsynaptic Ca2+ Potentiates Miniature Excitatory Postsynaptic Currents and AMPA Responses in Hippocampal Neurons", Neuron, vol. 12, (1994) pp. 127-138.
Zhang et al., "In Vitro Differentiation of Transplantable Neural Precursors From Human Embryonic Stem Cells", NatureBiotechnology, vol. 19, (2001) pp. 1129-1133.
Krencik et al., "Specification of Transplantable Astroglial Subtypes from Human Pluripotent Stem Cells", Nature Biotechnology, vol. 29 No. 6, (2011) pp. 528-535.
Chambers et al, Nature Biotechnology, 27(3):275-280, Mar. 2009.
Dupin et al, CR Biologies, 333:521-529, May 2007.
Lee et al., Nature Biotechnology, 25(12):1468-1475, Dec. 2007.
Stemple et al., Cell;71 (6):973-85; Dec. 11, 1992.
Bronner, Histochem Cell Biol;138(2):179-86, Epub Jul. 22, 2012.
Anselme L. Perrier et al. Derivation of midbrain dopamine neurons from human embryonic stem cells; PNAS Aug. 24, 2004, vol. 101 No. 34 pp. 12543-12548.

* cited by examiner

MAMMALIAN NEURAL PLATE BORDER STEM CELLS CAPABLE OF FORMING NEURAL TUBE AND NEURAL CREST CELL LINEAGES INCLUDING CENTRAL AND PERIPHERAL NEURONS

RELATED APPLICATIONS

The present application is a Continuation Application under 35 USC § 120 of U.S. application Ser. No. 14/371,701, filed Jul. 10, 2014, which in turn is the US National Stage application of PCT Application No. PCT/EP2013/050482, filed Jan. 11, 2013. These prior applications are hereby incorporated in their entirety by reference.

DESCRIPTION

The present invention relates to a method for producing mammalian neural plate border stem cells (NPBSCs), comprising: (a) differentiation of mammalian pluripotent stem cells by (a-i) culturing mammalian pluripotent stem cells in pluripotent stem cell medium for about 24 to about 96 hours, wherein the pluripotent stem cell medium comprises: (i) an inhibitor of the activin/TGF-β signalling pathway; (ii) an inhibitor of the BMP signalling pathway; (iii) an activator of the canonical WNT signalling pathway; and (iv) an activator of the Hedgehog signalling pathway; subsequently (a-ii) culturing the cells obtained in step (a-i) for about 24 to about 96 hours in a neural medium, wherein the neural medium comprises: (i) an inhibitor of the Activin/TGF-β signalling pathway; (ii) an inhibitor of the BMP signalling pathway; (iii) an activator of the canonical WNT signalling pathway; and (iv) an activator of the Hedgehog signalling pathway; subsequently (a-iii) culturing the cells obtained in step (a-ii) for about 24 to about 96 hours in a neural medium, wherein the neural medium comprises: (i) an activator of the canonical WNT signalling pathway; (ii) an activator of the Hedgehog signalling pathway; and (iii) an inhibitor of oxidation; and (b) plating the obtained differentiated mammalian pluripotent stem cells in NPBSCs expansion medium, wherein the NPBSCs expansion medium comprises (i) an activator of the canonical WNT signalling pathway; (ii) an activator of the Hedgehog signalling pathway; and (iii) an inhibitor of oxidation; and expanding the cells in the NPBSCs expansion medium for about 24 to about 96 hours; (c) splitting the cells obtained in (b) and further expanding the cells in the NPBSCs expansion medium; and (d) repeating step (c) at least two times. The present invention further relates to neural plate border stem cells obtainable by the method of the invention and the use of the cells of the invention in medicine.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The neural tube and neural crest cell lineages are specified during gastrulation from the neural plate through a combination of WNT and bone morphogenetic protein (BMP) signals. WNT signals specify caudal identity, and BMPs direct differentiation into the neural plate border fate, which will go on to form neural crest cell derivatives including peripheral nervous system (PNS) and mesenchymal cells. Sonic hedgehog (SHH) signaling antagonizes the specification of neural crest cells by BMPs and WNT by inducing ventral neural tube progenitors.

Sensory information is conveyed through neurons of the peripheral nervous system (PNS) to the central nervous system (CNS), which processes it and responds with output signals through motor neurons. These two systems, PNS and CNS, are specified during gastrulation from the neural plate. The neural plate is a thickening of medial ectoderm and marks the onset of neurulation. The border region of the neural plate will form neural crest cells, but the medial neural plate will invaginate and form the neural tube, which will differentiate into the central nervous system (CNS).

The caudal neural plate border is specified during gastrulation by a combination of bone morphogenetic protein (BMP) and WNT signals (Patthey et al., 2009; Patthey et al., 2008). During gastrulation, WNT signals form a morphogenic gradient with WNT proteins expressed in the caudal portion of an embryo and inhibitors of WNT signals being produced rostrally (Kiecker and Niehrs, 2001; Nordstrom et al., 2002). This graded WNT signal induces caudal character in the neural plate in a dose dependent manner (Kiecker and Niehrs, 2001; Nordstrom et al., 2002). In addition, exogenous WNT signals induce anterior neural plate cells to differentiate into caudal neural plate border cells, which will form the neural crest (Patthey et al., 2008). In contrast, inhibition of early WNT signals prevents neural plate border specification and results in CNS specification (Patthey et al., 2009).

BMP signaling also plays an important role in neural plate border specification. Neural border identity is induced when caudal plate cells are exposed to BMP protein (Patthey et al., 2008). In addition, although WNT is sufficient to induce caudal neural border character in anterior cells, inhibition of BMP inhibits the specification by WNT and results in CNS identity (Patthey et al., 2009). Patthey et alia demonstrated that a temporal expression pattern of WNT and BMP is responsible for induction of neural border identity (Patthey et al., 2009). Early WNT signaling specifies caudal identity, whereas BMP signaling instructs neural plate border differentiation (Patthey et al., 2009).

Sonic hedgehog (SHH) forms an morphogenic gradient that opposes both the BMP and WNT gradients during the developing neural tube (Ulloa and Briscoe, 2007). Both BMPs and WNTs induce dorsal neural progenitor identity, which expresses many of the same markers as the neural border region including MSX1 and PAX3 (Lee and Jessell, 1999). SHH protein, expressed by the notochord and floor plate, antagonizes BMP and WNT signals and specifies ventral neural identity (Jessell, 2000). As such, SHH represses the dorsal markers MSX1 and PAX3 and induces ventral markers such as OLIG2, NKX2.2, and FOXA2 (Jessell, 2000; Ulloa and Briscoe, 2007). It has been shown that SHH likewise represses neural crest cell differentiation, which are formed from the neural plate border (Selleck et al., 1998).

Alvarez-Medina et al. 2009 describe the co-ordinated regulation of proliferation mediated by Wnt and Shh activities. The authors found that these two pathways appear to interact to control progression of the G1 phase of the cell cycle. However, the work by Alvarez-Medina and co-workers relates to progenitors that are already committed to the central nervous system (e.g. the neural tube) and, thus, represents a strictly proliferative effect on CNS progenitors. Developmentally earlier precursor cell types with the capacity to differentiate into both neural tube and neural crest cell lineages are not discussed in this publication.

Despite the fact that a lot of effort has been invested into methods to direct the differentiation of pluripotent stem cells into precursor cells of neurons from either the CNS or the PNS, no method exists so far to induce pluripotent stem cells into even earlier precursor cells, i.e. precursor cells that are capable of self-renewal in culture with the ability to differentiate into both CNS and PNS neurons. Accordingly, there is still a need to provide such early precursor cells that provide a useful source of CNS and PNS neurons for example for disease modelling and drug discovery.

This need is addressed by the provision of the embodiments characterized in the claims.

Accordingly, the present invention relates to a method for producing mammalian neural plate border stem cells (NPBSCs), comprising:
(a) differentiation of mammalian pluripotent stem cells by
    (a-i) culturing mammalian pluripotent stem cells in pluripotent stem cell medium for about 24 to about 96 hours, wherein the pluripotent stem cell medium comprises:
        (i) an inhibitor of the activin/TGF-β signalling pathway;
        (ii) an inhibitor of the BMP signalling pathway;
        (iii) an activator of the canonical WNT signalling pathway; and
        (iv) an activator of the Hedgehog signalling pathway; subsequently
    (a-ii) culturing the cells obtained in step (a-i) for about 24 to about 96 hours in a neural medium, wherein the neural medium comprises:
        (i) an inhibitor of the activin/TGF-β signalling pathway;
        (ii) an inhibitor of the BMP signalling pathway;
        (iii) an activator of the canonical WNT signalling pathway; and
        (iv) an activator of the Hedgehog signalling pathway; subsequently
    (a-iii) culturing the cells obtained in step (a-ii) for about 24 to about 96 hours in a neural medium, wherein the neural medium comprises:
        (i) an activator of the canonical WNT signalling pathway;
        (ii) an activator of the Hedgehog signalling pathway; and
        (iii) an inhibitor of oxidation; and
(b) plating the obtained differentiated mammalian pluripotent stem cells in NPBSCs expansion medium, wherein the NPBSCs expansion medium comprises
    (i) an activator of the canonical WNT signalling pathway;
    (ii) an activator of the Hedgehog signalling pathway; and
    (iii) an inhibitor of oxidation; and expanding the cells in the NPBSCs expansion medium for about 24 to about 96 hours;
(c) splitting the cells obtained in (b) and further expanding the cells in the NPBSCs expansion medium; and
(d) repeating step (c) at least two times.

In accordance with the present invention, the term "neural plate border stem cells", which are also abbreviated herein as NPBSCs, relates to a novel precursor cell type capable of differentiating into either neural tube or neural crest cell lineages, which form CNS and PNS neurons, respectively. The NPBSCs of the present invention are characterized by the expression of at least three markers selected from the group consisting of MSX1, PHOX2B, PAX3, PAX6, SOX1, SOX2, NESTIN, IRX3, HOXA2, HOXB2, HES5, DACH1, PLZF, LMO3, EVI1 and ASCL1, as defined herein below.

The term "mammalian" is taxonomically well known in the art.

Preferably, the mammalian cells are derived from a mammal selected from the group consisting of e.g. human, mouse, rat, hamster, cow, cat, pig, dog, horse, rabbit or monkey. More preferably, the mammalian NPBSCs are derived from human or mouse, most preferably the mammalian neural plate border stem cells are human neural plate border stem cells.

The term "pluripotent stem cells", in accordance with the present invention, relates to a cell type having the capacity for self-renewal, an ability to go through numerous cycles of cell division while maintaining the undifferentiated state, and the potential of differentiation, i.e. the capacity to differentiate into specialized cell types. Pluripotent stem cells are the descendants of totipotent cells and can differentiate into nearly all cells, i.e. cells derived from any of the three primary germ layers: ectoderm, endoderm, and mesoderm. The term pluripotent stem cells also encompasses stem cells derived from the inner cell mass of an early stage embryo known as a blastocyst. Recent advances in embryonic stem cell research have led to the possibility of creating new embryonic stem cell lines without destroying embryos, for example by using a single-cell biopsy similar to that used in preimplantation genetic diagnosis (PGD), which does not interfere with the embryo's developmental potential (Klimanskaya et al., 2006). Furthermore, a large number of established embryonic stem cell lines are available in the art (according to the U.S. National Institutes of Health, 21 lines are currently available for distribution to researchers), thus making it possible to work with embryonic stem cells without the necessity to destroy an embryo.

In a preferred embodiment, the pluripotent stem cells are not embryonic stem cells obtained via the destruction of a human embryo.

In accordance with the present invention, the pluripotent stem cells can be induced pluripotent stem cells. The term "induced pluripotent stem (iPS) cells", as used herein, refers to pluripotent stem cells derived from a non-pluripotent cell, typically an adult somatic cell, by inducing a "forced" expression of certain genes. Induced pluripotent stem cells are identical to natural pluripotent stem cells, such as e.g. embryonic stem cells, in many respects including, for example, unlimited self-renewal in vitro, a normal karyotype, the expression of certain stem cell genes and proteins such as for example Oct3/4, Sox2, Nanog, alkaline phosphatase (ALP) as well as stem cell-specific antigen 3 and 4 (SSEA3/4), chromatin methylation patterns, doubling time, embryoid body formation, teratoma formation, viable chimera formation, and potency and differentiability (Takahashi and Yamanaka 2006, Cell 126: 663-676; Hanna, J., et al. (2007). Science 318 (5858): 1920-3; Meissner, A., et al. (2007). Nat Biotechnol 25 (10): 1177-81; Nakagawa, M., et al. (2008). Nat Biotechnol 26 (1):101-106; Okita, K., et al. (2007). Nature 448 (7151): 313-7; Takahashi, K., et al. (2007Cell 131 (5): 861-72; Wernig, M., et al. (2007). Nature 448 (7151): 318-24; Yu, J., et al. (2007). Science 318 (5858): 1917-20; Park, I. H., et al. (2008). Nature 451 (7175): 141-6). Induced pluripotent stem cells are an important advancement in stem cell research, as they allow researchers to obtain pluripotent stem cells without the use of embryos (Nishikawa et al., 2008). The induced pluripotent stem cells may be obtained from any adult somatic cell, preferably from fibroblasts, such as for example from skin tissue biopsies. The pluripotency of iPS cells can tested, e.g., by in vitro differentiation into neural, glia and cardiac cells and the production of germline chimaeric animals through blastocyst injection. Human iPS cells lines can be analysed through in vitro differentiation into neural, glia and cardiac cells and their in vivo differentiation capacity can be tested by injection into immuno-deficient SCID mice and the characterisation of resulting tumours as teratomas.

Methods for the generation of human induced pluripotent stem cells are well known to the skilled person. For example, induced pluripotent stem cells can be generated from human skin tissue biopsies (Park and Daley, 2009; Park et al., 2008). Fibroblasts can be grown in MEM-medium containing chemically defined and recombinant serum components. For reprogramming, the human fibroblasts are preferably retrovirally transduced with OCT4, SOX2, c-MYC and NANOG genes. For this, genes are usually cloned into a retroviral vector and transgene-expressing viral particles are produced in the HEK293FT cell line. Human skin fibroblasts can be co-transduced with all four vectors. The obtained iPS cells are preferably cultured according to protocols established for human embryonic stem cells in DMEM-medium containing serum replacement factors and recombinant growth factors. The iPS cells can then be analyzed for normal morphology and normal karyotype and can be studied by fingerprinting analysis and immunostaining for OCT3/4, NANOG, SSEA-3, SSEA-4, Tra-1-60 and Tra-1-81. Gene transcripts for OCT4, SOX2, NANOG, KLF4, c-MYC, REX1, GDF3 and hTERT are analyzed by real-time RT-PCR. Furthermore, multi-lineage differentiation of iPS cells can be confirmed by embryoid body, teratoma formation and differentiation into adult cell types (Choi et al., 2009; Zhang et al., 2009). As another example, human iPS cells can also be obtained from embryonic fibroblasts without viral integration using adenoviral vectors expressing c-Myc, Klf4, Oct4, and Sox2 (Zhou and Freed, 2009). Further methods are described e.g. in WO2009115295, WO2009144008 or EP2218778.

In accordance with the present invention, any medium suitable as a culture medium for pluripotent stem cells may be employed as the "pluripotent stem cell medium". Such media are well established in the art. For example, the pluripotent stem cell medium can be a basal cell culture medium, for example knock-out DMEM comprising: (i) knockout serum replacement; (ii) β-mercaptoethanol; (iii) non-essential amino acids; and (iv) penicillin/streptomycin/glutamine.

DMEM is well known in the art and refers to Dulbecco's Modified Eagle Medium. Knock-out DMEM is a basal medium optimized for growth of undifferentiated embryonic and induced pluripotent stem cells and can be commercially obtained, for example from Invitrogen. Also knockout serum replacement, β-mercaptoethanol and non-essential aminoacids (NEAA) can be commercially obtained, for example from Invitrogen and penicillin, streptomycin and glutamine may for example be commercially obtained from PAA.

The skilled person is aware of suitable amounts of these compounds to be employed in a cell culture medium, such as the pluripotent stem cell medium of the present invention. Preferably, the knockout serum replacement is added in an amount of at least 5%, such as e.g. at least 10%, at least 15% and most preferably at least 20%. Preferably, the β-mercaptoethanol is added in an amount of at least 0.01 mM, such as e.g. at least 0.05 mM, at least 0.07 mM, at least 0.1 mM and most preferably at least 0.11 mM. Mixtures of non-essential amino acids preferably comprise glycine, L-alanine, L-asparagine, L-aspartic acid, L-glutamic acid, L-proline and L-serine at 10 mM and preferably, at least 0.5%, such as e.g. at least 1% of this mixtures is added to the pluripotent stem cell medium. Penicillin, streptomycin and glutamine mixtures typically consist of 200 mM L-glutamine, 10,000 Units/ml Penicillin and 10 mg/ml streptomycin and are preferably added to the pluripotent stem cell medium in an amount of at least 0.5%, more preferably at least 1%.

In a preferred embodiment, the pluripotent stem cell medium is knock-out DMEM comprising 20% knockout serum replacement, 0.11 mM β-mercaptoethanol, 1% non-essential amino acids and 1% of a penicillin, streptomycin and glutamine mixture.

Preferably, the pluripotent stem cell medium is free of FGF2. The term "FGF2" refers to the basic fibroblast growth factor, a member of the fibroblast growth factor family, that is also referred to as bFGF or FGF-β in the art (Kurokawa et al., 1987). The omission of FGF2 is preferred, as this growth factor may slow down the differentiation of the pluripotent stem cells.

In accordance with the present invention, the pluripotent stem cell medium further comprises
(i) an inhibitor of the activin/TGF-β signalling pathway;
(ii) an inhibitor of the BMP signalling pathway;
(iii) an activator of the canonical WNT signalling pathway; and
(iv) an activator of the Hedgehog signalling pathway.

The term "inhibitor", as used herein, refers to a compound that reduces or abolishes the biological function or activity of the recited signalling pathway, by interfering with a specific target protein that is part of this signalling pathway or by interfering with the interaction between two or more target proteins. An inhibitor may perform any one or more of the following effects in order to reduce or abolish the biological function or activity of the protein to be inhibited: (i) the transcription of the gene encoding the protein to be inhibited is lowered, i.e. the level of mRNA is lowered, (ii) the translation of the mRNA encoding the protein to be inhibited is lowered, (iii) the protein performs its biochemical function with lowered efficiency in the presence of the inhibitor, and (iv) the protein performs its cellular function with lowered efficiency in the presence of the inhibitor.

Compounds suitable to achieve the effect described in (i) include compounds interfering with the transcriptional machinery and/or its interaction with the promoter of said gene and/or with expression control elements remote from the promoter such as enhancers. Compounds suitable to achieve the effect described in (ii) comprise antisense constructs and constructs for performing RNA interference (e.g. siRNA, shRNA, miRNA) well known in the art (see, e.g. Zamore (2001) Nat. Struct. Biol. 8 (9), 746; Tuschl (2001) Chembiochem. 2 (4), 239). Compounds suitable to achieve the effect described in (iii) interfere with molecular functions of the protein to be inhibited. Compounds suitable to achieve the effect described in (iv) include compounds which do not necessarily bind directly to the target protein, but still interfere with their activity, for example by binding to and/or inhibiting the function or expression of members of a pathway which comprises the target protein. These members may be either upstream or downstream of the protein to be inhibited within said pathway.

Such compounds further include, without being limiting, small molecules, antibodies, aptamers and ribozymes. Suitable compounds further include but are not limited to, peptides such as soluble peptides, including Ig-tailed fusion peptides and members of random peptide libraries (see, e.g., Lam et al. (1991) Nature 354: 82-84; Houghten et al. (1991) Nature 354: 84-86) and combinatorial chemistry-derived molecular libraries made of D- and/or L-configuration amino acids or phosphopeptides (e.g., members of random and partially degenerate, directed phosphopeptide libraries, see, e.g., Songyang et al. (1993) Cell 72: 767-778).

A "small molecule" according to the present invention may be, for example, an organic molecule. Organic molecules relate or belong to the class of chemical compounds having a carbon basis, the carbon atoms linked together by carbon-carbon bonds. The original definition of the term organic related to the source of chemical compounds, with organic compounds being those carbon-containing compounds obtained from plant or animal or microbial sources, whereas inorganic compounds were obtained from mineral sources.

Organic compounds can be natural or synthetic. Alternatively, the "small molecule" in accordance with the present invention may be an inorganic compound. Inorganic compounds are derived from mineral sources and include all compounds without carbon atoms (except carbon dioxide, carbon monoxide and carbonates). Preferably, the small molecule has a molecular weight of less than about 2000 amu, or less than about 1000 amu such as less than about 500 amu, and even more preferably less than about 250 amu. The size of a small molecule can be determined by methods well-known in the art, e.g., mass spectrometry. The small molecules may be designed, for example, based on the crystal structure of the target molecule, where sites presumably responsible for the biological activity, can be identified and verified in in vivo assays such as in vivo high-throughput screening (HTS) assays. Such small molecules may be particularly suitable to inhibit protein-protein-interaction by blocking specific bindings sites of the target molecule. Suitable small molecules currently employed in the inhibition of the recited signalling pathways include, without being limiting: 4-[4-(3,4-Methylenedioxyphenyl)-5-(2-pyridyl)-1H-imidazol-2-yl]-benzamide hydrate (SB431542) for the inhibition of the activin/TGF-β signalling pathway; 6-[4-[2-(1-Piperidinyl)ethoxy]phenyl]-3-(4-pyridinyl)-pyrazolo[1,5-a]pyrimidine dihydrochloride (dorsomorphin) for the inhibition of the BMP signalling pathway, and (5R)-[(1S)-1,2-dihydroxyethyl]-3,4-dihydroxyfuran-2(5H-one (ascorbic acid) for the inhibition of oxidation.

The term "antisense nucleic acid molecule" is known in the art and refers to a nucleic acid which is complementary to a target nucleic acid, i.e. a nucleic acid encoding the target protein. An antisense molecule in accordance with the invention is capable of interacting with the target nucleic acid, more specifically it is capable of hybridising with the target nucleic acid. Due to the formation of the hybrid, transcription of the target gene(s) and/or translation of the target mRNA is reduced or blocked. Standard methods relating to antisense technology have been described (see, e.g., Melani et al., Cancer Res. (1991) 51:2897-2901).

In accordance with the present invention, the term "small interfering RNA (siRNA)", also known as short interfering RNA or silencing RNA, refers to a class of 18 to 30, preferably 19 to 25, most preferred 21 to 23 or even more preferably 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome. siRNAs naturally found in nature have a well defined structure: a short double-strand of RNA (dsRNA) with 2-nt 3' overhangs on either end. Each strand has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Essentially any gene of which the sequence is known can thus be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Exogenously introduced siRNAs may be devoid of overhangs at their 3' and 5' ends, however, it is preferred that at least one RNA strand has a 5'- and/or 3'-overhang. Preferably, one end of the double-strand has a 3'-overhang from 1-5 nucleotides, more preferably from 1-3 nucleotides and most preferably 2 nucleotides. The other end may be blunt-ended or has up to 6 nucleotides 3'-overhang. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3' overhangs on either end. The sequence of the 2-nt 3' overhang makes a small contribution to the specificity of target recognition restricted to the unpaired nucleotide adjacent to the first base pair (Elbashir et al. 2001). 2'-deoxynucleotides in the 3' overhangs are as efficient as ribonucleotides, but are often cheaper to synthesize and probably more nuclease resistant. Delivery of siRNA may be accomplished using any of the methods known in the art, for example by combining the siRNA with saline and administering the combination intravenously or intranasally or by formulating siRNA in glucose (such as for example 5% glucose) or cationic lipids and polymers can be used for siRNA delivery in vivo through systemic routes either intravenously (IV) or intraperitoneally (IP) (Fougerolles et al. (2008), Current Opinion in Pharmacology, 8:280-285; Lu et al. (2008), Methods in Molecular Biology, vol. 437: Drug Delivery Systems—Chapter 3: Delivering Small Interfering RNA for Novel Therapeutics).

A short hairpin RNA (shRNA) is a sequence of RNA that makes a tight hairpin turn that can be used to typically silence gene expression via RNA interference. shRNA can for example use a vector introduced into cells, in which case preferably the U6 promoter is utilized to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

Preferably, si/shRNAs to be used in the present invention are chemically synthesized using conventional methods that, for example, appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs or shRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

Further molecules effecting RNAi include, for example, microRNAs (miRNA). Said RNA species are single-stranded RNA molecules which, as endogenous RNA molecules, regulate gene expression. Binding to a complementary mRNA transcript triggers the degradation of said mRNA transcript through a process similar to RNA interference. Accordingly, miRNA may be employed as an inhibitor of the signalling pathways in accordance with the present invention.

The term "antibody" as used in accordance with the present invention comprises polyclonal and monoclonal antibodies, as well as derivatives or fragments thereof, which still retain the binding specificity. Antibody fragments or derivatives comprise, inter alia, Fab or Fab' fragments as well as Fd, F(ab')$_2$, Fv or scFv fragments; see, for example Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also includes embodiments such as chimeric (human constant domain, non-human variable domain), single chain and humanised (human antibody with the exception of non-human CDRs) antibodies.

Various techniques for the production of antibodies are well known in the art and described, e.g. in Harlow and Lane (1988) and (1999), loc. cit. Thus, the antibodies can be produced as peptidomimetics. Further, techniques described for the production of single chain antibodies (see, inter alia, U.S. Pat. No. 4,946,778) can be adapted to produce single chain antibodies specific for the target of this invention. Also, transgenic animals or plants (see, e.g., U.S. Pat. No. 6,080,560) may be used to express (humanized) antibodies specific for the target of this invention. Most preferably, the antibody is a monoclonal antibody, such as a human or humanized antibody. For the preparation of monoclonal antibodies, any technique which provides antibodies produced by continuous cell line cultures can be used. Examples for such techniques are described, e.g. in Harlow and Lane (1988) and (1999), loc. cit. and include the hybridoma technique originally developed by Köhler and Milstein Nature 256 (1975), 495-497, the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of STIM2 or an epitope of a STIM2-regulated plasma membrane calcium channel (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, inter alia, viruses or plasmid vectors.

Aptamers are nucleic acid molecules or peptide molecules that bind a specific target molecule. Aptamers are usually created by selecting them from a large random sequence pool, but natural aptamers also exist in riboswitches. Aptamers can be used as macromolecular drugs. Aptamers can be combined with ribozymes to self-cleave in the presence of their target molecule. These compound molecules have additional research, industrial and clinical applications (Osborne et. al. (1997), Current Opinion in Chemical Biology, 1:5-9; Stull & Szoka (1995), Pharmaceutical Research, 12, 4:465-483).

More specifically, aptamers can be classified as nucleic acid aptamers, such as DNA or RNA aptamers, or peptide aptamers. Whereas the former normally consist of (usually short) strands of oligonucleotides, the latter preferably consist of a short variable peptide domain, attached at both ends to a protein scaffold.

The term "peptide" as used herein describes a group of molecules consisting of up to 30 amino acids, whereas the term "protein" as used herein describes a group of molecules consisting of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. The terms "peptide" and "protein" (wherein "protein" is interchangeably used with "polypeptide") also refer to naturally modified peptides/proteins wherein the modification is effected e.g. by glycosylation, acetylation, phosphorylation and the like. Such modifications are well-known in the art.

A ribozyme (from ribonucleic acid enzyme, also called RNA enzyme or catalytic RNA) is an RNA molecule that catalyzes a chemical reaction. Many natural ribozymes catalyze either their own cleavage or the cleavage of other RNAs, but they have also been found to catalyze the aminotransferase activity of the ribosome. Non-limiting examples of well-characterized small self-cleaving RNAs are the hammerhead, hairpin, hepatitis delta virus, and in vitro-selected lead-dependent ribozymes, whereas the group I intron is an example for larger ribozymes. The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site. The basic principle of constructing hammerhead ribozymes is as follows: An interesting region of the RNA, which contains the GUC (or CUC) triplet, is selected. Two oligonucleotide strands, each usually with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences.

A recent development, also useful in accordance with the present invention, is the combination of an aptamer recognizing a small compound with a hammerhead ribozyme. The conformational change induced in the aptamer upon binding the target molecule is supposed to regulate the catalytic function of the ribozyme.

Also encompassed herein are modified versions of these inhibitory compounds.

The term "modified versions of these inhibitory compounds" in accordance with the present invention refers to versions of the compounds that are modified to achieve i) modified spectrum of activity, organ specificity, and/or ii) improved potency, and/or iii) decreased toxicity (improved therapeutic index), and/or iv) decreased side effects, and/or v) modified onset of therapeutic action, duration of effect, and/or vi) modified pharmacokinetic parameters (resorption, distribution, metabolism and excretion), and/or vii) modified physico-chemical parameters (solubility, hygroscopicity, color, taste, odor, stability, state), and/or viii) improved general specificity, organ/tissue specificity, and/or ix) optimised application form and route by, for example, (a) esterification of carboxyl groups, or (b) esterification of hydroxyl groups with carboxylic acids, or (c) esterification of hydroxyl groups to, e.g. phosphates, pyrophosphates or sulfates or hemi-succinates, or (d) formation of pharmaceutically acceptable salts, or (e) formation of pharmaceutically acceptable complexes, or (f) synthesis of pharmacologically active polymers, or (g) introduction of hydrophilic moieties, or (h) introduction/exchange of substituents on aromates or side chains, change of substituent pattern, or (i) modification by introduction of isosteric or bioisosteric moieties, or (j) synthesis of homologous compounds, or (k) introduction of branched side chains, or (k) conversion of alkyl substituents to cyclic analogues, or (l) derivatisation of hydroxyl groups to ketales, acetales, or (m) N-acetylation to amides, phenyl-carbamates, or (n) synthesis of Mannich bases, imines, or (o) transformation of ketones or aldehydes to Schiff's bases, oximes, acetales, ketales, enolesters, oxazolidines, thiazolidines; or combinations thereof.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

In a preferred embodiment, the activity of the target protein of the respective signalling pathway is inhibited such that it has less than 90%, more preferred less than 80%, less than 70%, less than 60% or less than 50% of the activity as compared to the activity it has in the absence of any inhibition. Even more preferred its activity is reduced such that it is less than 25%, more preferred less than 10%, less than 5%, or less than 1% of the activity as compared to the activity it has in the absence of any inhibition. Most preferably, the activity of the target protein is fully inhibited, i.e. no expression or activity is detectable.

The efficiency of an inhibitor can be quantified by comparing the level of expression and/or activity in the presence of an inhibitor to that in the absence of the inhibitor. For example, as a measure may be used: the change in amount of mRNA formed, the change in amount of protein formed, the change in biological activity of the target proteins as described herein below, and/or the change in the cellular phenotype or in the phenotype of an organism. In other words, the efficiency of an inhibitor can be quantified by comparing e.g. the amount of target protein in the presence of an inhibitor to that in the absence of the inhibitor or by determining the biological activity of the target protein present prior to and after administration of the inhibitor, wherein a reduction in the amount or biological activity of the target protein in the presence of or after administration of the inhibitor as compared to in the absence of or prior to said administration is indicative of a successful inhibition of the target protein. Means and methods to determine the amount of mRNA or proteins in a sample or for determining biological activities are well known in the art and include, without being limiting, the following methods.

In cases where an inhibitor acts by affecting the expression level of the target protein, the determination of the expression level of the protein can, for example, be carried out on the nucleic acid level or on the amino acid level.

Methods for determining the expression of a protein on the nucleic acid level include, but are not limited to, northern blotting, PCR, RT-PCR or real RT-PCR. Methods for the determination of the expression of a protein on the amino acid level include but are not limited to western blotting or polyacrylamide gel electrophoresis in conjunction with protein staining techniques such as Coomassie Brilliant blue or silver-staining. Also of use in protein quantification is the Agilent Bioanalyzer technique. These methods are well known in the art.

The determination of binding of potential inhibitors can be effected in, for example, any binding assay, preferably biophysical binding assay, which may be used to identify binding test molecules prior to performing the functional/activity assay with the inhibitor. Suitable biophysical binding assays are known in the art and comprise fluorescence polarisation (FP) assay, fluorescence resonance energy transfer (FRET) assay and surface plasmon resonance (SPR) assay. For example, a modulator acting via binding to an enzyme, and thereby modulating the activity of said enzyme, may be tested by FRET by labelling either the modulator or the enzyme with a donor chromophore and the other molecule with an acceptor chromophore. These chromophore-labelled molecules are then mixed with each other. When they are dissociated, donor emission can be detected upon donor excitation at the appropriate wavelength. However, when the donor and acceptor are in proximity (1-10 nm) due to the interaction of the modulator with the enzyme, the acceptor emission is predominantly observed because of the intermolecular FRET from the donor to the acceptor.

The function of an inhibitor suitable for the method of the present invention may be identified and/or verified by using high throughput screening assays (HTS). High-throughput assays, independently of being biochemical, cellular or other assays, generally may be performed in wells of microtiter plates, wherein each plate may contain, for example 96, 384 or 1536 wells. Handling of the plates, including incubation at temperatures other than ambient temperature, and bringing into contact of test compounds with the assay mixture is preferably effected by one or more computer-controlled robotic systems including pipetting devices. Where large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to the observed biological activity.

The "activin/TGF-β signalling pathway" is well known in the art and has been described, for example, in Keiji Miyazawa et al. (Genes to Cells (2002), 7:1191-1204); Joan Massague and David Wotton (EMBO J (2000) 19:1745-1754), and Xin-Hua Feng and Rik Derynck (Annu. Rev. Cell Dev. (2005) 21:659-693). Receptor ligands, including, for example, TGFB1, TGFB2, TGFB3, ACTIVIN A, ACTIVIN B, ACTIVIN AB, and/or NODAL, bind to a heterotetrameric receptor complex consisting of two type I receptor kinases, including, for example, TGFBR2, ACVR2A, and/or ACVR2B, and two type II receptor kinases, including, for example, TGFBR1, ACVR1B, and/or ACVR1C. This binding triggers phosphorylation and activation of a heteromeric complex consisting of an R-smad, including, for example, SMAD2, and/or SMAD3, and a Co-smad, including, for example, SMAD4.

Accordingly, the term "inhibitor of the activin/TGF-β signalling pathway" refers to an inhibitor of any one of the above recited molecules that form part of this signalling pathway.

Preferably, the inhibitor of the activin/TGF-β signalling pathway is selected from the group consisting of 4-[4-(3,4-Methylenedioxyphenyl)-5-(2-pyridyl)-1H-imidazol-2-yl]-benzamide hydrate (SB431542; Laping et al. 2002), Lefty1 (Gene symbol: LEFTY1; Chen and Shen, Curr Biol (2004) 14:618-624), Lefty2 (Gene symbol: LEFTY2; Meno et al., Molecular Cell (2000) 4:287-298), Follistatin (Gene symbol: FST; Massague and Chen, Genes Dev (2000) 14:627-644), and Cerberus (Gene symbol: CER1; Piccolo et al., Nature (1999) 397:707-710). Even more preferably, the inhibitor of the activin/TGF-β signalling pathway is SB431542.

Preferred amounts of SB431542 to be employed are between about 0.1 and about 100 µM, more preferably between about 1 and about 50 µM, such as for example between about 5 and about 20 µM and most preferably the amount is about 10 µM. Preferred amounts of Lefty2 to be employed are between about 10 and about 10000 ng/ml, more preferably between about 100 and about 1000 ng/ml, such as for example between about 200 and about 500 ng/ml and most preferably the amount is about 500 ng/ml. Preferred amounts of Follistatin to be employed are between about 10 and about 10000 ng/ml, more preferably between about 100 and about 1000 ng/ml, such as for example between about 200 and about 5000 ng/ml and most preferably the amount is about 500 ng/ml. Preferred amounts of Cerberus to be employed are between about 10 and about 10000 ng/ml, more preferably between about 100 and about 1000 ng/ml, such as for example between about 200 and about 500 ng/ml and most preferably the amount is about 500 ng/ml.

The term "about", as used herein, encompasses the explicitly recited amounts as well as deviations therefrom of ±15%. More preferably, a deviation of ±10%, and most preferably of ±5% is encompassed by the term "about".

The "BMP signalling pathway" is well known in the art and has been described, for example, in Keiji Miyazawa et al. (Genes to Cells (2002), 7:1191-1204), Joan Massague and David Wotton (EMBO J (2000) 19:1745-1754), Xin-Hua Feng and Rik Derynck (Annu. Rev. Cell Dev. (2005) 21:659-693), and Mazerbourg et al. (J Biol Chem (2005) 280:32122-32132). Receptor ligands, including, for example, BMP2, BMP4, BMP5, BMP6, BMP7, BMP8A, BMP8B, BMP9, BMP10, BMP15, GDF2, GDF5, GDF6, GDF7, and/or MSTN, bind to a heterotetrameric receptor complex consisting of two type I receptor kinases, including, for example, BMPR1A, BMPR1B, and/or MISR2, and two type II receptor kinases, including, for example, BMPR2, BMPR2B, and/or ALK2. This binding triggers phosphorylation and activation of a heteromeric complex consisting of an R-smad, including, for example, SMAD1, SMAD5, and/or SMAD8, and a Co-smad, including, for example, SMAD4.

Accordingly, the term "inhibitor of the BMP signalling pathway" refers to an inhibitor of any one of the above recited molecules that form part of this signalling pathway.

Preferably, the inhibitor of the BMP signalling pathway is selected from the group consisting of 6-[4-[2-(1-Piperidinyl)ethoxy]phenyl]-3-(4-pyridinyl)-pyrazolo [1,5-a] pyrimidine dihydrochloride (dorsomorphin; Yu et al. 2008), noggin (gene symbol: NOG) and/or chordin (gene symbol: CHRD) (Massague and Chen, Genes Dev (2000) 14:627-644). Most preferably, the inhibitor of the BMP signalling pathway is dorsomorphin.

Preferred amounts of dorsomorphin to be employed are between about 0.1 and about 10 µM, more preferably between about 0.5 and about 5 µM, and most preferably the amount is about 1 µM. Preferred amounts of Noggin to be employed are between about 10 and about 10000 ng/ml, more preferably between about 100 and about 1000 ng/ml, and most preferably the amount is between about 200 and about 500 ng/ml. Preferred amounts of chordin to be employed are between about 10 and about 10000 ng/ml, more preferably between about 100 and about 1000 ng/ml, such as for example between about 200 and about 500 ng/ml and most preferably the amount is about 500 ng/ml.

The term "activator", as used herein, is defined as a compound enhancing the activity of a target molecule, preferably by performing one or more of the following effects: (i) the transcription of the gene encoding the protein to be activated is enhanced, (ii) the translation of the mRNA encoding the protein to be activated is enhanced, (iii) the protein performs its biochemical function with enhanced efficiency in the presence of the activator, and (iv) the protein performs its cellular function with enhanced efficiency in the presence of the activator. Accordingly, the term "activator" encompasses both molecules that have a directly activating effect on the specific pathway but also molecules that are indirectly activating, e.g. by interacting for example with molecules that negatively regulate (e.g. suppress) said pathway. The above recited definitions for such compounds as well as methods of testing them apply mutatis mutandis to the definition of an activator. Preferably, the activator is a small molecule or protein/polypeptide.

Preferably, the level of activity is 10% more than the activity in absence of the activator, more preferred, the level of activity is 25%, such as 50% more than the activity in absence of the activator. Yet more preferred are activators enhancing the level of activity to 75%, 80%, 90% or 100% more than the activity in absence of the activator.

The term "canonical WNT signalling pathway" is well known in the art and has been described, for example, in Logan and Nusse (Annu. Rev. Cell Dev. Biol. (2004) 20:781-810). Wnt ligands, including, for example Wnt1, Wnt3, Wnt3a, Wnt4, Wnt5a, Wnt7a, Wnt7b, and/or Wnt11, bind to a heteromeric receptor complex, including, for example, FZD1, FZD2, FZD3, FZD4, FZD5, FZD6, FZD8, FZD9, FZD10, LRP5, and/or LRP6, causing a signal to be transduced to proteins including, for example, dishevelled, axin, adenomatous polyposis coli, glycogen synthase kinase 3-beta, and beta-catenin. This results in beta-catenin forming a complex with transcription factors including, for example, lymphoid enhancer-binding factor 1, and T cell-specific transcription factor, which then modulates transcription.

Accordingly, the term "activator of the canonical WNT signalling pathway" refers to an activator of any one of the above recited molecules that form part of this signalling pathway.

Preferably, the activator of the canonical WNT signalling pathway is selected from the group consisting of 6-[[2-[[4-(2,4-dichlorophenyl)-5-(5-methyl-1H-imidazol-2-yl)-2-pyrimidinyl] amino] ethyl] amino]-3-pyridinecarbonitrile (CHIR 99021; Ring et al., Diabetes (2003) 52:588-595), 3-(2,4-dichlorophenyl)-4-(1-methyl-1H-indol-3-yl)-1H-pyrrole-2,5-dione (SB 216763; Coghlan et al., Chemistry & Biology (2000) 7:793-803), 3-[[6-(3-aminophenyl)-7H-pyrrolo[2,3-d]pyrimidin-4-yl]oxy]-phenol (TWS119; Ding et al., Proc. Natl. Acad. Sci. USA (2003): 7632-7637), 3-[(3-chloro-4-hydroxyphenyl)amino]-4-(2-nitrophenyl)-1H-pyrrole-2,5-dione (SB 415286; Coghlan et al., Chemistry & Biology (2000) 7:793-803), 6-bromo-3-[(3E)-1,3-dihydro-3-(hydroxyimino)-2H-indol-2-ylidene]-1,3-dihydro-(3Z)-2H-indol-2-one (BIO; Sato et al. Nat Med (2004) 10:55-63), Wnt1 (Gene Symbol: WNT1; Logan and Nusse (Annu. Rev. Cell Dev. Biol. (2004) 20:781-810) and Wnt3a (Gene Symbol: WNT3A; Logan and Nusse (Annu. Rev. Cell Dev. Biol. (2004) 20:781-810), and Wnt3 (Gene Symbol: WNT3; Logan and Nusse (Annu. Rev. Cell Dev. Biol. (2004) 20:781-810). Most preferably, the activator of the canonical WNT signalling pathway is CHIR 99021.

Preferred amounts of CHIR 99021 to be employed are between about 0.05 and about 4 µM, more preferably between about 1.5 and about 3.5 µM, and most preferably the amount is about 3 µM. Preferred amounts of SB 216763 to be employed are between about 0.05 and about 30 µM, more preferably between about 1.5 and about 3.5 µM, and most preferably the amount is about 3 µM. Preferred amounts of TWS119 to be employed are between about 0.005 and about 10 µM. Preferred amounts of SB 415286 to be employed are between about 0.01 and about 10 µM. Preferred amounts of BIO to be employed are between about 0.01 and about 30 µM. Preferred amounts of Wnt1 to be employed are between about 1 and about 500 ng/ml. Preferred amounts of Wnt3a to be employed are between about 1 and about 500 ng/ml. Preferred amounts of Wnt3 to be employed are between about 1 and about 500 ng/ml.

The "Hedgehog signalling pathway" is well known in the art and has been described, for example, in Rubin and de Sauvage (Nature Reviews Drug Discovery (2006) 5:1026-1033). Hedgehog ligands, including, for example, Sonic hedgehog, Indian hedgehog, and/or Desert hedgehog, bind to a receptor, including, for example, Patched1, causing a signal to be transduced to proteins including, for example, Smoothened, and/or SUFU, GLI1, GLI2, GLI3, which then modulates transcription.

Accordingly, the term "activator of the Hedgehog signalling pathway" refers to an activator of any one of the above recited molecules that form part of this signalling pathway.

Preferably, the activator of the Hedgehog signalling pathway is selected from the group consisting of 9-cyclohexyl-N-[4-(morpholinyl)phenyl]-2-(1-naphthalenyloxy)-9H-purin-6-amine (purmorphamine (PMA); Sinha and Chen, Nat. Chem. Biol. (2006) 2:29-30), SHH (Gene Symbol: SHH) and SHH C24II (Taylor et al., Biochemistry (2001) 40:4359-4371), N-Methyl-N'-(3-pyridinylbenzyl)-N'-(3-chlorobenzo [b] thiophene-2-carbonyl)-1,4-diaminocyclohexane (smoothened agonist SAG; Chen et al., Proc. Natl. Acad. Sci. USA (2002) 99:14071-14076), and 3-chloro-4,7-difluoro-N-(4-methoxy-3-(pyridin-4-yl) benzyl)-N-(4-(methylamino) cyclohexyl) benzo[b] thiophene-2-carboxamide (Hh-Ag1.5; Frank-Kamenetsky et al. journal of Biology (2002) 1:10.2-10.19). Most preferably, the activator of the Hedgehog signalling pathway is PMA.

Preferred amounts of PMA to be employed are between about 0.25 and about 1 µM, more preferably between about 0.4 and about 0.8 µM, and most preferably the amount is about 0.5 µM. Preferred amounts of SHH to be employed are between about 50 and about 1000 ng/ml. Preferred amounts of SHH C24II to be employed are between about 10 and about 500 ng/ml. Preferred amounts of smoothened agonist SAG to be employed are between about 1 and about 100 nM. Preferred amounts of Hh-Ag1.5 to be employed are between about 1 and about 50 nM.

The term "oxidation" is well known in the art and has been described, for example, in Jomova et al. (Basic Neurochemistry: Molecular, Cellular, and Midcal Aspects (6$^{th}$ Edition; 1998) pages 711-730). Free Radicals are molecules or fragments of molecules containing unpaired electrons, including, for example, superoxide, nitric oxide, peroxynitrite, and hydroxyl radicals. Free radicals cause cellular damage by processes including, for example, protein oxidation, DNA oxidation, DNA fragmentation, lipid oxidation, carbonyl compound formation, and/or protein cross-linking. Proteins including, for example, superoxide dismutase 1, superoxide dismutase 2, superoxide dismutase 3, catalase, and/or glutathione can detoxify free radicals.

Accordingly, the term "inhibitor of oxidation" refers to an inhibitor of any one of the above recited molecules involved in cellular oxidative processes.

Preferably, the inhibitor of oxidation is selected from the group consisting of (5R)-[(1S)-1,2-dihydroxyethyl]-3,4-dihydroxyfuran-2(5H)-one (ascorbic acid; Jomova et al. Molecular and Cellular Biochemistry (2010) 345:91-104); superoxide dismutase 1 (Gene Symbol SOD1), superoxide dismutase 2 (Gene Symbol: SOD2) and superoxide dismutase 3 (Gene Symbol: SOD3) (Zeiko et al., Free Radical Biology and Medicine (2002) 33:337-349); (2S)-2-amino-5-[[(1R)-1-[[(2R)-2-[[(4S)-4-amino-5-hydroxy-1,5-dioxopentyl] amino]-3-(carboxymethylamino)-3-oxopropyl] disulfanylmethyl]-2-(carboxymethylamino)-2-oxoethyl] amino]-5-oxopentanoic acid (glutathione; Jomova et al. Molecular and Cellular Biochemistry (2010) 345:91-104), (R)-5-(1,2-dithiolan-3-yl)pentanoic acid (lipoic acid; Jomova et al. Molecular and Cellular Biochemistry (2010) 345:91-104), [(2R,3R)-5,7-dihydroxy-2-(3,4,5-trihydroxyphenyl) chroman-3-yl]3,4,5-trihydroxybenzoate (epigallocatechin gallate; Jomova et al. Molecular and Cellular Biochemistry (2010) 345:91-104), (1E,6E)-1,7-bis(4-hydroxy-3-methoxyphenyl)-1,6-heptadiene-3,5-dione (curcumin; Jomova et al. Molecular and Cellular Biochemistry (2010) 345:91-104), N-[2-(5-methoxy-1H-indol-3-yl) ethyl] acetamide (melatonin; Hardeland, Endocrine (2005) 27:119-130), 4-(2-Hydroxyethyl)-1,2-benzenediol (hydroxytyrosol; Fabiani et al., J. Nutr. (2008) 138:1411-1416), and 2-[(2E, 6E,10E,14E,18E,22E,26E,30E,34E)-3,7,11,15,19,23,27,31, 35,39-decamethyltetraconta-2,6,10,14,18,22,26,30,34,38-decaenyl]-5,6-dimethoxy-3-methylcyclohexa-2,5-diene-1, 4-dione (ubiquinone; Cabrini et al., Free Radic. Res. Commun. (1986) 2:85-92), catalase, vitamin E (Bucioli et al. BMC Complement Altern Med. 2011 Dec. 20; 11(1):133). Most preferably, the inhibitor of oxidation is ascorbic acid.

Preferred amounts of ascorbic acid to be employed are between about 50 µM and about 1 mM, more preferably between about 100 and about 500 µM, and most preferably the amount is about 150 µM. Preferred amounts of superoxide dismutase 1, 2 or 3 to be employed are between about 10 and about 500 units/ml. Preferred amounts of glutathione to be employed are between about 1 and about 10 ng/µl. Preferred amounts of lipoic acid to be employed are between about 200 and about 1000 µM. Preferred amounts of epigallocatechin gallate to be employed are between about 10 and about 100 µg/ml. Preferred amounts of curcumin to be employed are between about 10 and about 100 µM. Preferred amounts of melatonin to be employed are between about 10 and about 200 µM. Preferred amounts of hydroxytyrosol to be employed are between about 10 and about 100 µM. Preferred amounts of ubiquinone to be employed are between about 10 and about 50 µM. Preferred amounts of catalase to be employed are between about 10 and about 500 units/ml. Preferred amounts of vitamin E to be employed are between about 100 and about 1000 µM.

All of the above recited compounds and proteins are well known in the art and are commercially available to the skilled person. For example, SB-431542 may be obtained from Ascent Scientific, dorsomorphin may be obtained from Tocris, CHIR 99021 may be obtained from Axon Medchem, PMA may be obtained from Alexis and ascorbic acid may be obtained from Sigma.

In accordance with the present invention, the term "neural medium" refers to a medium comprising about 90 to about 9.5% of a basal cell culture medium and about 0.5 to about 10% of serum-free supplements. Non-limiting examples of serum-free supplements are N2 supplement and/or B27 supplement. Preferred amounts of e.g. N2 supplement are between about 0.5 and about 5% and preferred amounts of B27 supplement are up to about 5%. Further additives such as e.g. antibiotics or amino acid can be included in the medium. The skilled person is aware of such additional compounds and how to use them.

In a preferred embodiment, the neural medium is N2B27 medium comprising about 50% DMEM-F12 (e.g. from Invitrogen)/about 50% Neurobasal (e.g. from Invitrogen)/about 1:200 N2 supplement (e.g. from Invitrogen)/about 1:100 B27 supplement lacking vitamin A (e.g. from Invitrogen) and 1% Penicillin/Streptomycin/Glutamine (e.g. from PAA).

Depending on the respective embodiment, the neural medium may further comprise the compounds (inhibitors and/or activators) specifically recited in the respective embodiments.

Employing the above described culture conditions, differentiation of mammalian pluripotent stem cells is achieved in step (a). Differentiation may be carried out in suspension culture or on a solid support. When using suspension culture, cells are grown under conditions in which they do not adhere to a matrix or the bottom of the dish. When grown on a solid support, cells are grown under conditions that enable the adherence of cells to a surface. These cell culture conditions and methods are well known in the art and the skilled person is capable of choosing the conditions and methods most suitable. Most preferably, the mammalian pluripotent stem cells are are cultured such that embryoid bodies are formed. Even more preferably, the formation of embryoid bodies is achieved by culture in suspension culture.

The term "embryoid bodies" as used herein refers to aggregates of cells derived from pluripotent stem cells. Embryoid bodies (embryoid body; EB) are generally comprised of a large variety of differentiated cell types. Cell aggregation can for example be imposed by hanging drop or other methods that prevent cells from adhering to a surface, thus allowing the embryoid bodies to form their typical colony growth. Upon aggregation, differentiation is typically initiated and the cells begin to a limited extent to recapitulate embryonic development.

In the subsequent step, these differentiated mammalian pluripotent stem cells are plated onto a solid support, such as e.g. a suitable cell culture dish. The differentiated mammalian pluripotent stem cells may be plated as they are (i.e. without disaggregation). In those cases where the differentiated mammalian pluripotent stem cells form embryoid bodies, the embryoid bodies may be plated without disaggregation or, alternatively, may be mechanically disaggregated into fragments. For example, using a 1 ml pipette and pipetting the solution comprising the embryoid bodies up and down is sufficient for disaggregation. Most preferably, the fragments of the embryoid bodies comprise about 500 cells. Most preferably, when using embryoid bodies, then the embryoid bodies are disaggregated prior to plating.

The term "solid support", as used herein, refers to a surface enabling the adherence of cells thereto. Said surface may be, for example, the wall or bottom of a culture vessel, a plastic or glass slide such as for example a microscope slide or (a) bead(s) offering a surface for adherence. Conditions suitable to allow attachment of the cells are well known to the skilled person and have been described, for example, in Schmitz, 2009 (Schmitz, S. (2009). Der Experimentator: Zellkultur. Spektrum Akademischer Verlag, 2. Aufl.). Preferably, said conditions are achieved by coating the solid support with an agent that enhances attachment of cells to the solid support. Such coating agents as well as methods of using them are also well known in the art and include, without being limiting, matrigel as for example described in the examples below, but also gelatine, fibronectin, poly-L-lysin, poly-L-ornithin, collagen, tenascin, perlecan, phosphocan, brevican, neurocan, thrombospondin, laminin, or defined mixtures of these attachment molecules, such as CellStart (Invitrogen). Most preferably, the solid support is coated with matrigel. Matrigel is well known in the art and is commercially available, for example from BD Biosciences.

After plating, the differentiated mammalian pluripotent stem cells are cultured in NPBSC expansion medium.

In accordance with the present invention, the NPBSC expansion medium is based on the above defined neural medium, further comprising an activator of the canonical WNT signalling pathway, an activator of the Hedgehog signalling pathway and an inhibitor of oxidation. As used herein, the term "NPBSC expansion medium" always refers to a medium comprising these three specifically recited activators and inhibitors. Preferred compounds and amounts thereof have been defined herein above.

The term "expanding", in accordance with the present invention, refers to a multiplication of cells, thus resulting in an increase in the total number of cells. Preferably, cells are expanded to at least twice their original number, more preferably to at least 10 times their original number, such as for example at least 100 times, such as at least 1,000 times their original number and most preferably to at least 10,000 times, such as at least 100,000 times their original number.

Expansion of the cells may be achieved by known methods, e.g. by culturing the cells under appropriate conditions to high density or confluence and subsequent splitting (or passaging) of the cells, wherein the cells are re-plated at a diluted concentration into an increased number of culture dishes or onto solid supports. With increasing passage number, the amount of cells obtained therefore increases due to cell division. The skilled person is aware of means and methods for splitting cells and can determine the appropriate time point and dilution for splitting cells. Preferably, cells are split between 1:5 and 1:10 every five to seven days.

The splitting and expansion step defined in (c) is repeated at least two times. After two repeats, the cells obtained are the neural plate border stem cells of the invention and the cultures are (substantially) free of contaminating non-NPB-SCs. As defined elsewhere herein, the term "at least" refers to a minimum requirement of repeats and includes two or more repeats, such as e.g. (at least) three repeats, (at least) four repeats, (at least) five repeats, (at least) six repeats, (at least) seven repeats, (at least) eight repeats, (at least) nine repeats, (at least) ten repeats, (at least) twenty repeats, (at least) fivty repeats and so on. It will be understood that the number of repeats defined in step (d) refers to the total number of times step (c) is to be carried out. In other words, when step (d) requires "at least two times", then the splitting and expansion of step (c) is carried out twice.

In accordance with the present invention, a method is provided for the generation of a novel type of neuronal precursor cells from pluripotent stem cells, such as e.g. induced pluripotent stem cells. These neural plate border stem cells can be clonally expanded under chemically defined conditions (i.e. as characterised in step (d) of the method of the invention), thus demonstrating that these cells are stem cells. Moreover, the cells obtained by the method of the present invention can differentiate into neural tube and neural crest cells. As such, NPSCs can differentiate into both PNS neurons and CNS neurons, including midbrain dopaminergic and motor neurons. Thus, they provide a useful source of CNS and PNS neurons for disease modelling and drug discovery.

Surprisingly, it was found that the combination of inhibition of the activin/TGF-β and the BMP signalling pathways with an activation of both the Hedgehog signalling pathway and the canonical WNT signalling pathway enables the production of a new precursor cell type, namely neural plate border stem cells. Canonical WNT and Hedgehog signalling—in the presence of inhibition of cellular oxidation processes—specifies self-renewal of NPBSCs by maintaining a neural plate border-like identity. The morphogens employed in accordance with the present invention have a well-defined role in development. During gastrulation, the neural plate is specified into the medial or border areas, which then differentiate to form neurons in the CNS and PNS, respectively. WNT and BMP signaling control this specification. WNT proteins induce caudal neural plate border specification in neural plate. BMP signalling is necessary for instruction into the neural plate border identity, and SHH has been shown to antagonize BMP induced specification.

Based on the knowledge in the prior art, the skilled person was aware that Hedgehog and WNT signalling oppose each other during patterning of cells of the central nervous system and the peripheral nervous system. Accordingly, when aiming at providing cells capable of differentiating into both the central nervous system and the peripheral nervous system, the dual usage of Hedgehog and WNT signalling is counterintuitive, as it would be expected that the dual signal would disrupt the normal patterning signals, thus resulting in a cell without clear differentiation signals. Surprisingly, however, it was found in accordance with the present invention that the combination of Hedgehog and WNT signalling leads to the preservation of the ability to differentiate into both the central nervous system and the peripheral nervous system. The cells maintain themselves in this undifferentiated state and expand robustly while maintaining this differentiation competence to both central and peripheral nervous system cell types.

Therefore, through a combination of opposing morphogens, WNT and Hedgehog, an environment was created that induces the self-renewal of NPBSCs and inhibits their commitment to either CNS or PNS neuronal cell types. Furthermore, as is shown in example 2, the NPBSCs obtained by the method of the present invention are developmentally upstream of neural rosette-derived cells previously described in the art (Zhang et al., Nat Biotechnol 19, 1129-1133; Koch et al., Proc Natl Acad Sci USA 106, 3225-3230).

The neural plate border stem cells of the present invention are a valuable source of material for disease modelling studies. NPBSCs can be readily derived from mammalian (e.g. human) pluripotent stem cells, including patient-specific iPS cells, without the need of manual selections steps. However, unlike other neural cell types, NPBSCs can be cultured under chemically defined conditions in which proteins can be substituted for small molecules and have a consistently high splitting ratio (usually 1:10 every five to seven days). This considerably reduces both the batch-to-batch variability inherent to purified proteins as well as the expense. The ability for efficient expansion as well as competence for efficient differentiation into both PNS and CNS neurons enables the large-scale production of disease models for applications such as high-throughput drug discovery screens.

In a further preferred embodiment of the method of the invention, the differentiated mammalian pluripotent stem cells are plated in step (b) at a density of about 1000 to 100,000 per $cm^2$.

In another preferred embodiment of the method of the invention, the NPBSCs are characterized by the expression of at least three markers selected from the group consisting of FORSE1, MSX1, PHOX2B, PAX3, PAX6, SOX1, SOX2, NESTIN, IRX3, HOXA2, HOXB2, HES5, DACH1, PLZF, LMO3, EVI1 and ASCL1.

All of the marker proteins referred to herein are defined in accordance with the pertinent prior art.

In accordance with the present invention, "FORSE1" refers to the surface epitope recognized by the antibody FORSE1 and has been described in the art, for example in Tole et al., J Neurosci (1995) 15:957-969. FORSE1 is a carbohydrate epitope expressed on the cell surface expressed in specific populations during neuronal development and has been described in the art, for example in Allendoerfer et al., Mol. Cell. Neurosci. (1995) 6:381-395.

In accordance with the present invention, "MSX1" refers to Msh homeobox 1, a protein that in humans is encoded by the MSX1 gene. MSX1 is a transcriptional repressor during embryogenesis through interactions with components of the core transcription complex and other homeoproteins. Human MSX1 is represented by the NCBI reference NP_002439.2 and has been described in the art, for example in Davidson, Trends in Genetics (1995) 11:405-411

"PHOX2B", as used throughout the present invention, refers to Paired-like homeobox 2b, a protein that in humans is encoded by the PHOX2B gene. PHOX2B is a transcriptional regulator. Human PHOX2B is represented by the NCBI reference NP_003915.2 and has been described in the art, for example in Samad et al., Development (2004) 131:4071-4083.

In accordance with the present invention, "PAX3" and "PAX6" refer to Paired box 3 and Paired box 6, respectively, which are proteins that in humans are encoded by the PAX3 and PAX6 genes, respectively. PAX3 and PAX6 are transcriptional regulators. Human PAX3 is represented by the NCBI references NP_000429.2, NP_001120838.1, NP_039230.1, NP_852122.1, NP_852123.1, NP_852124.1, NP_852125.1 and NP_852126.1; and PAX6 is represented by the NCBI references NP_000271.1, NP_001121084.1, NP_001595.2. PAX3 and PAX6 have been described in the art, for example in Strachan and Read (Curr. Opin. Genet. Dev. (1994) 4:427-438).

In accordance with the present invention, "SOX1" and "SOX2" refer to Sex determining region Y-box 1 and Sex determining region Y-box 2, which are proteins that in humans are encoded by the SOX1 and SOX2 genes, respectively. SOX1 and SOX2 are transcriptional regulators. Human SOX1 is represented by the NCBI reference NP_005977.2, and SOX2 is represented by the NCBI reference NP_003097.1. SOX1 and SOX2 have been described in the art, for example in Uchikawa et al., (Mech. Dev. (1999) 84:103-120).

"NESTIN", as used throughout the present invention, refers to NESTIN, a protein that in humans is encoded by the NES gene. NESTIN is an intermediate filament. Human NESTIN is represented by the NCBI reference NP_006608.1 and has been described in the art, for example in Michalcyzk and Ziman (Histol. Histopathol. (2005) 20:665-671).

In accordance with the present invention, "IRX" refers to Iroquois homeobox 3, a protein that in humans is encoded by the IRX3 gene. IRX3 is a transcriptional regulator. Human IRX3 is represented by the NCBI reference NP_077312.2 and has been described in the art, for example in Briscoe and Ericson (Current Opinion in Neurobiology (2001) 11:43-49).

In accordance with the present invention, "HOXA2" and "HOXB2" refer to Homeobox A2 and Homeobox B2, which are proteins that in humans are encoded by the HOXA2 and HOXB2 genes, respectively. HOXA2 and HOXB2 are transcriptional regulators. Human HOXA2 is represented by the NCBI reference NP_006726.1, and HOXB2 is represented by the NCBI reference NP_002136.1. HOXA2 and HOXB2 have been described in the art, for example in Davenne et al. (Neuron (1999) 22:677-691).

"HES5", as used throughout the present invention, refers to Hairy and enhancer of split 5, a protein that in humans is encoded by the HES5 gene. HES5 is a transcriptional repressor, which is activated downstream of the Notch pathway. Human HES5 is represented by the NCBI reference NP_001010926.1 and has been described in the art, for example in Ohtsuka et al. (EMBO J (1999) 18:2196-2207).

In accordance with the present invention, "DACH1" refers to Dachshund homolog 1, a protein that in humans is encoded by the DACH1 gene. DACH1 is a chromatin-associated protein that interacts with transcription factors to regulate gene expression. Human DACH1 is represented by the NCBI references NP_004383.3, NP_542937.2, NP_542938.2 and has been described in the art, for example in Watanabe et al. (Proc. Natl. Acad. Sci. USA (2011) 108:12384-12389).

"PLZF", as used throughout the present invention, refers to Promyelotic leukemia zinc finger, a protein that in humans is encoded by the ZBTB16 gene. PLZF is a transcriptional regulator. Human PLZF is represented by the NCBI references NP_001018011.1 and NP_005997.2, and has been described in the art, for example in Raberger et al. (Proc. Natl. Acad. Sci. (2008) 105:17919-17924).

In accordance with the present invention, "LMO3" refers to LIM domain only 3, a protein that in humans is encoded by the LMO3 gene. LMO3 is a transcriptional regulator. Human LMO3 is represented by the NCBI reference NP_001001395.1, NP_001230538.1, NP_001230539.1, NP_001230540.1, NP_001230541.1, NP_001230542.1, and NP_061110.2 and has been described in the art, for example in Isogai et al. (PloS ONE (2011) 6:e19297).

In accordance with the present invention, "EVI1" refers to Ectopic viral integration site 1, a protein that in humans is encoded by the MECOM gene. EVI1 a transcriptional regulator. Human EVI1 is represented by the NCBI reference NP_001098547.3, NP_001098548.2, NP_001157471.1, NP_001157472.1, NP_001192123.1, NP_004982.2, and NP_005232.2 and has been described in the art, for example in Wieser (Gene (2007) 396:346-357).

"ASCL1", as used throughout the present invention, refers to achaete-scute complex homolog 1, a protein that in humans is encoded by the ASCL1 gene. ASCL1 is a transcriptional regulator. Human ASCL1 is represented by the NCBI reference NP_004307.2 and has been described in the art, for example in Kageyama et al. (Int J Biochem Cell Biol (1997) 29:1389-1399).

The term "at least three", as used herein, encompasses also at least four, at least five, at least six, at least seven, at least eight, at least nine, at least ten different amino acids or more, such as at least eleven, at least 12, at least 13, at least 14, at least 15 or all 16 of the recited markers. It will be appreciated by the skilled person that this term further encompasses exactly three, exactly four, exactly five, exactly six, exactly seven, exactly eight, exactly nine, exactly ten, exactly eleven, exactly 12, exactly 13, exactly 14, exactly 15 or exactly 16 markers from the recited list of markers. Preferably, one of said at least three markers is PHOX2B. For example, the at least three markers may comprise a combination of PHOX2B with one or more markers selected of MSX1, IRX3 or PAX3 and one or more markers selected of PAX6, SOX1, SOX2 or NES, e.g. the at least three markers may include: MSX1, PAX6 and PHOX2B; IRX3, SOX1 and PHOX2B; MSX1, SOX1 and PHOX2B; MSX1, SOX2 and PHOX2B; IRX3, SOX2 and PHOX2B; IRX3, PAX6 and PHOX2B; MSX1, NES and PHOX2B; IRX3, NES and PHOX2B; PAX3, PAX6 and PHOX2B; PAX3, SOX2 and PHOX2B; PAX3, SOX1 and PHOX2B; and/or PAX3, NES and PHOX2B. Alternatively, the cells are characterized by the combined expression of the markers SOX2, IRX3, and MSX1 or of the markers SOX1, SOX2, NES, and PAX6.

Preferably, the at least three markers are human marker proteins.

Preferably, the NPBSCs are a population of cells comprising at least 70% of cells expressing three or more of the above defined markers, more preferably at least 80%, such as at least 85%, such as at least 90%, such as at least 95%, more preferably at least 98%, even more preferably at least 99% and most preferably 100%.

The skilled person is aware of suitable methods of determining whether three or more of the above recited markers are expressed by the cells. Such methods include, without being limiting, determining the expression of a marker on the amino acid level as well as on the nucleic acid level.

Methods for the determination of expression levels of a marker on the amino acid level include but are not limited to immunohistochemical methods as described in the appended examples but also e.g. western blotting or polyacrylamide gel electrophoresis in conjunction with protein staining techniques such as Coomassie Brilliant blue or silver-staining. Also of use in protein quantification is the Agilent Bioanalyzer technique. Further methods of determination include, without being limiting, cell sorting approaches such as magnetic activated cell sorting (MACS) or flow cytometry activated cell sorting (FACS) or panning approaches using immobilised antibodiesm as described for example in Dainiak et al. (Adv Biochem Eng Biotechnol. 2007; 106:1-18). Methods for determining the expression of a protein on the nucleic acid level include, but are not limited to, northern blotting, PCR, RT-PCR or real time PCR as well as techniques employing microarrays. All these methods are well known in the art and have been described in part in the appended examples.

In a further preferred embodiment of the method of the invention, the NPBSCs are characterized by a lack of expression of at least one of the markers OCT4, NANOG, AFP, T, SOX17, EOMES, GSH2, OLIG2, CK8, CK18, NKX2.2, NKX6.1, HOXB8, HOXA5, FOXA2 and VCAM-1.

In accordance with the present invention, "OCT4" refers to Octamer binding protein 4, a protein that in humans is encoded by the POU5f1 gene. OCT4 is a transcriptional regulator.

Human OCT4 is represented by the NCBI references NP_001167002.1, NP_001167002.1, and NP_976034.4 and has been described in the art, for example in Wang and Dai (Stem Cells (2010) 28:885-893).

In accordance with the present invention, "NANOG" refers to Nanog homeobox, a protein that in humans is encoded by the NANOG gene. NANOG a transcriptional regulator. Human NANOG is represented by the NCBI reference NP_079141.2 and has been described in the art, for example in Chambers et al. (Cell (2003) 113:643-655).

In accordance with the present invention, "AFP" refers to Alpha-fetoprotein, a protein that in humans is encoded by the AFP gene. AFP is a plasma protein produced by the yolc sak and liver during fetal life. Human OCT4 is represented by the NCBI reference NP_001125.1 and has been described in the art, for example in Marubashi et al. (Ann Surg Oncol (2011) 18:2200-2209).

In accordance with the present invention, "T" refers to T, brachyury homolog, a protein that in humans is encoded by the Tgene. T is a transcriptional regulator. Human T is represented by the NCBI reference NP_003172.1 and has been described in the art, for example in Fernando et al. (J Clin Invest (2010) 120:533-544).

In accordance with the present invention, "SOX17" refers to Sex determining region Y-box 17, a protein that in humans is encoded by the SOX17 gene. SOX17 is a transcriptional regulator. Human SOX17 is represented by the NCBI reference NP_071899.1 and has been described in the art, for example in Chew et al. (J Neurosci (2011) 31:13921-13935).

In accordance with the present invention, "EOMES" refers to Eomesodermin, a protein that in humans is encoded by the EOMES gene. EOMES is a transcriptional regulator. Human OCT4 is represented by the NCBI reference NP_005433.2 and has been described in the art, for example in Teo et al. (Genes Dev (2011) 25:238-250).

In accordance with the present invention, "GSH2" refers to GS homeobox 2, a protein that in humans is encoded by the GSX2 gene. GSH2 is a transcriptional regulator. Human GSH2 is represented by the NCBI reference NP_573574.1 and has been described in the art, for example in Waclaw et al. (Neuron (2009) 63:451-465).

In accordance with the present invention, "OLIG2" refers to Oligodendrocyte lineage transcription factor 2, a protein that in humans is encoded by the OLIG2 gene. OLIG2 is a transcriptional regulator. Human OLIG2 is represented by the NCBI reference NP_005797.1 and has been described in the art, for example in Ahn et al. (PloS ONE (2008) 3:e3917).

In accordance with the present invention, "CK8" refers to Cytokeratin 8, a protein that in humans is encoded by the KRT8 gene. CK8 forms intermediate filaments through dimerization with other keratin family proteins. Human CK8 is represented by the NCBI reference NP_002264.1 and has been described in the art, for example in Merjava et al. (Invest Opthalmol Vis Sci (2011) 52:787-794).

In accordance with the present invention, "CK18" refers to Cytokeratin 18, a protein that in humans is encoded by the KRT18 gene. CK18 forms intermediate filaments through dimerization with other keratin family proteins. Human CK18 is represented by the NCBI references NP_000215.1 and NP_954657.1 and has been described in the art, for example in Stanke et al. (BMC Med Genet (2011) 12:62).

In accordance with the present invention, "NKX2.2" refers to NK transcription factor related locus 2, a protein that in humans is encoded by the NKX2-2 gene. NKX2.2 is a transcriptional regulator. Human NKX2.2 is represented by the NCBI reference NP_002500.1 and has been described in the art, for example in Smith et al. (Cancer Cell (2006) 9:405-416).

In accordance with the present invention, "NKX6.1" refers to NK6 homeobox 1 a protein that in humans is encoded by the NKX6-1 gene. NKX6.1 is a transcriptional regulator. Human NKX6.1 is represented by the NCBI reference NP_006159.2 and has been described in the art, for example in Donelan et al. (J Biol Chem (2010) 285: 12181-12189).

In accordance with the present invention, "HOXB8" refers to Homeobox B8, a protein that in humans is encoded by the HOXB8 gene. HOXB8 is a transcriptional regulator. Human HOXB8 is represented by the NCBI reference NP_076921.1 and has been described in the art, for example in Knoepfler et al. (Oncogene (2001) 20:5440-5448).

In accordance with the present invention, "HOXA5" refers to Homeobox A5, a protein that in humans is encoded by the HOXA5 gene. HOXA5 is a transcriptional regulator. Human HOXA5 is represented by the NCBI reference NP_061975.2 and has been described in the art, for example in Gray et al. (JOP (2011) 12:216-219).

In accordance with the present invention, "FOXA2" refers to Forkhead box A2, a protein that in humans is encoded by the FOXA2 gene. FOXA2 is a transcriptional regulator. Human FOXA2 is represented by the NCBI references NP_068556.2 and NP_710141.1 and has been described in the art, for example in Popovic et al. (Biochem Biophys Acta (2010) 1799:411).

In accordance with the present invention, "VCAM-1" refers to Vascular cell adhesion molecule 1, a protein that in humans is encoded by the VCAM-1 gene. VCAM-1 is a surface sialoglycoprotein mediating leukocyte-endothelial cell adhesion and signal transduction. Human VCAM-1 is represented by the NCBI references NP_001069.1, NP_001186763.1, and NP_542413.1 and has been described in the art, for example in Nishihira et al. (Cell Biol Int (2011) 35:475-81).

All of the definitions provided herein above for markers expressed by the cells in accordance with the invention, in particular the methods referred for determining the presence or absence of marker expression, apply mutatis mutandis to these markers that are lacking expression in the cells in accordance with the invention. Moreover, it is preferred that the NPBSCs are a population of cells comprising less than 30% of cells expressing one or more of the markers defined in this embodiment, more preferably less than 20%, such as less than 15%, such as less than 10%, such as less than 5%, more preferably less than 3%, even more preferably less than 1% and most preferably 0%. Preferably, the markers to be absent are human marker proteins.

In a particularly preferred embodiment of the method of the invention, the NPBSCs are characterised by (i) the expression of SOX1, MSX1, and PHOX2B and the lack of expression of NKX6.1 and VCAM-1; or (ii) the expression of SOX2, IRX3, and MSX1 and the lack of expression of HOXB8, HOXA5 and VCAM-1.

In a preferred embodiment, the method of the present invention further comprises differentiating the NPBSCs obtained in step (d) into: (i) peripheral nervous system neurons; (ii) central nervous system neurons; (iii) midbrain dopaminergic neurons; (iv) motor neurons; (v) neural crest-derived mesenchymal cells; (vi) astrocytes; or (vii) neural rosettes.

Methods of differentiating known precursor cells into the above recited cell types are known in the art and the skilled person is capable of testing and employing these conditions for achieving the desired differentiation also when using the NPBSCs of the present invention as the starting point. Preferred methods of differentiating the NPBSCs of the present invention are described below.

Accordingly, in one preferred embodiment, the method of the present invention further comprises (i) culturing the NPBSCs obtained in step (d) in a neural medium comprising an activator of the canonical WNT signalling pathway for about 48 to 72 hours; (ii) adding an activator of the BMP pathway to the culture of step (i) for about 192 hours and (iii) maturing the culture of step (ii) for about 336 hours in a neural medium containing at least two different neurotrophins and an inhibitor of oxidation; thereby differentiating the NPBSCs into peripheral nervous system neurons.

The "BMP signalling pathway" or "BMP pathway" is well known in the art and has been described herein above. Accordingly, the term "activator of the BMP pathway" refers to an activator of any one of the above recited molecules that form part of this signalling pathway.

Preferably, the activator of the BMP signalling pathway is selected from the group consisting of BMP4 BMP2, BMP5, BMP6, BMP7, BMP8A, and BMP8B (Gene Symbols: BMP4, BMP2, BMP5, BMP6, BMP7, BMP8A, and BMP8B, respectively; Mazerbourg et al. (J Biol Chem (2005) 280:32122-32132. Most preferably, the activator of the BMP signalling pathway is BMP4.

Preferred amounts of BMP4 to be employed are between about 2 and about 100 ng/ml, more preferably between about 5 and about 20 ng/ml, and most preferably the amount is about 10 ng/ml. Preferred amounts of BMP2, BMP5, BMP6, BMP7, BMP8A, and BMP8B to be employed are also between about 2 and about 100 ng/ml, more preferably between about 5 and about 20 ng/ml, and most preferably the amount is about 10 ng/ml.

The term "neurotrophins", as used herein, relates to a family of proteins that regulate the survival, development, and function of neurons. Family-members include for example nerve growth factor (NGF), brain-derived neurotrophic factor (BDNF), neurotrophin-3 (NT-3), neurotrophin-4 (NT-4) as well as the GDNF family of ligands and ciliary neurotrophic factor (CNTF).

Accordingly, the term "at least two different neurotrophins" refers to two or more of the above recited molecules. Preferably, the at least two different neurotrophins are BDNF and GDNF (Gene Symbols: BDNF and GDNF, respectively; Jiang et al. (Chin Med J (Engl) (2011) 124: 1540-1544); Glavaski-Joksimovic et al. (J Neurosci res (2010) 88:2669-2681)).

Preferred amounts of BDNF and GDNF to be employed are between about 5 and about 50 ng/ml each, more preferably between about 7.5 and about 25 ng/ml each, and most preferably the amount is about 10 ng/ml each. BDNF and GDNF may for example be obtained from Peprotech.

All other definitions and preferred embodiments are as provided elsewhere herein.

In accordance with this embodiment of the invention, peripheral nervous system neurons are obtained. Such cells are particularly suitable to model, without being limiting, Hirschsprung's Disease, DiGeorge syndrome, Waardenburg syndrome, Charcot-Marie-tooth disease, familial disautonomia, congenital insensitivity to pain with anhidrosis and pediatric cancers, such as neuroblastoma, the treatment of such diseases by transplantion of the cells obtained by the method of this embodiment as well as their use for drug screening.

In another preferred embodiment of the present invention, the method further comprises culturing the NPBSCs obtained in step (d) in a neural medium, thereby differentiating the NPBSCs into central nervous system neurons.

As is shown in the appended examples, changing NPBSC expansion medium to a neural medium, such as e.g. N2B27 medium without additional supplements, results in differentiation of the NPBSC into central nervous system neurons of hindbrain character. Such cells find numerous applications, such as in drug discovery screens, for transplantations in order to treat diseases correlated with hindbrain pathology (e.g. Parkinson's disease) as well as for modelling such diseases.

In another preferred embodiment of the method of the invention, the method further comprises:
(i) culturing the NPBSCs obtained in step (d) in a neural medium comprising
  (a) an activator of the FGF signaling pathway,
  (b) an activator of the hedgehog signaling pathway and
  (c) an inhibitor of oxidation,
  for about 168 to about 192 hours;
(ii) changing the medium to a neural medium comprising
  (a) at least two different neurotrophins,
  (b) an inhibitor of oxidation;
  and culturing the cells for about 24 to about 96 hours; and
(iii) further culturing the cells in a neural medium comprising
  (a) at least two different neurotrophins; and
  (b) an inhibitor of oxidation;
thereby differentiating the NPBSCs into midbrain dopaminergic neurons.

The "FGF signaling pathway" is well known in the art and has been described, for example, in Dorey and Amaya (Development (2010) 137:3731-3742) and Omitz and Otoh (Genome Biol (2001) 2:REVIEWS3005). FGF ligands, including, for example, FGF1, FGF2, FGF3, FGF4, FGF5, FGF6, FGF7, FGF8, FGF9, FGF10, FGF11, FGF12, FGF13, FGF14, FGF16, FGF17, FGF18, FGF19, FGF20, FGF21, FGF22, and/or FGF23, induce dimerization upon binding to a receptor, including, for example, FGFR1, FGFR2, FGFR3, and/or FGFR4, causing a signal to be transduced to proteins including, for example, SRC, FRS2, GRB2, SHP2, SOS, RAS, cRAF, MEK, ERK, GAB1, GAB2, PI3K, PKB, PLCgamma, PKC, and/or CAMKII.

Accordingly, the term "activator of the FGF signaling pathway" refers to an activator of any one of the above recited molecules that form part of this signalling pathway.

Preferably, the activator of the FGF signaling pathway is selected from the group consisting of FGF2, FGF1, FGF4, FGF8, FGF17 and FGF18 (Gene Symbols: FGF2, FGF1, FGF4, FGF8, FGF17 and FGF18, respectively; Omitz and Otoh (Genome Biol (2001) 2:REVIEWS3005)). Most preferably, the activator of the FGF signalling pathway is FGF8.

Preferred amounts of FGF2, FGF1, FGF4, FGF8, FGF17, or FGF18 to be employed are between about 1 and about 500 ng/ml, more preferably between about 10 and about 250 ng/ml, and most preferably the amount is about 100 ng/ml.

All other definitions and preferred embodiments are as provided elsewhere herein.

In accordance with this embodiment of the invention, midbrain dopaminergic neurons are obtained. Such cells are particularly suitable to model Parkinson's disease, conduct drug discovery screens, or treat Parkinson's disease.

In a more preferred embodiment of this method of the invention of differentiating the NPBSCs into midbrain dopaminergic neurons, the medium in step (ii) further comprises:
(c) an activator of the activin/TGF-β signalling pathway; and/or
(d) an activator of adenylate cyclase or a cAMP analogue; and/or
(e) an activator of the hedgehog signaling pathway.

The "activin/TGF-β signalling pathway" is well known in the art and has been described herein above.

Accordingly, the term "activator of activin/TGF-β signalling pathway" refers to an activator of any one of the above recited molecules that form part of this signalling pathway.

Preferably, the activator of activin/TGF-β signalling pathway is selected from the group consisting of TGFB1, TGFB2, TGFB3, ACTIVIN A, ACTIVIN B, ACTIVIN AB, and/or NODAL (Gene Symbols: TGFB1, TGFB2, TGFB3, ACTIVIN A, ACTIVIN B, ACTIVIN AB, and NODAL, respectively; Xin-Hua Feng and Rik Derynck (Annu. Rev. Cell Dev. (2005) 21:659-693)). Most preferably, the activator of the activator of activin/TGF-β signalling pathway is activator of TGFB3.

Preferred amounts of TGFB1, TGFB2, TGFB3, ACTIVIN A, ACTIVIN B, ACTIVIN AB, and/or NODAL to be employed are between about 0.5 and about 100 ng/ml, more preferably between about 0.75 and about 10 ng/ml, and most preferably the amount is about 1 ng/ml.

Preferred examples of an "activator of adenylate cyclase or a cAMP analogue" include, without being limiting, 8-Piperidinoadenosine 3',5'-monophosphate (Skalhegg, B. S., et al., J. Biol. Chem. 267, 15707-15714, (1992)), 8-(6-Amino-hexyl)aminoadenosine 3':5'-cyclic monophosphate (Whitehouse, B. J. and Abayasekara, D. R.; J. Mol. Endocrinol. 12, 195-202, (1994)), Sp-Adenosine 3',5'-cyclic monophosphorothioate (Scholubbers, et al. Eur. J. Biochem. 138, 101-109, (1984), $N^6$-Benzoyladenosine-3',5'-cyclic monophosphate (Christensen, A. E., et al. J. Biol. Chem. 278, 35394-35402, (2003)), 8-Chloroadenosine-3',5'-cyclic monophosphorothioate (Yokozaki, H. Cancer Res. 52, 2504, (1992)), Rp-isomer, 8-Bromoadenosine 3',5'-cyclic monophosphate (Meyer, R. B. Jr., and Miller, J. P., Life Sci. 14, 1019-1040, (1974)), 8-(6-Aminohexyl)aminoadenosine-3',5'-cyclic monophosphate (Skalhegg, B. S., et al. J. Biol. Chem. 267, 15707-15714, (1992)), 8-Chloroadenosine 3',5'-cyclic-monophosphate (Juranic, et al., J. Exp. Clin. Cancer Res 17, 269-275, (1998)), 8-(4-Chlorophenylthio)-2'-O-methyladenosine 3',5'-cyclic monophosphate (Enserink, J. M., et al., Nat. Cell Biol. 4, 901-906, (2002)), $N^6$,2'-O-Dibutyryladenosine 3',5'-cyclic monophosphate (dbcAMP; Hei, Y. J., et al., Mol. Pharmacol. 39, 233, (1991)), (3R,4aR,5S,6S,6aS,10S,10aR,10bS)-6,10,10b-trihydroxy-3,4a,7,7,10a-pentamethyl-1-oxo-3-vinyldodecahydro-1H-benzo[f] chromen-5-yl acetate (forskolin; Seamon et al., Proc Natl Acad Sci USA (1981) 78:3363-3367)). Most preferably, the cAMP analogue is dbcAMP.

Preferred amounts of 8-Piperidinoadenosine 3',5'-monophosphate, 8-(6-Aminohexyl)aminoadenosine 3':5'-cyclic monophosphate, Sp-Adenosine 3',5'-cyclic monophosphorothioate, $N^6$-Benzoyladenosine-3',5'-cyclic monophosphate, 8-Chloroadenosine-3',5'-cyclic monophosphorothioate, Rp-isomer, 8-Bromoadenosine 3',5'-cyclic monophosphate, 8-(6-Aminohexyl)aminoadenosine-3',5'-cyclic monophosphate, 8-Chloroadenosine 3',5'-cyclic-monophosphate, 8-(4-Chlorophenylthio)-2'-O-methyladenosine 3',5'-cyclic monophosphate, dbcAMP to be employed are between about 1 and about 1000 μM, more preferably between about 100 and about 750 μM, and most preferably the amount is about 500 μM. Preferred amounts of forskolin to be employed are between about 0.5 and about 100 μM, more preferably between about 1 and about 20 μM, and most preferably the amount is about 10 μM.

Most preferably, all three compounds recited in (c) to (e) are additionally present in the medium in step (ii).

In a further more preferred embodiment of this method of the invention of differentiating the NPBSCs into midbrain dopaminergic neurons, the medium in step (iii) further comprises:

(c) an activator of the activin/TGF-β signalling pathway; and/or (d) an activator of adenylate cyclase or a cAMP analogue.

Most preferably, both compounds recited in (c) and (d) are additionally present in the medium in step (iii). Even more preferably, all three compounds recited in (c) to (e) above are additionally present in the medium in step (ii) and both compounds recited in (c) and (d) are additionally present in the medium in step (iii).

In another preferred embodiment of the method of the invention, the method further comprises:

(i) culturing the NPBSCs obtained in step (d) in a neural medium comprising an activator of the hedgehog signalling pathway for about 24 to about 48 hours;

(ii) adding retinoic acid to the culture of step (i) for about 168 to about 192 hours; and (iii) further culturing the cells in a neural medium comprising at least two different neurotrophins, thereby differentiating the NPBSCs into motor neurons.

The term "retinoic acid" as used herein, refers to (2E,4E,6E,8E)-3,7-dimehyl-9-(2,6,6-trimethylcyclohexen-1-yl) nona-2,4,6,8-tetraenoic acid, which is also known as all-trans retinoic acid, and is well known in the art and has been described, for example, in Tang and Gudas, Annu. Rev. Pathol. Mech. Dis. (2011) 6:345-364.

Preferred amounts of retinoic acid to be employed are between about 0.1 to about 20 μM, more preferably between about 0.5 and about 5 μM, and most preferably the amount is about 1 μM. Retinoic acid may be obtained from e.g. Sigma.

All other definitions and preferred embodiments are as provided elsewhere herein.

In accordance with this embodiment of the invention, motor neurons are obtained. Such cells find numerous applications, for example in the generation of disease models of motor neuron disorders, the treatment of such diseases by transplantion of the cells obtained by the method of this embodiment as well as their use for drug screening.

In a more preferred embodiment of this method of the invention of differentiating the NPBSCs into motor neurons, the medium in step (iii) further comprises:

(c) an activator of adenylate cyclase or a cAMP analogue.

In another preferred embodiment of the method of the invention, the method further comprises:

(i) culturing the NPBSCs obtained in step (d) in a neural medium comprising an activator of the canonical WNT signalling pathway for about 48 to 72 hours; and (ii) culturing the cells obtained in step (i) in cell culture medium comprising serum, thereby differentiating the NPBSCs into neural crest—derived mesenchymal cells.

The term "cell culture medium", as used in accordance with this embodiment, refers to any commonly used cell culture medium known in the art, preferably a medium selected from the group consisting of DMEM, knock-out DMEM, F-10, F-12, RPMI medium 1640, MEM, IMEM, GMEM and DMEM/F12. Preferably, the serum is selected from fetal calf serum (FCS) and fetal bovine serum (FBS).

Preferred amounts of serum to be employed are between about 1% and about 50%, more preferably between about 5 and about 25%, and most preferably the amount is about 10%. Serum such as for example FCS may be obtained from e.g. PAA.

In accordance with this embodiment of the invention, neural crest-derived mesenchymal cells are obtained. Neural crest-derived mesenchymal cells emerge during development in the area between the neural and non-neural ectoderm. These cells migrate extensively and give rise to a variety of different cell types, such as peripheral neurons, glia, melanocytes, and endocrine cells, being able to from smooth muscle, bone and cartilage, without being limiting. Neural crest-derived mesenchymal cells are characterized by the expression of specific markers, including, without being limiting, SNAI2, PAX7, SOX9 and HNK-1. Neural crest-derived mesenchymal cells can be used for drug screening as well as modelling or therapeutic treatment of neural crest-associated diseases. Well-investigated examples of these diseases comprise, without being limiting, Hirschsprung's Disease, DiGeorge syndrome, Waardenburg syndrome, Charcot-Marie-tooth disease, familial disautonomia, congenital insensitivity to pain with anhidrosis and pediatric cancers, such as neuroblastoma, as described herein below. These applications and further characterizations of these cells are well-described in the art, such as in Lee and others, Nat. Protocols. (2010) 5:688-701.

In accordance with the present invention, "SNAI2" refers to the zinc-finger protein snail homolog 2, also known as human SLUG, a protein that in humans is encoded by the SNAI2 gene. SNAI2 is a transcriptional regulator. Human SNAI2 is represented by the NCBI reference NP_003059.1 and has been described in the art, for example in Cohen et al. (1998). Genomics 51 (3): 468-71.

In accordance with the present invention, "PAX7" refers to Paired box protein 7, a protein that in humans is encoded by the PAX7 gene. PAX7 is a transcriptional regulator. Human PAX7 is represented by the NCBI reference NP_002575 and has been described in the art, for example in Stapleton et al. (1995). Nat Genet 3 (4): 292-298.

In accordance with the present invention, "SOX9" refers to SRY (sex determining region Y)-box 9, a protein that in humans is encoded by the SOX9 gene. SOX9 is a transcriptional regulator. Human SOX9 is represented by the NCBI reference NP_000337.1 and has been described in the art, for example in Tommerup et al. (1993). Nat Genet 4 (2): 170-4.

In accordance with the present invention, "HNK-1" refers to an epitope detected by a monoclonal antibody designated HNK-1 and has been described in the art, for example in Lipinski et al. (1983), J Exp Med 158:1775-1780.

In another preferred embodiment, the method of the present invention further comprises
(i) culturing the NPBSCs obtained in step (d) in a neural medium comprising an activator of FGF signalling for about 12 to 96 hours; and
(ii) culturing the cells obtained in step (i) in cell culture medium comprising fetal calf serum, fetal bovine serum and/or CNTF for about 14 to 60 days;
thereby differentiating the NPBSCs into astrocytes.

The term "CNTF" refers to "ciliary neurotrophic factor", which is a protein that in humans is encoded by the CNTF gene (Gene Symbol: CNTF; Protein sequence: NP_000605.1) and has been described in the art, e.g. in Dutt et al., In Vitro Cell Dev Biol Anim (2010) 46:635-646.

Preferred amounts of CNTF to be employed are between about 1 and about 500 ng/ml, more preferably between about 5 and about 50 ng/ml, and most preferably the amount is about 10 ng/ml.

All other definitions and preferred embodiments are as provided elsewhere herein.

In accordance with this embodiment of the invention, astrocytes are obtained. Such cells find numerous applications, for example in the generation of disease models of neuralogical disorders, the treatment of such diseases by transplantion of the cells obtained by the method of this embodiment as well as their use for drug screening.

In another preferred embodiment, the method of the present invention further comprises culturing the NPBSCs obtained in step (d) in a neural medium comprising an activator of FGF signalling for about 12 to 96 hours; thereby differentiating the NPBSCs into neural rosette cells.

All definitions and preferred embodiments are as provided elsewhere herein.

In accordance with this embodiment of the invention, neural rosette cells are obtained. Such cells are well known in the art and have been described, e.g. in Zhang et al., Nat Biotechnol 19, 1129-1133 and Koch et al., Proc Natl Acad Sci USA 106, 3225-3230. Such cells find numerous applications, for example in the generation of disease models of neurological disorders, the treatment of such diseases by transplantion of the cells obtained by the method of this embodiment as well sa their use for drug screening.

In another preferred embodiment of the method of the present invention, the cells obtained are free or substantially free of pathogens.

Pathogens to be avoided are well known to the skilled person and include, without being limiting, viruses such as for example Hepatitis virus A, B, C, Epstein-Barr-Virus or HIV-Virus and bacteria such as for example mycoplasm or chlamydia.

The present invention also relates to neural plate border stem cells obtained or obtainable by the method of the invention.

To the inventors best knowledge, such cells do not occur naturally at any point in development. As shown in the example sections, the NPBSCs derived by the method of the present invention express the markers PAX6 and SOX1, which occur in vivo only after neural tube closure and the onset of somitogenesis. Accordingly, the NPBSCs have features of neural tube stage progenitors. In addition, NPBSCs express PHOX2B, HOXA2, and HOXB2. This profile is indicative of motor neuron progenitors in the hindbrain (approximately at the level of rhombomere 4). As is shown in the appended examples, motor neurons form efficiently from the NPBSCs of the invention. In addition, NPBSCs also express MSX1 and IRX3, which are not expressed by motor neuron progenitors. Instead, MSX1 and IRX3 are markers of neural crest and dorsal progenitors, respectively. In agreement with this, the present inventors have shown that NPBSCs also efficiently form peripheral neurons, which are neural crest derivatives. In summary, NPBSCs express a combination of markers that is not found during development. This unique combination of markers is reflected by the unique developmental potential of NPBSCs, which is not comparable to any cells of the neural tube.

The present invention further relates to the neural plate border stem cells of the invention for use in medicine or medical/pharmaceutical research.

The cells of the invention as well as a composition comprising the neural plate border stem cells of the can be used in a variety of experimental as well as therapeutic scenarios. The cells of the invention have no transgenic expression elements and are more differentiated than pluripotent or totipotent stem cells. Accordingly, there is an overall reduced risk of these cells developing into cancerous cells, which renders them particularly beneficial in gene therapy, regenerative medicine, cell therapy or drug screening.

Gene therapy, which is based on introducing therapeutic DNA constructs for correcting a genetic defect into germ line cells by ex vivo or in vivo techniques, is one of the most important applications of gene transfer. Suitable vectors and methods for in vitro or in vivo gene therapy are described in the literature and are known to the person skilled in the art (Davis P B, Cooper M J., AAPS J. (2007), 19; 9 (1):E11-7; Li S, Ma Z., Curr Gene Ther. (2001),1 (2):201-26). In accordance with the invention, pluripotent stem cells obtained from a patient could, for example, be genetically corrected by methods known in the art and subsequently be reprogrammed into neural plate border stem cells having the ability to differentiate into neural tube or neural crest cell derivatives, including, for example, CNS or PNS neurons, respectively. This evidences the applicability of the NPBSCs in gene therapy and/or cell therapy.

Regenerative medicine can be used to potentially cure any disease that results from malfunctioning, damaged or failing tissue by either regenerating the damaged tissues in vivo or by growing the tissues and organs in vitro and subsequently implanting them into the patient. The NPBSCs of the invention being capable of differentiating into neural tube or neural crest cell derivatives, including, for example, CNS or PNS neurons, respectively, that can be used in neurobiological aspects of regenerative medicine and hence drastically reduce the need for ES cells.

The neural plate border stem cells of the invention can also be used to identify drug targets and test potential therapeutics hence reducing the need for ES cells and in vivo studies. Experimental setups and methods to identify and/or assess effects of a potential drug including, for example, target-site and -specificity, toxicity or bioavailability are well-known to the person skilled in the art. Further, the neural plate border stem cells may be used to study the prevention and treatment of birth defects or study cell differentiation. Finally, the neural plate border stem cells of the invention may also be useful in experimental settings—besides therapeutic applications—to study a variety of aspects related to neuronal differentiation. The neural plate border stem cells can further be subject to studies relating to, e.g., gene therapy, gene targeting, differentiation studies, tests for safety and efficacy of drugs, transplantation of autologous or allogeneic regenerated tissue, tissue repair, diseases like, e.g., Parkinson's disease, amyotrophic lateral sclerosis, spinal muscular atrophy, peripheral neuropathy and Charcot-Marie-Tooth disease, embryonal gene expression, genetic manipulation of embryonal genes, early embryology and fetal development, identification of embryonic cell markers, cell migration or apoptosis.

In a more preferred embodiment, the neural plate border stem cells of the invention are for use in the treatment of a disease selected from the group consisting of Parkinson's disease, amyotrophic lateral sclerosis, spinal muscular atrophy, peripheral neuropathy, Hirschsprung's disease, DiGeorge syndrome, familial dysautonomia, congenital insensitivity to pain with anhididrosis and Charcot-Marie-Tooth disease. These diseases are well known in the art and have been described, e.g. in Davie, Br Med Bull (2008) 86:109-127 (Parkinson's disease), Ilieva et al., J Cell Biol (2009) 187:761-772 (amyotrophic lateral sclerosis), Burghes et al., Nat Rev Neuroscience (2009) 10:597-609 (spinal muscular atrophy), Hughes, B M J (2002) 342:466-469 (peripheral neuropathy), Guiguis, Can Fam Physician. (1986) 32: 1521-1523 (Hirschsprung's disease), Greenberg, J Med Genet. (1993) 30: 803-806 (DiGeorge syndrome), Gold-von Simson et al., J Pediatr (2009) 155:934-936 (familial dysautonomia), Mardy et al., Am J Hum Genet (1999) 64:1570-1579 (congenital insensitivity to pain with anhididrosis) and Pareyson and Marchesi The Lancet Neurology (2009) 8:654-667 (Charcot-Marie-Tooth disease).

All the steps recited in the embodiments of the present invention are carried out in the order listed and subsequently to each other, unless defined otherwise.

Unless otherwise defined, all technical and scientific terms used herein have the same meaning as commonly understood by one of ordinary skill in the art to which this invention belongs. In case of conflict, the patent specification, including definitions, will prevail.

The figures show:

FIG. 1. Early temporal window of competence for hedgehog induced specification of ventral neural tube progenitors. qRT-PCR analysis for the ventral markers NKX6.1 (A) and OLIG2 (B) on differentiating EBs treated with PMA beginning on the indicated day. Error bars are the variation of the mean from one human ESC line and one human iPSC line.

Figure 2:
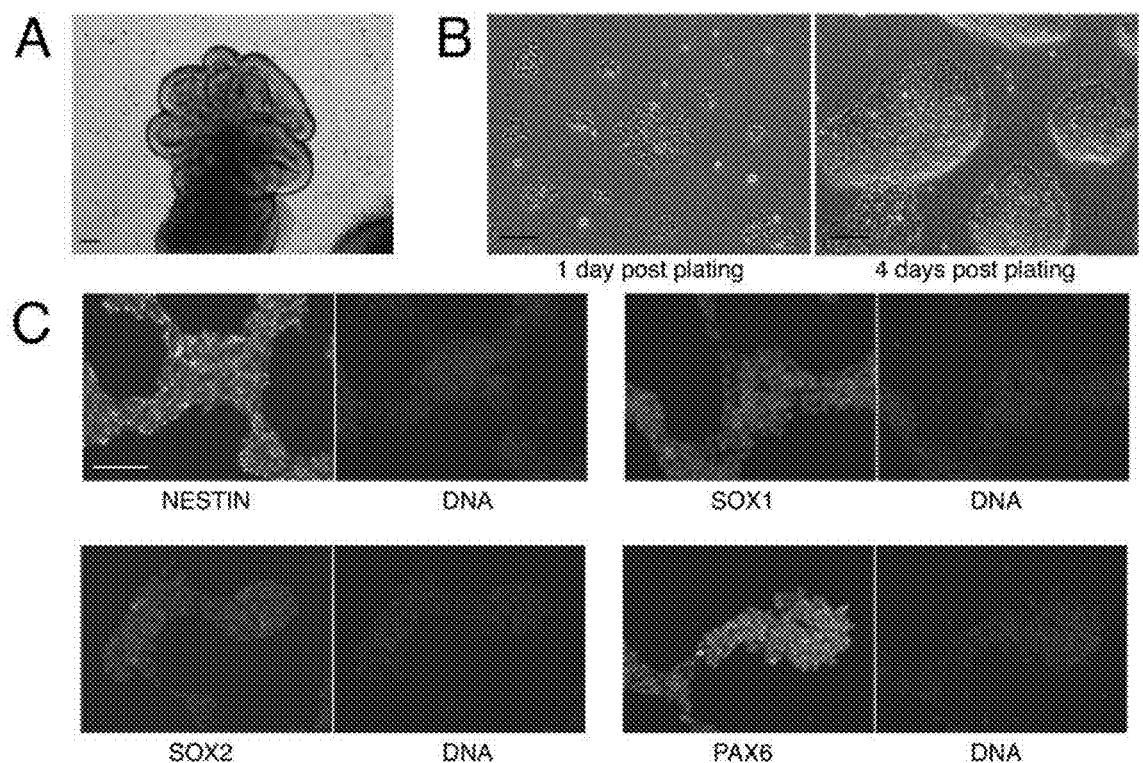

FIG. 2. Derivation of NPBSCs. (A) Plated EBs differentiated in the presence of both PMA and CHIR for 6 days. (B) Phase contrast images of NPBSCs on the indicated days after splitting. (C) Immunostaining of hESC-derived NPBSCs with antibodies raised against the indicated neural progenitor markers. Nuclei are counterstained with Hoechst. Scale bars are 100 μm.

Figure 3:
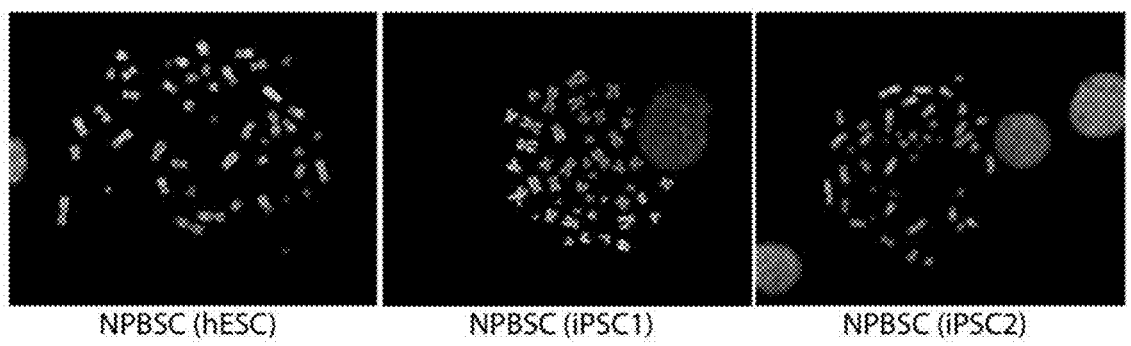

FIG. 3. NPBSCs have a stable diploid karyotype. DAPI stained metaphase spread analysis for 3 independent NPBSC lines derived from either human ESCs or iPSCs as indicated, analyzed at passage 25 and showing a diploid karyotype of 46 chromosomes.

Figure 4:
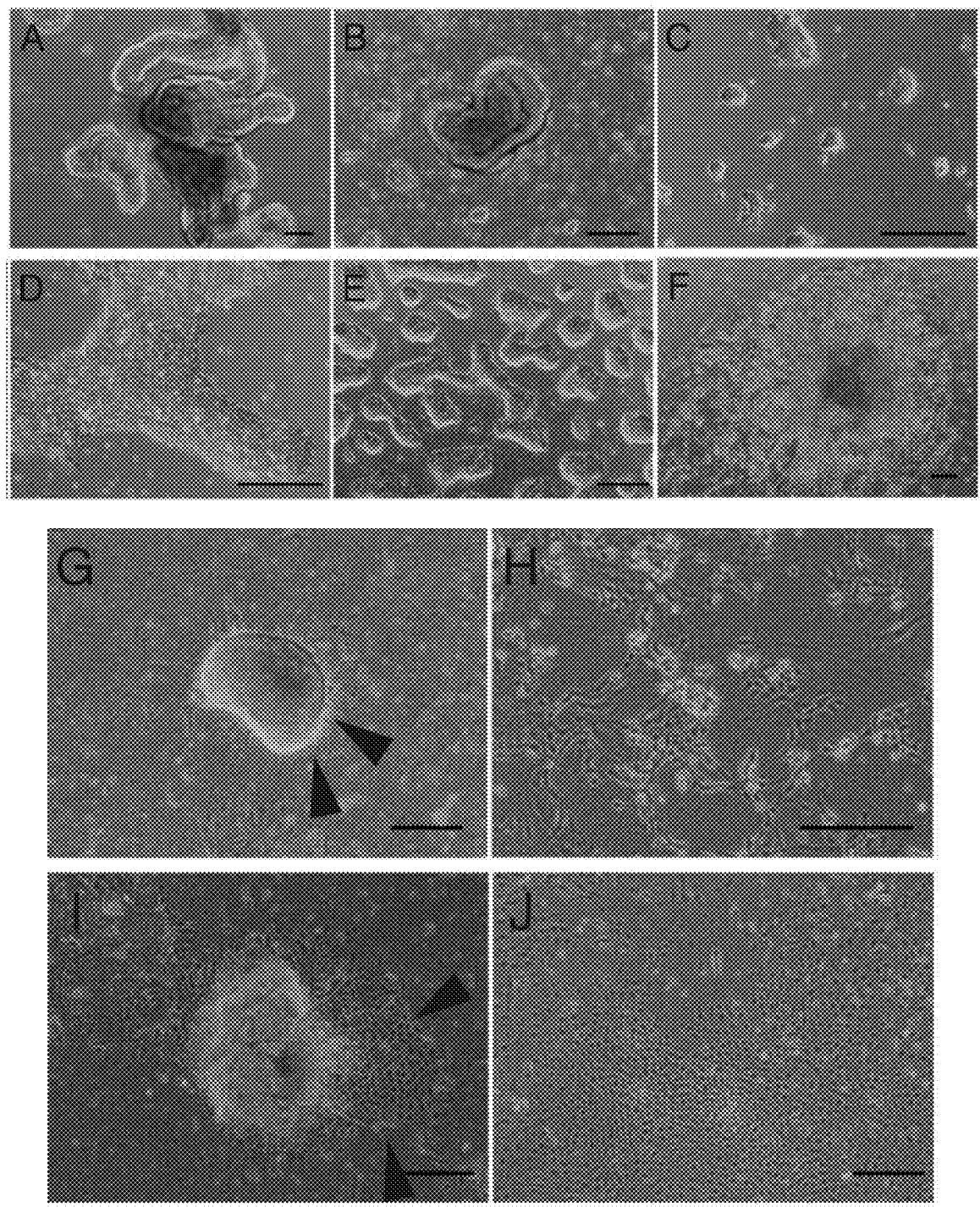
Figure 4:
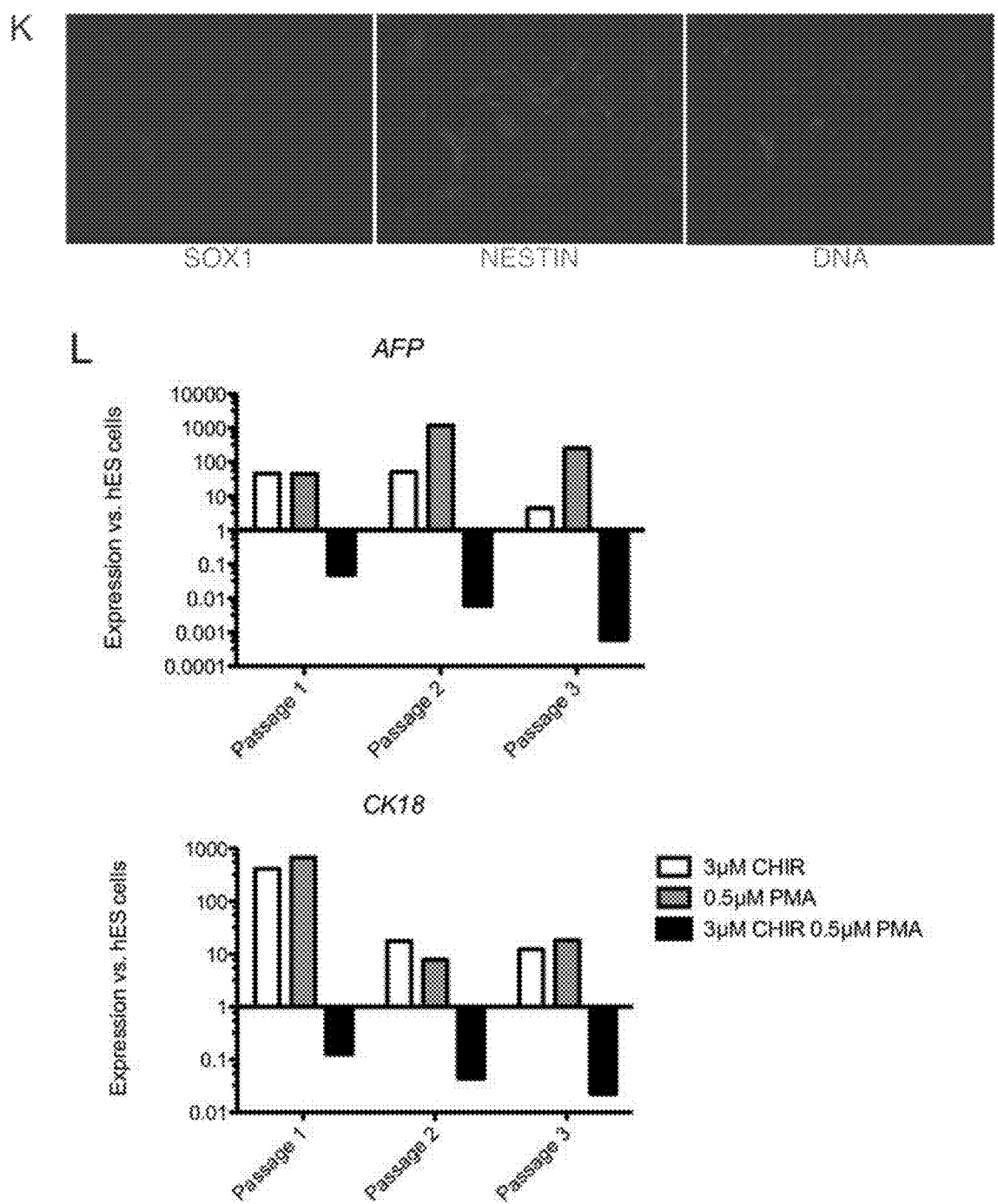

FIG. 4. EB formation enables NPBSC derivation efficiency. (A) EBs at day 6 of NPBSC derivation show massive outgrowth of neuroepithelial cells. (B) Disaggregated EBs plated on matrigel-coated dishes prior to first splitting. (C) NPBSC colonies 1 day after the first splitting already showing that most cells present in the cultures are neural cells. (D) Confluent NPBSC culture 6 days after first splitting. (E) Four passages already yield very homogenous NPBSC cultures. (F) When treated as a monolayer with NPBSC derivation conditions, no epithelial outgrowth was observed at day five of differentiation. (G) When treated with PMA only, plated EBs already show intensive neurite formation, marked by arrowheads, more clearly visible after the first split, shown in (H). (I) Derivation of NPBSC with only CHIR produced many non-neural cells that overgrew the culture (J) and that were negative for the neural markers SOX1 and NESTIN (K). (L) qRT-PCR analysis for the indicated markers of non-neural differentiation on EBs treated with the indicated small molecules. Only the combination of CHIR and PMA together resulted in efficient formation of homogenous NPBSC cultures and inhibited formation of non-neural cells. Scale bars are 100 μm.

Figure 5:
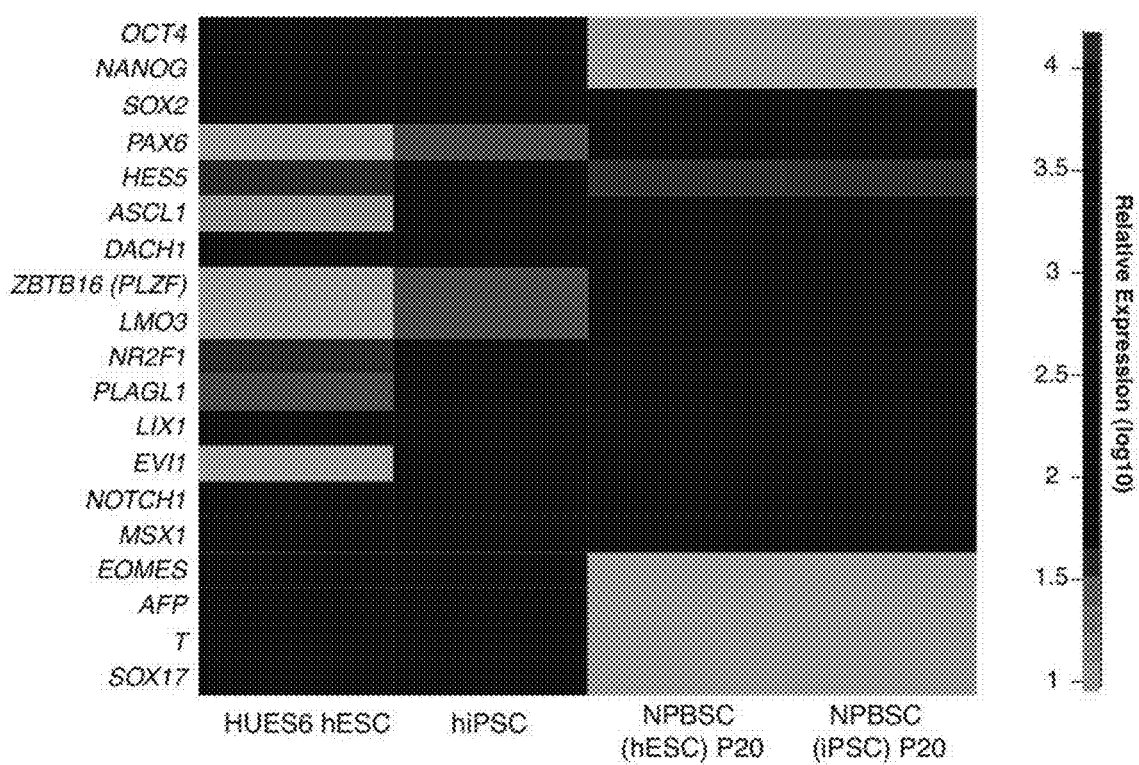

FIG. 5. Microarray analysis of NPBSC. Expression levels for the indicated genes derived from microarray analysis of two NPBSC lines and their parental human pluripotent cell lines. NPBSCs consistently expressed neural progenitor and rosette markers, but not markers of pluripotency or mesendodermal differentiation.

Figure 6:
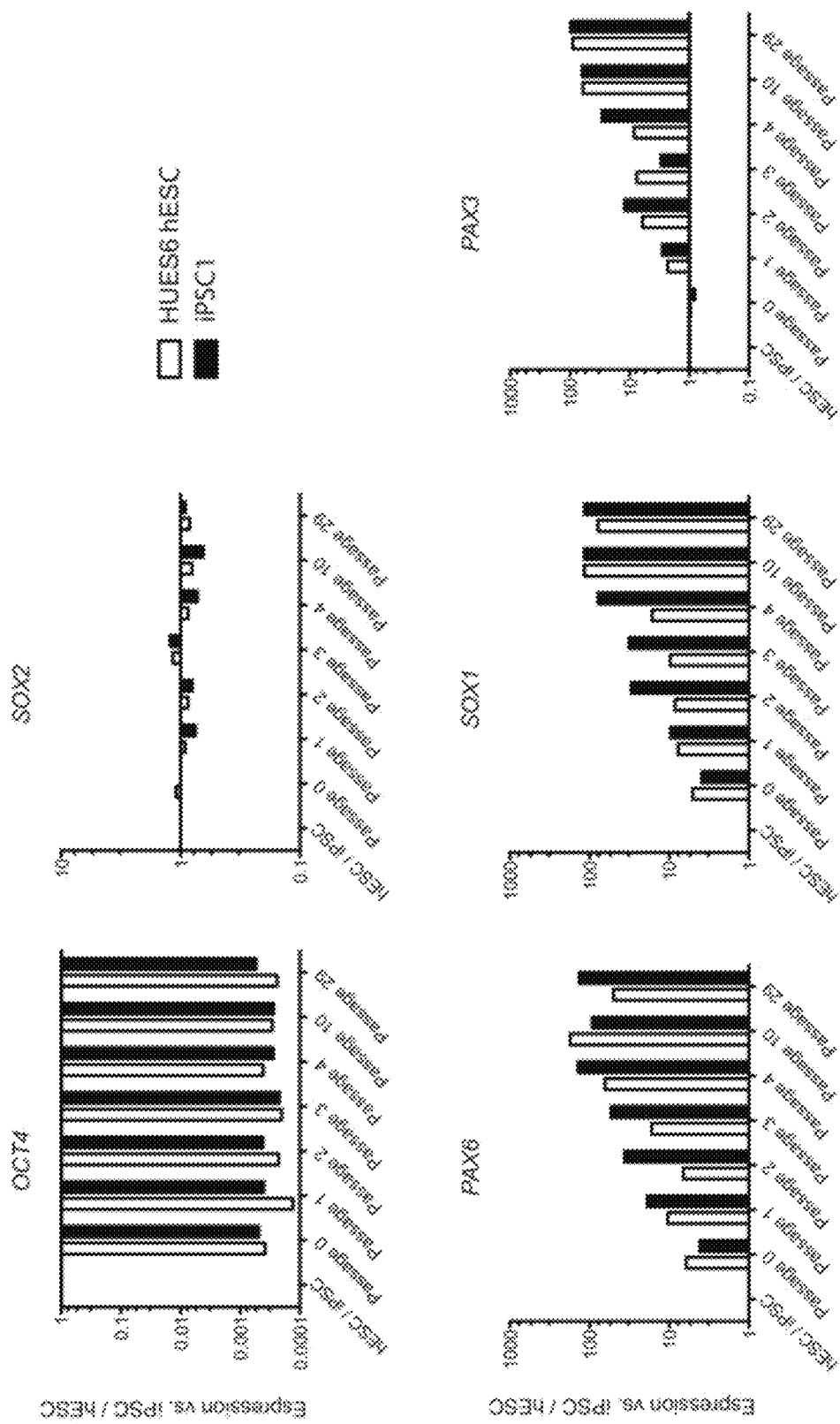
Figure 6:
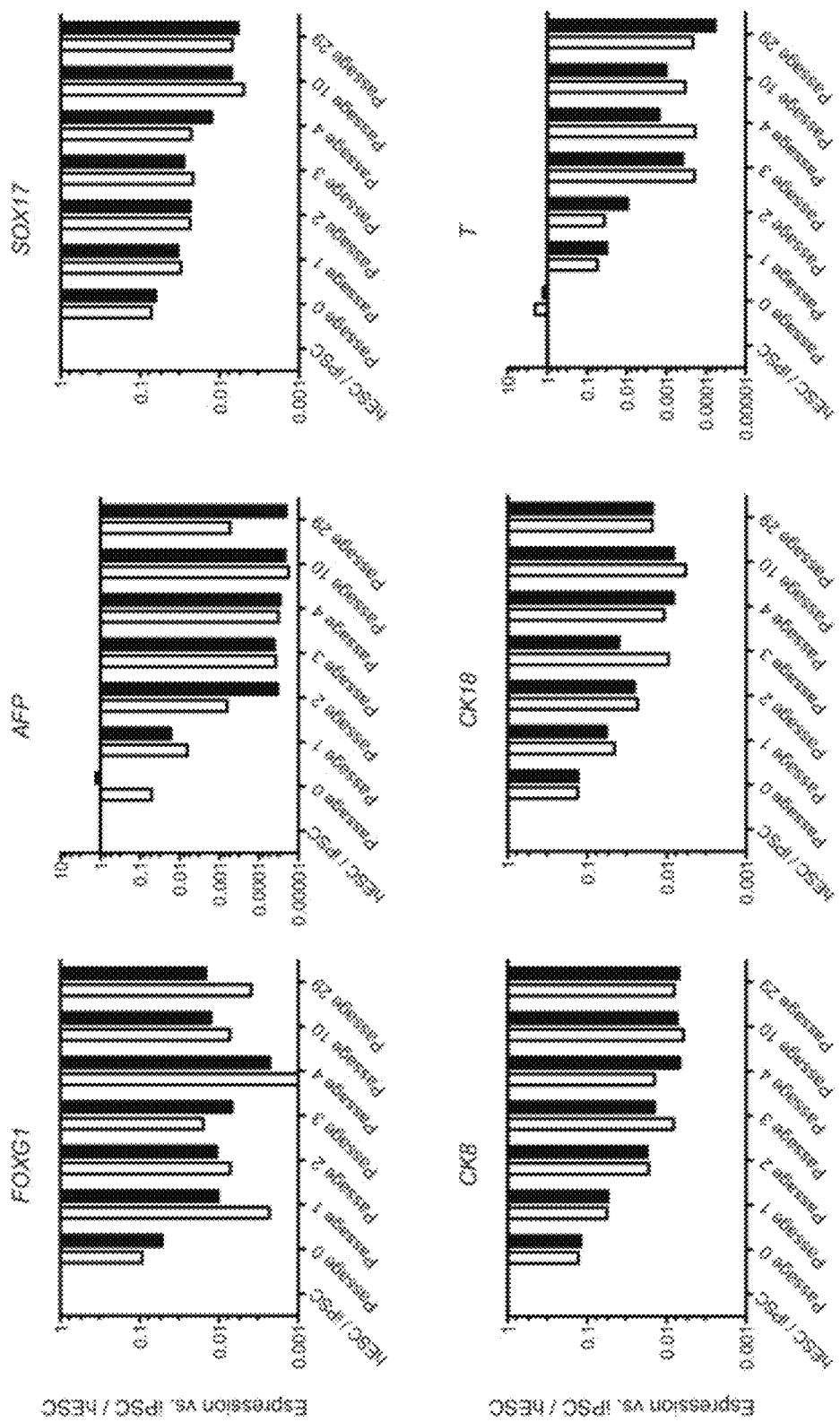

FIG. 6. NPBSCs adopt a stable identity of regionally specified neural progenitors after four passages.

qRT-PCR analysis of 2 indicated NPBSC line at the indicated passage number for the indicated gene. OCT4, SOX2=pluripotency markers. SOX2, SOX1, PAX6=neural progenitor markers. PAX3=neural plate marker. FOXG1=anterior neural progenitor marker. AFP, SOX17=endodermal markers. T, CK8, CK18=mesodermal marker.

Figure 7:
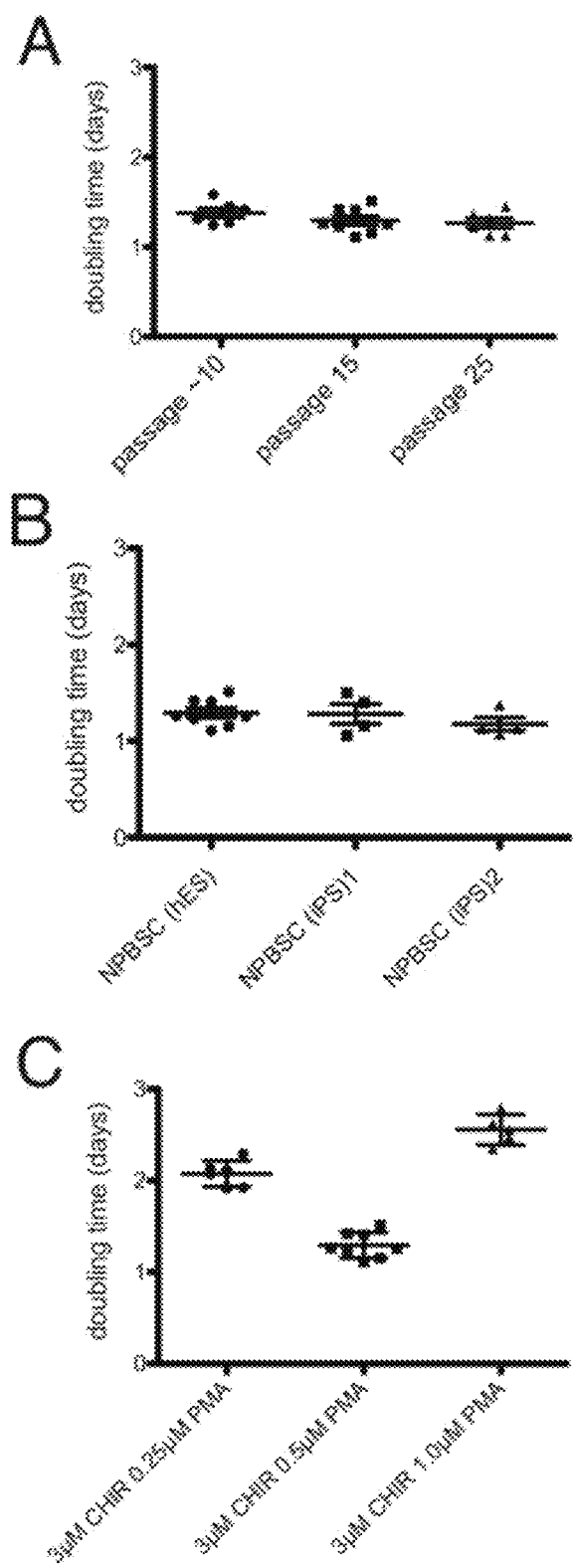

FIG. 7. NPBSC show a stable growth rate over extended passaging. (A) Doubling time of NPBSCs derived from hESCs is stable over multiple passages. (B) Doubing time of NPBSCs from different human pluripotent cell lines have comparable doubling times. (C) 0.5 µM is the preferred PMA concentration for NPBSC growth. When grown with 0.25 µM or 1 µM PMA concentrations, the doubling time was higher.

Figure 8:
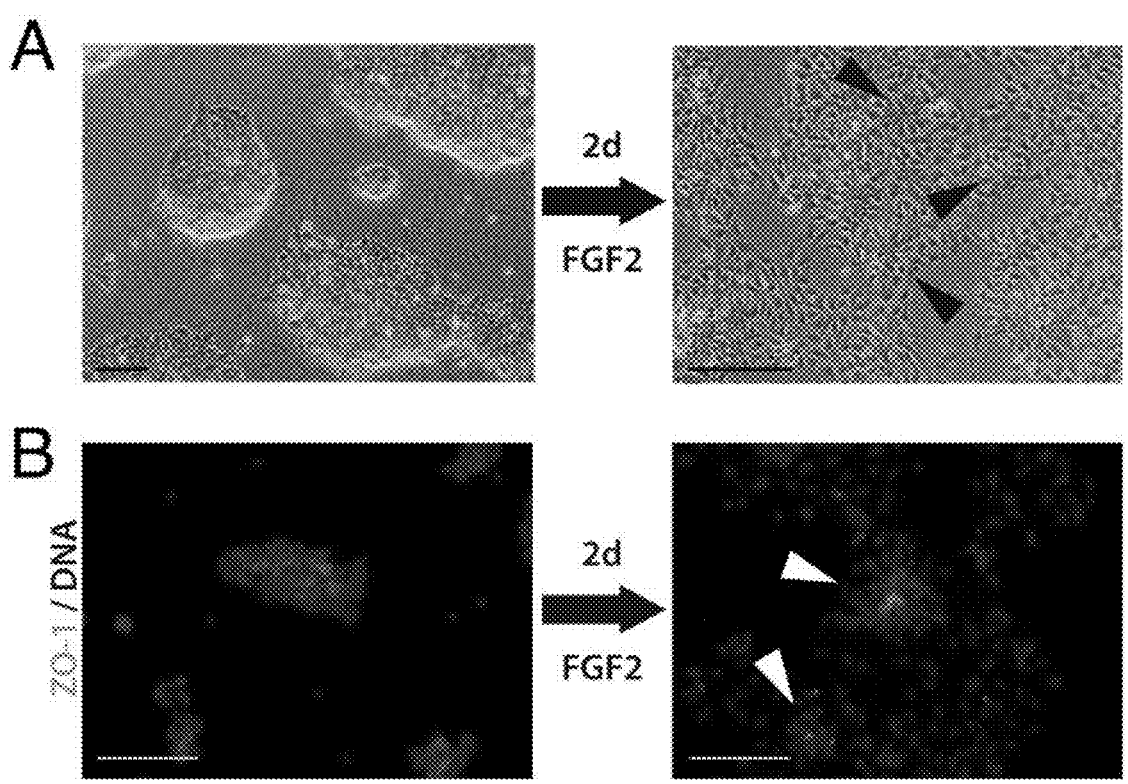

FIG. 8. NPBSCs are capable of forming neural rosettes. (A) Phase contrast image of NPBSCs before and after treatment with FGF2 for 2 days. (B) Immunostaining for ZO-1 on NPBSCs before and after treatment with FGF2. Arrowheads indicate ZO-1 expression in the center of neural rosettes, in contrast to the diffuse expression in NPBSCs. Scale bars are 100 µm.

Figure 9:
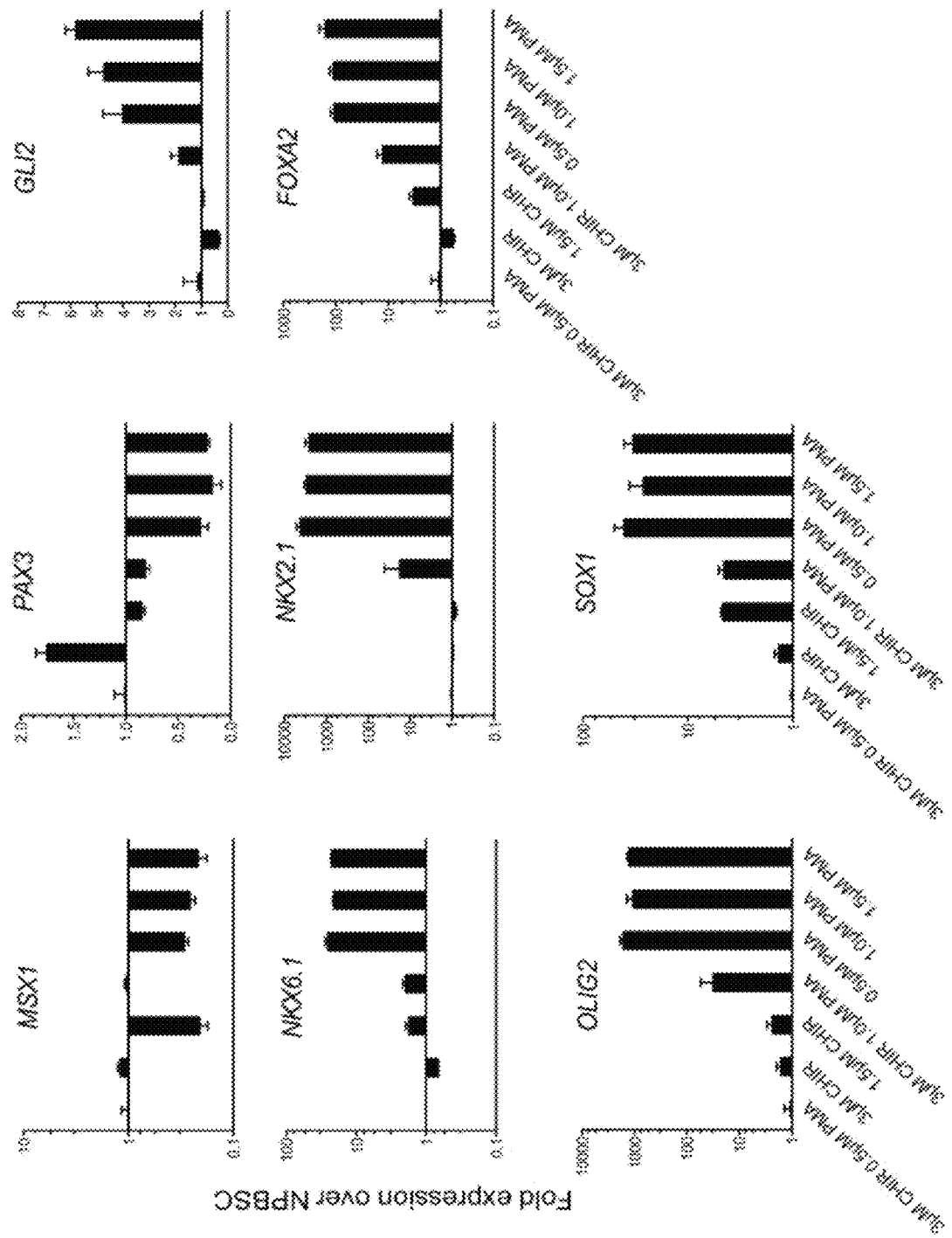
Figure 9:
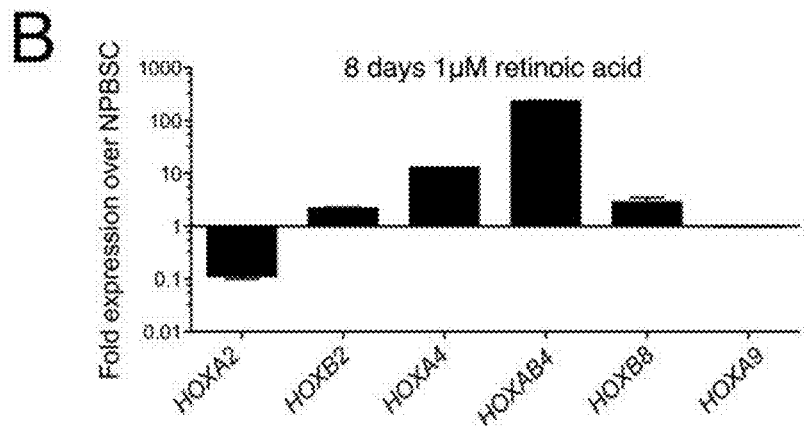

FIG. 9. NPBSCs can be respecified along both the dorsoventral and rostrocaudal axes. (A) qRT-PCR analysis for the indicated marker on NPBSCs cultured under the indicated conditions for 6 days. Error bars represent the standard deviation from three independent cultures. (B) qRT-PCR analysis for the indicated rostrocaudal marker on NPBSCs cultured with 1 µM RA for 8 days. Error bars represent the variation from two independent cultures.

Figure 10:
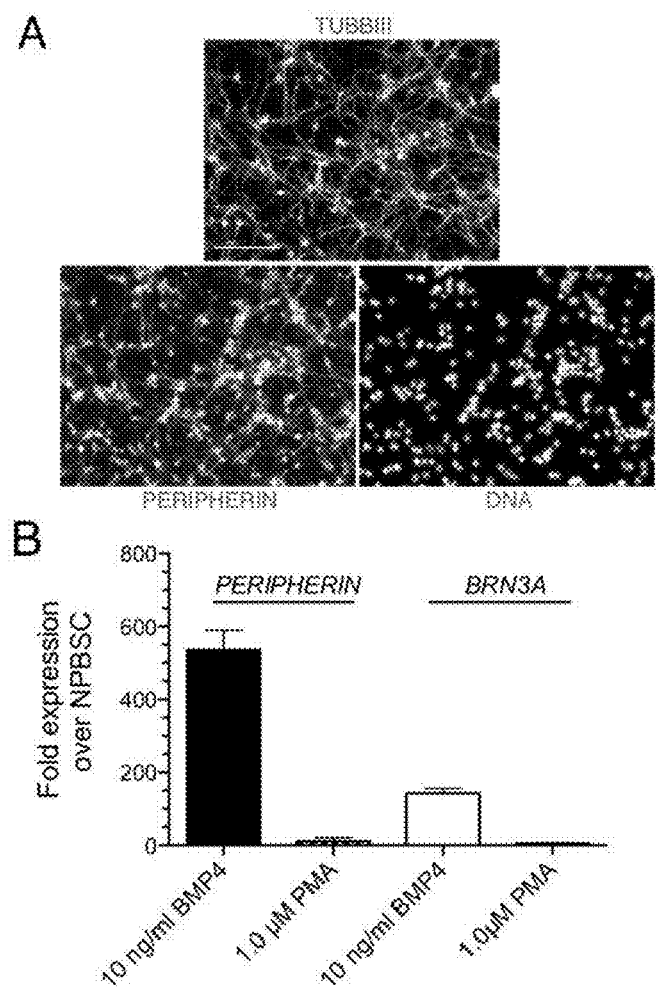
Figure 10:
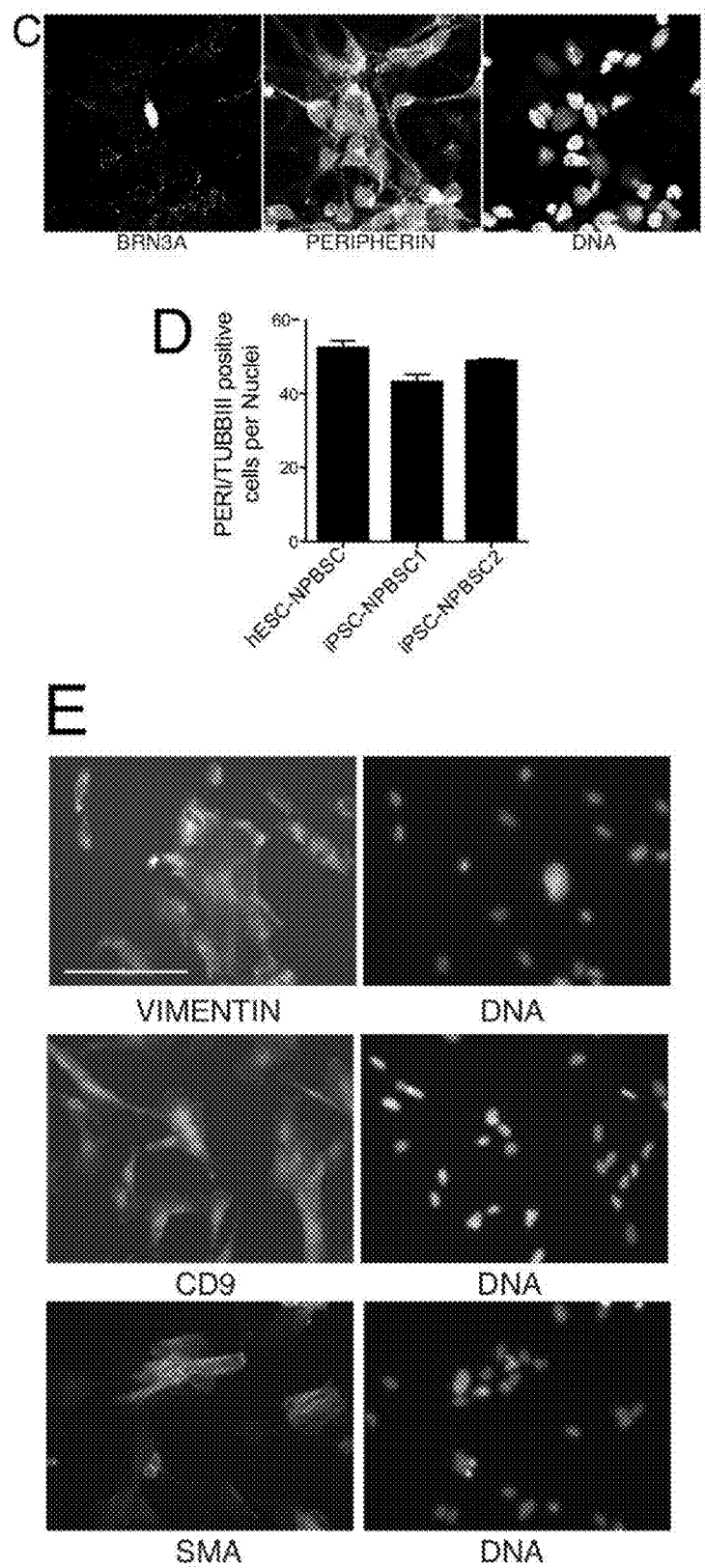

FIG. 10. Differentiation of PNS neurons and mesenchymal cells from NPBSCs. (A) Immunostaining for PERIPHERIN and TUBBIII of hESC-derived NPBSCs differentiated in the presence of BMP4. Nuclei are stained with Hoechst. (B) qRT-PCR demonstrating upregulation of PERIPHERIN and BRN3A in NPBSCs differentiated for 8 days in the presence of BMP4, but not PMA. (C) Confocal imaging demonstrating BRN3A and PERIPHERIN double positive peripheral neurons. (D) More than 40% of cells are double positive for PERIPHERIN and TUBBIII after patterning with BMP4. Error bars represent variation from two independent cultures. (E) Immunostaining of VIMENTIN, CD9 and SMA positive mesenchymal cells differentiated from NPBSCs treated with fetal calf serum. Scale bars are 100 µm.

Figure 11:
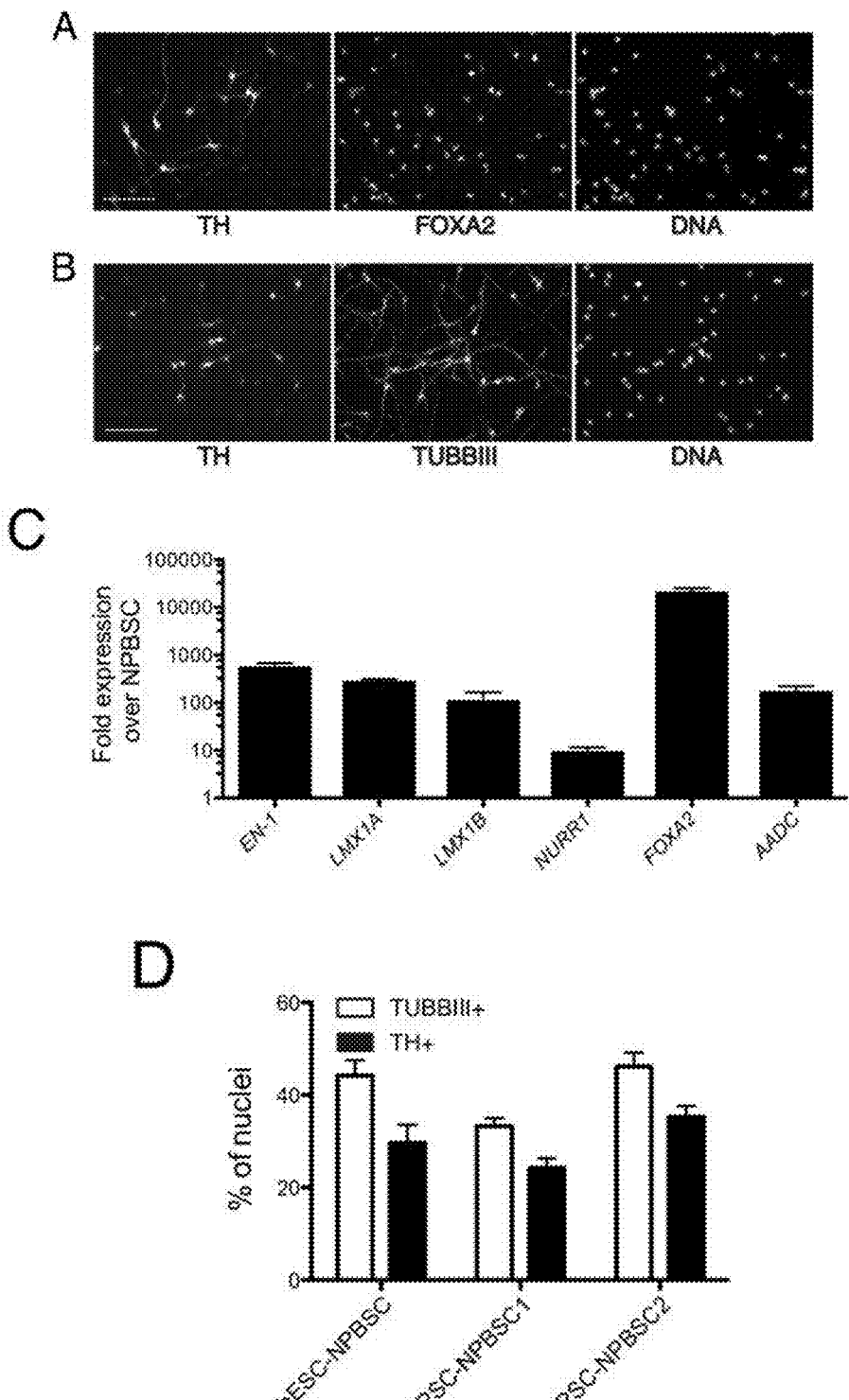

FIG. 11. Directed differentiation of NPBSCs into mDA neurons. (A) hESC-derived NPBSCs were differentiated into mDA neurons and immunostained for TH and FOXA2 and counterstained for nuclei with Hoechst. (B) Immunostaining of NPBSC-derived mDA neurons for TH and TUBIII and counterstained for nuclei with Hoechst. (C) qRT-PCR analysis of NPBSC-derived cultures for the indicated markers of mDA neuron specification at day 21. Error bars show tandard deviation from three different experiments. (D) Efficiency of mDA neuron formation for three independent NPBSC lines. Error bars represent the variation between two independent cultures. Scale bars are 100 µm.

Figure 12:
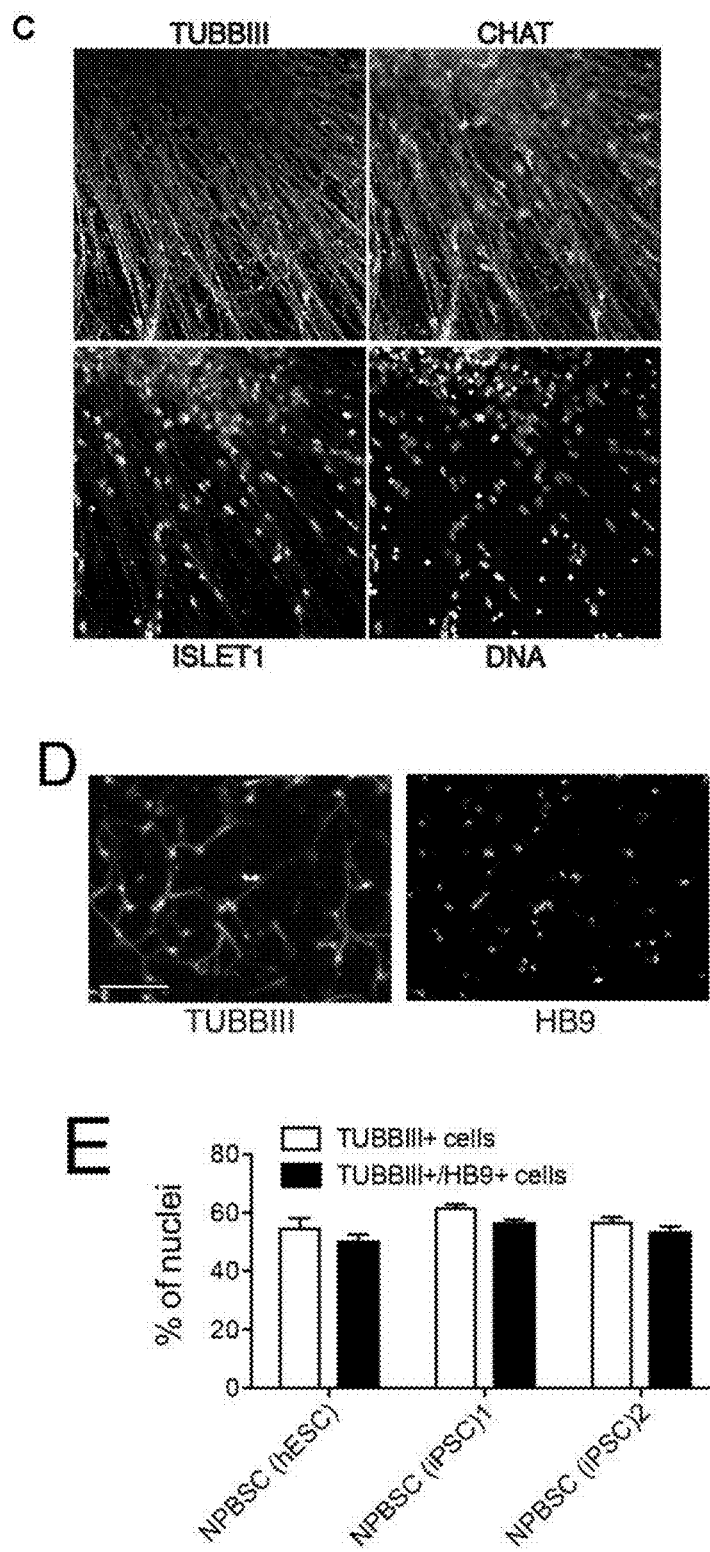

FIG. 12. Directed differentiation of NPBSCs into motor neurons. (A) Immunostaining of NPBSC-derived motor neuron progenitors at day 8 of differentiation for OLIG2, and counterstained for nuclei with Hoechst. (B) qRT-PCR analysis of NPBSC-derived cultures for the indicated markers of mDA neuron specification at day 21 of differentiation. Error bars show standard deviation of three independent experiments. (C) hESC-derived NPBSCS were differentiated into motor neurons and immunostained for ISLET1, CHAT, and TUBIII and counterstained for nuclei with Hoechst. (D) Immunostaining of NPBSC-derived motor neurons showing colocalization of HB9 and TUBIII. (E) Motor neuron differentiation efficiency from NPBSCs was approximately 50% as determined by TUBBIII and HB9 colocalization. Error bars represent variation from three independent cultures. Scale bars are 100 µm.

Figure 13:
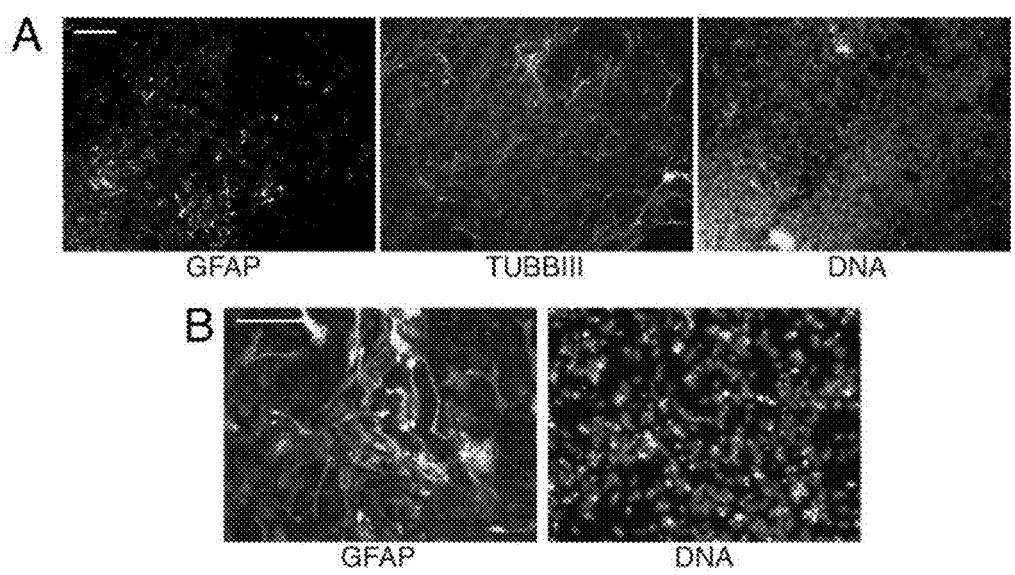

FIG. 13. Glial differentiation of NPBSCs. (A) NPBSCs were differentiated by withdrawal of CHIR and PMA. After three weeks, TUBBIII positive neurons and GFAP positive astrocytes are generated. (B) Mostly GFAP-positive astrocytes were observed when cultures were differentiated with 10% fetal calf serum and split as single cells once confluent. Scale bars are 100 µm.

Figure 14:
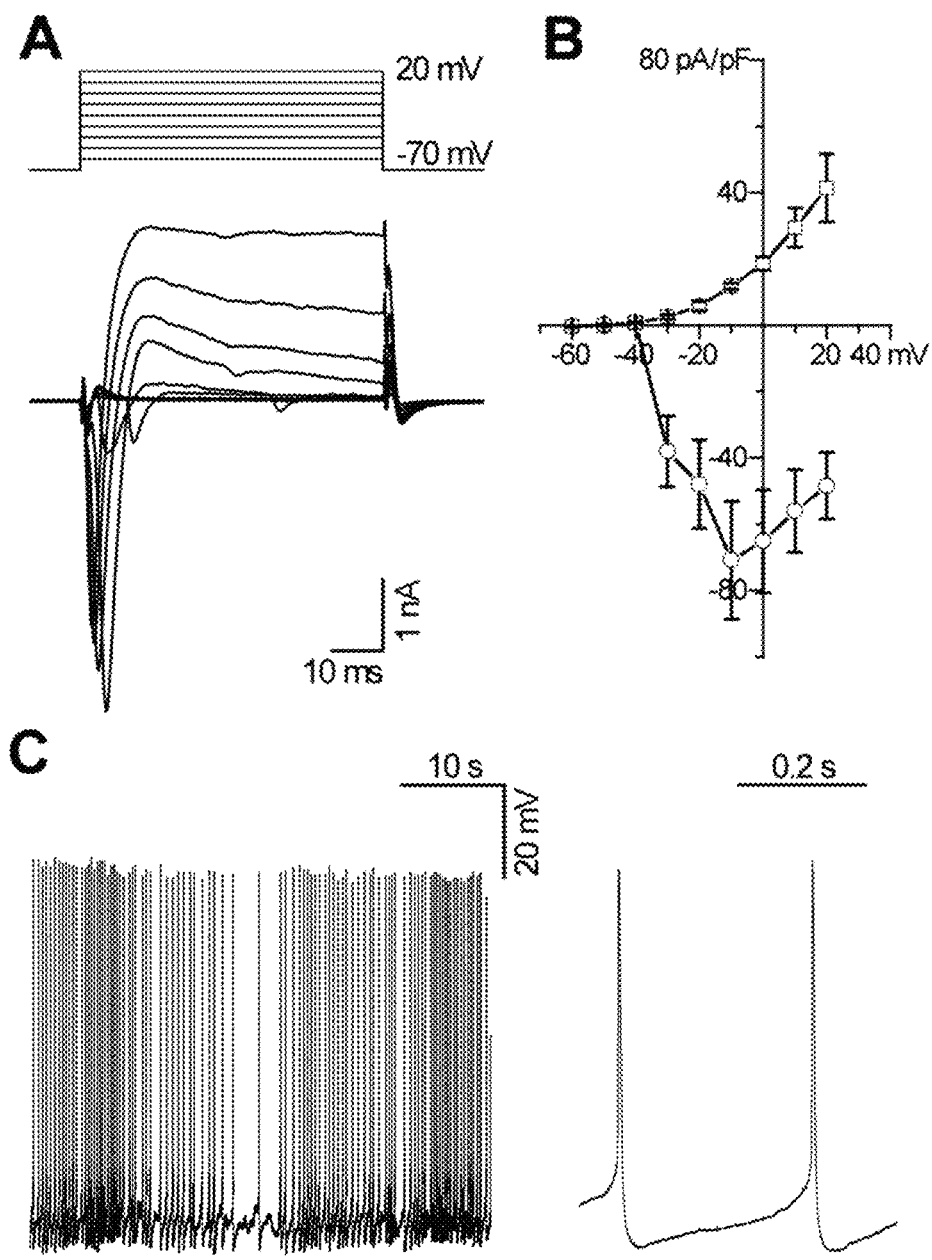

FIG. 14. NPBSC-derived neurons acquire excitable properties of neuronal cells. (A) The net of transmembrane currents, elicited by the voltage steps from holding potential −70 mV to +20 mV with 10 mV increment (the above panel shows stimulation paradigm). (B) Current-voltage relationship of inward and outward currents, measured on the peak and normalized to cell capacitance (n=8). (C) Cells demonstrate spontaneous firing of APs likewise neurons. Right panel shows more detailed view on the unitary APs.

Figure 15:
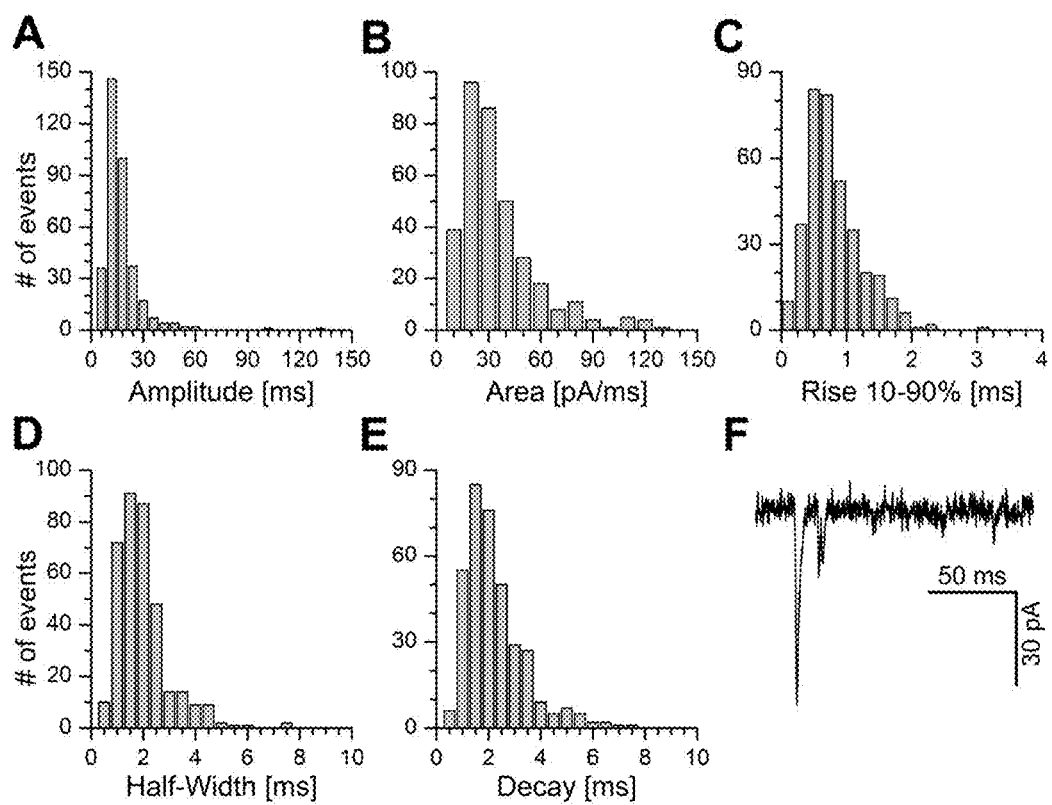

FIG. 15. Miniature spontaneous activity in NPBSC-derived neurons. (A-E) Amplitude and kinetic parameters (n=7 cells) and an exemplary recording of minis (F) performed at holding potential −70 mV.

Figure 16:
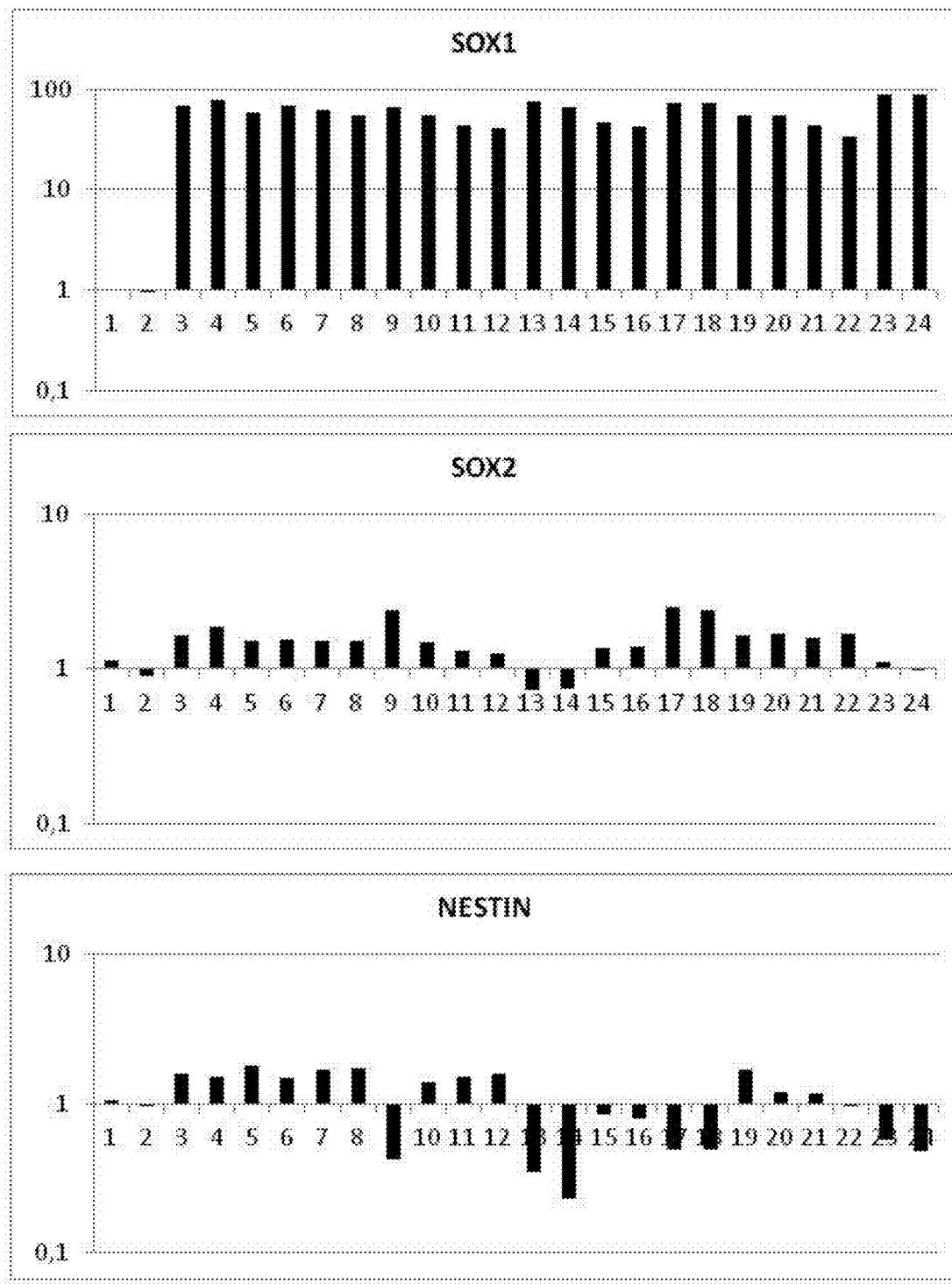
Figure 16:
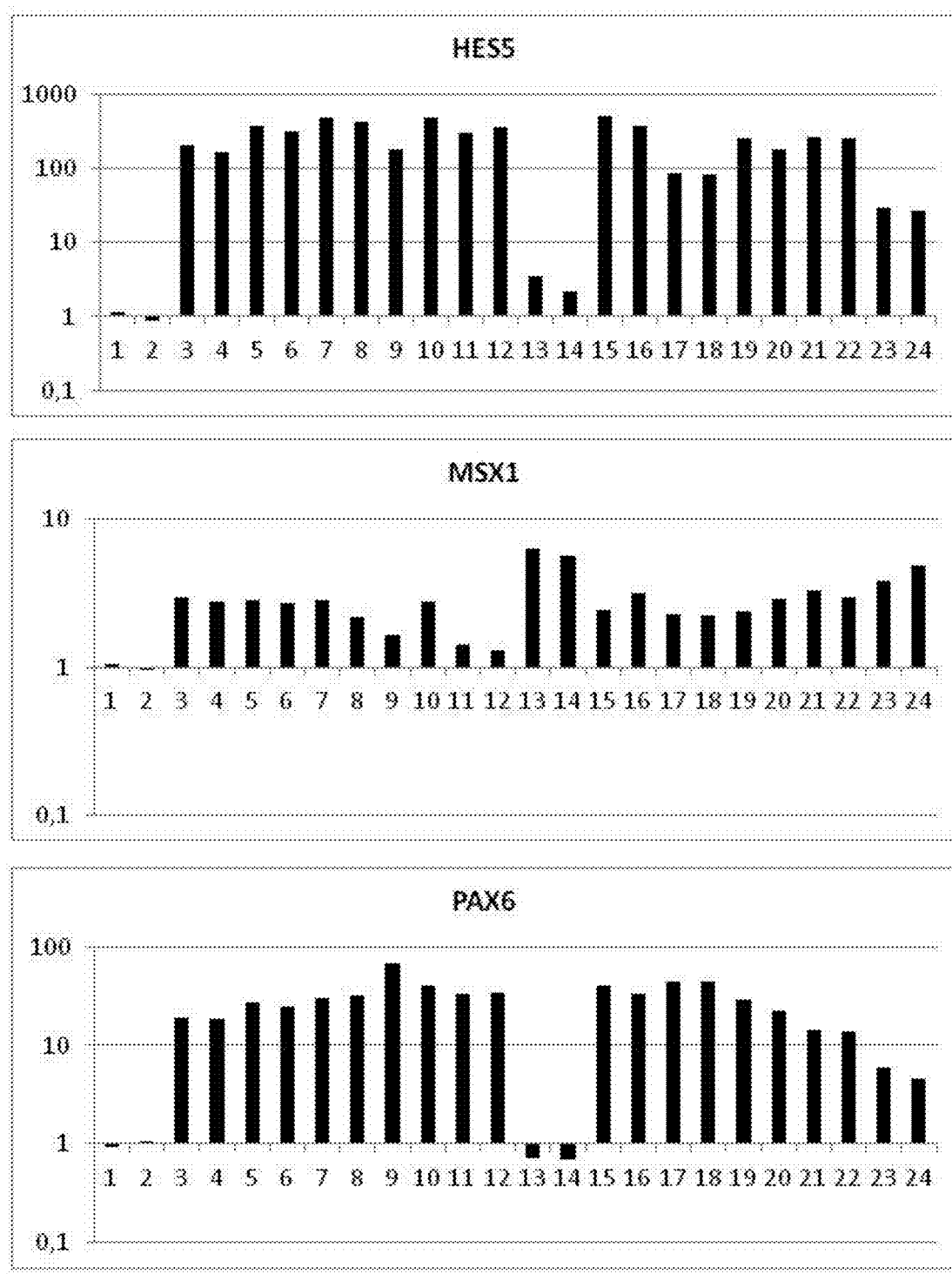
Figure 16:
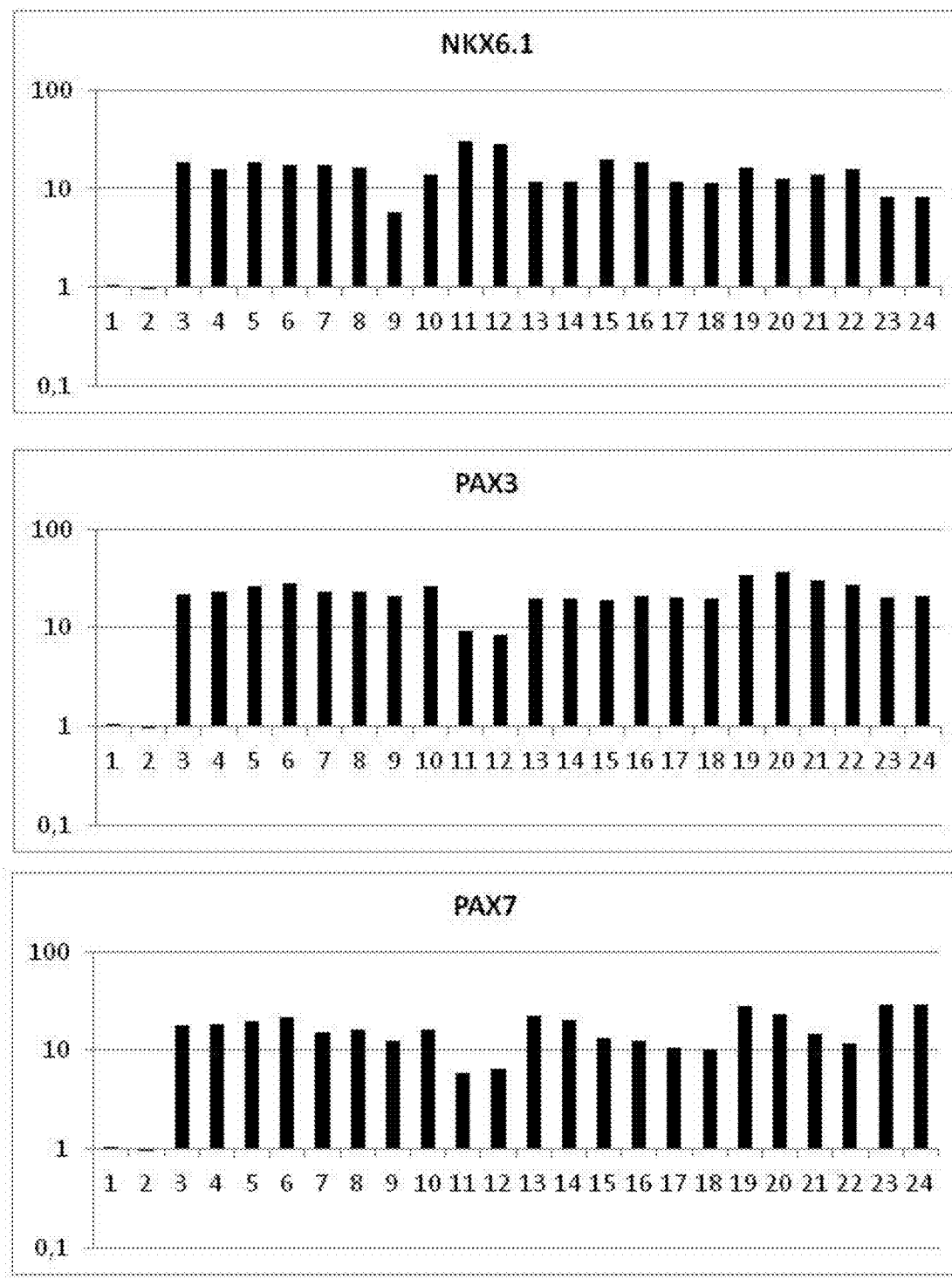
Figure 16:
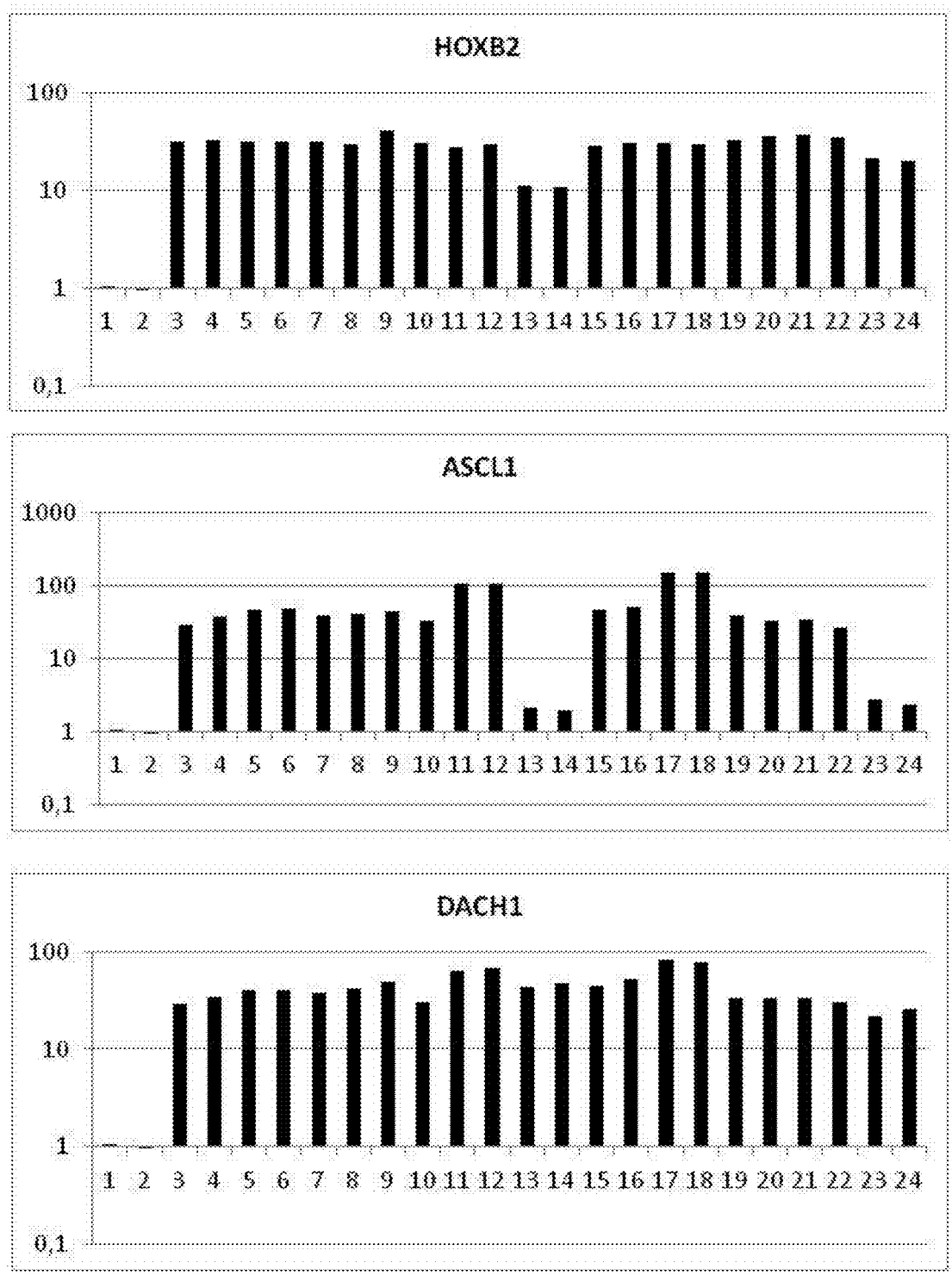
Figure 16:
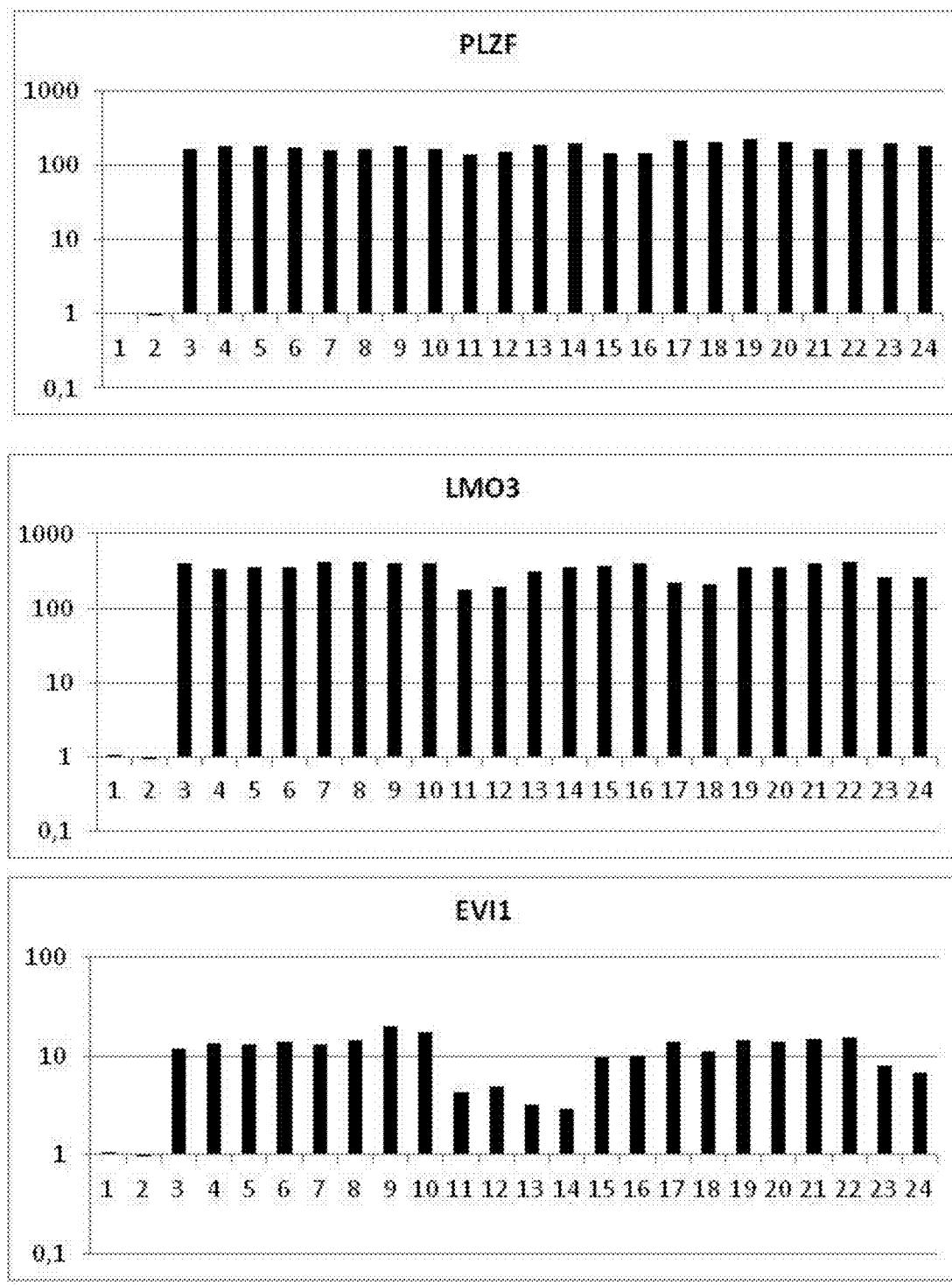
Figure 16:
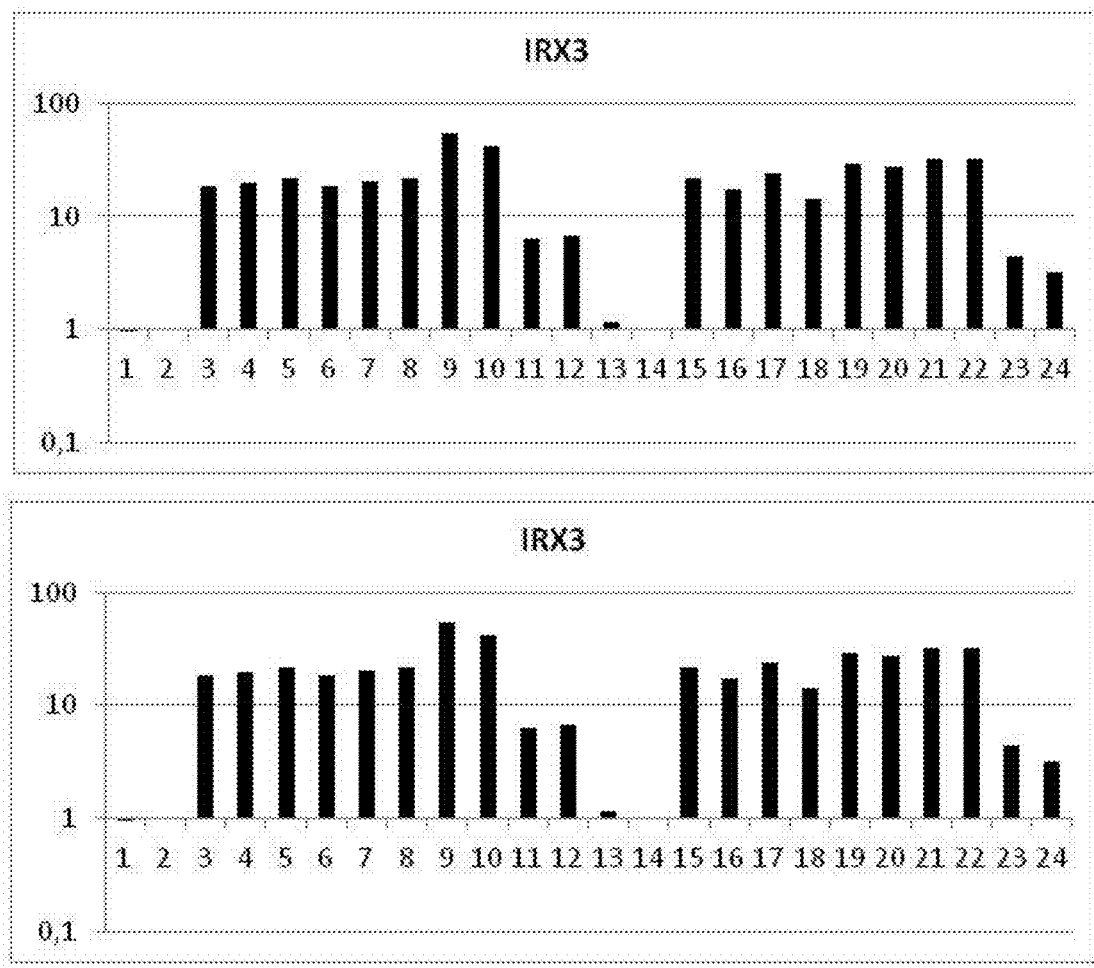

FIG. 16: Marker gene expression analysis after cell culture with different concentrations of compounds employed. The numbering refers to: 1=human embryonic stem cells—replicate 1; 2=human embryonic stem cells—replicate 1; 3=5 µM SB431542—replicate 1; 4=5 µM SB431542—replicate 2; 5=20 µM SB431542—replicate 1; 6=20 µM SB431542—replicate 2; 7=0.5 µM dorsomorphin—replicate 1; 8=0.5 µM dorsomorphin—replicate 2; 9=5 µM dorsomorphin—replicate 1; 10=5 µM dorsomorphin—replicate 2; 11=2 µM CHIR 99021—replicate 1; 12=2 µM CHIR 99021—2; 13=4 µM CHIR 99021—replicate 1; 14=4 µM CHIR 99021—replicate 2; 15=0.25 µM PMA—replicate 1; 16=0.25 µM PMA—replicate 2; 17=1 µM PMA—replicate 1; 18=1 µM PMA—replicate 2; 19=0 µM ascorbic acid—replicate 1; 20=0 µM ascorbic acid—replicate 2; 21=500 µM ascorbic acid—replicate 1; 22=500 µM ascorbic acid—replicate 2; 23=original conditions—replicate 1 and 24=original conditions—replicate 2.

Figure 17:
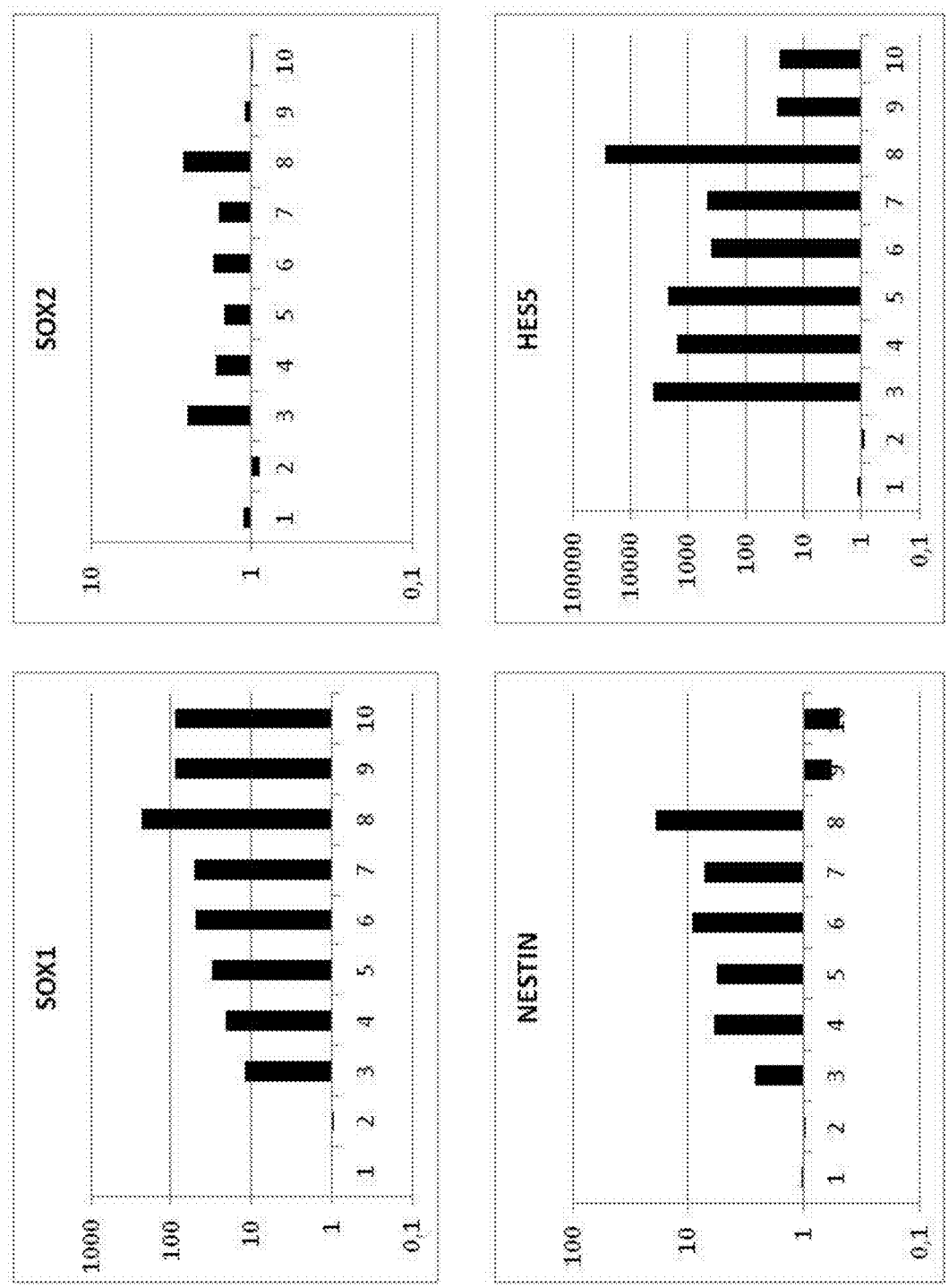
Figure 17:
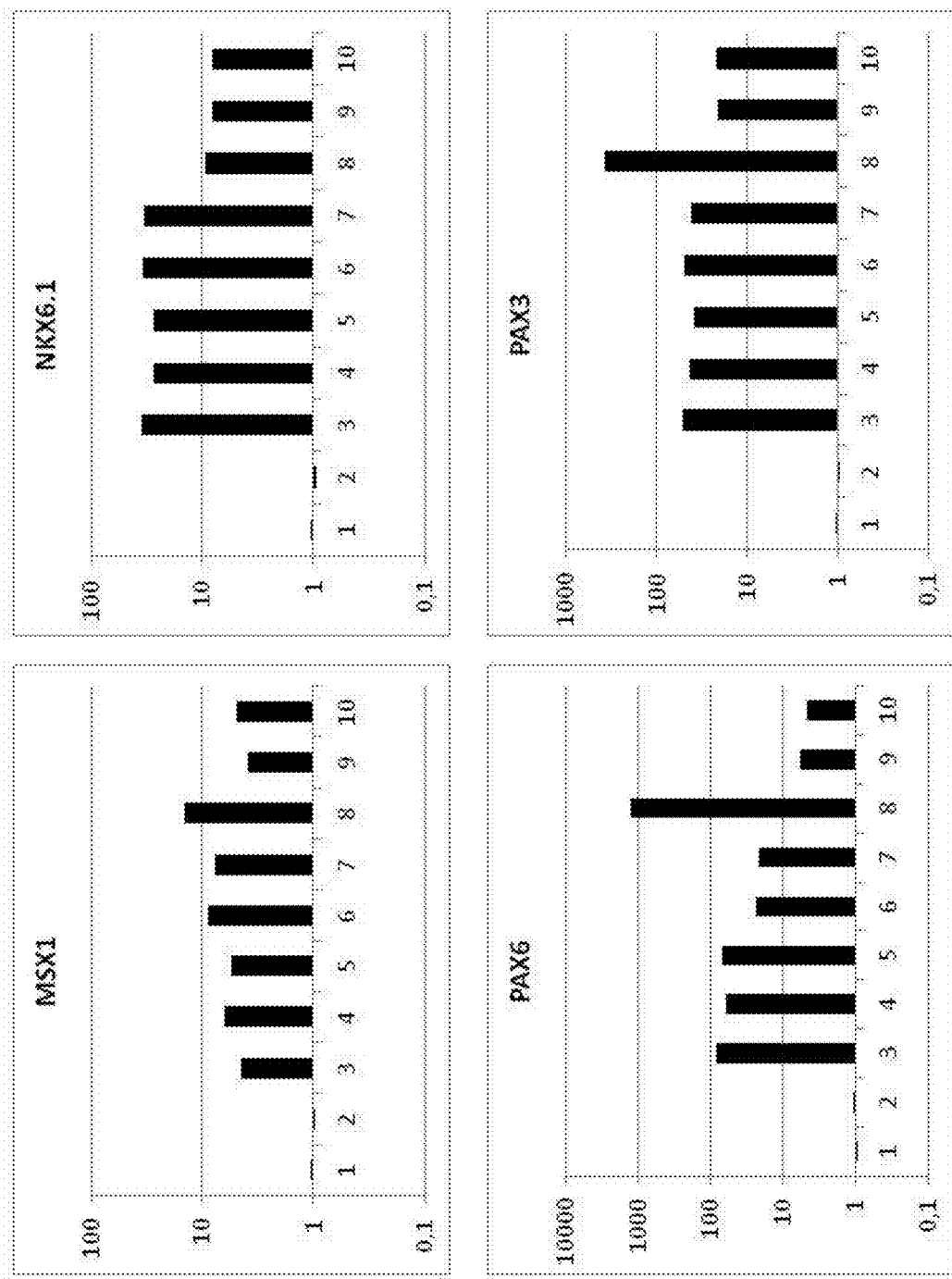
Figure 17:
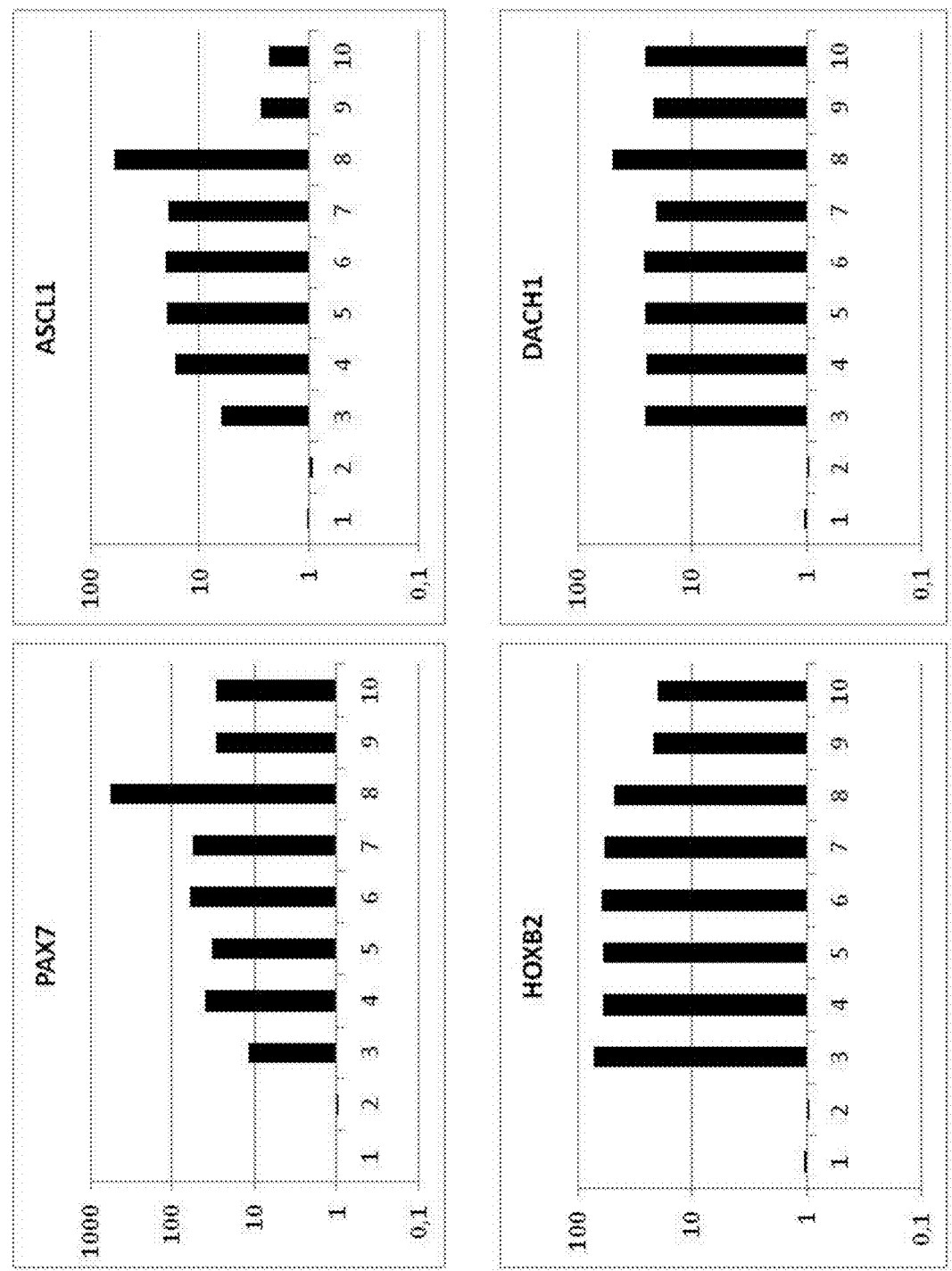
Figure 17:
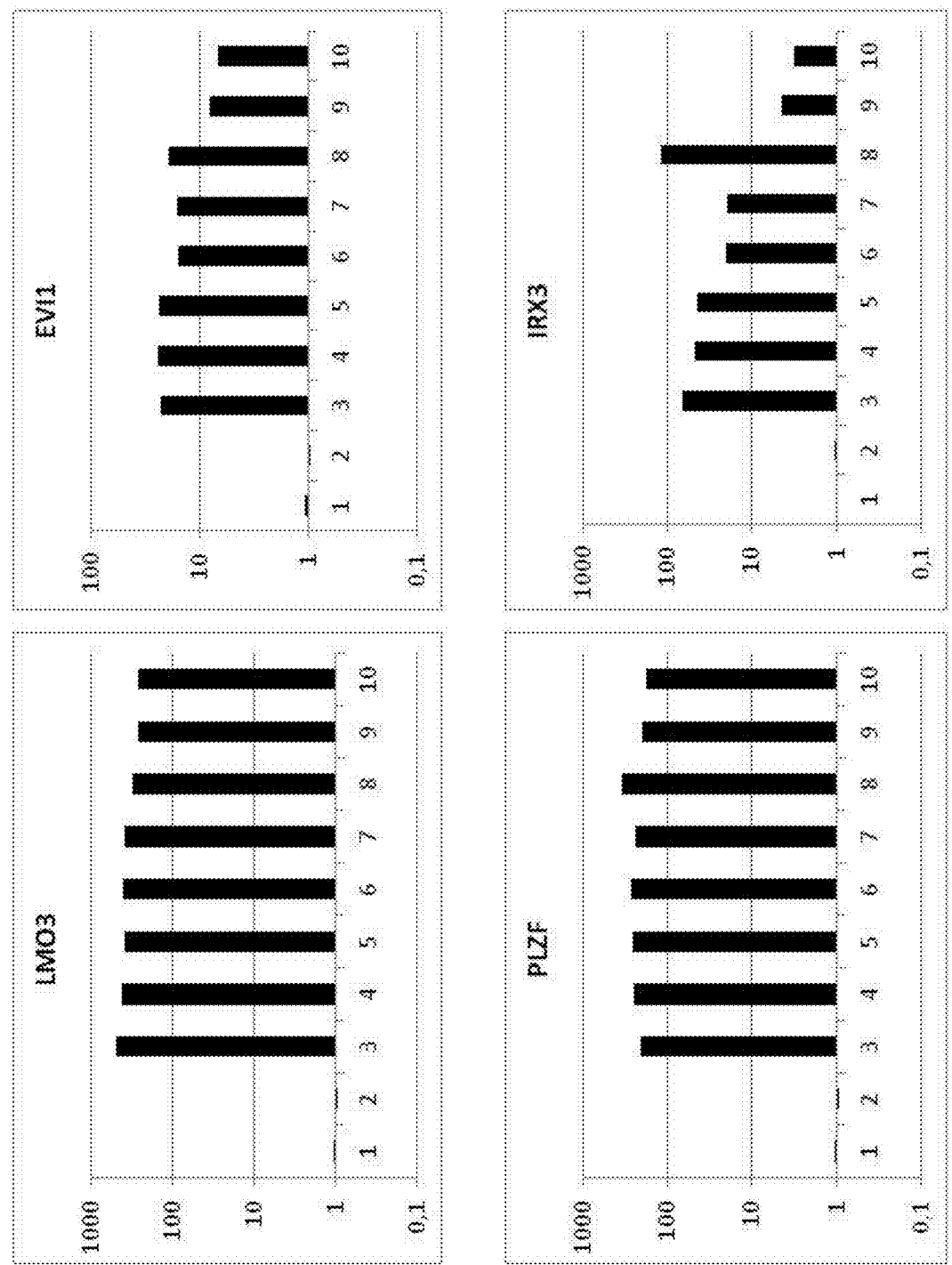
Figure 17:
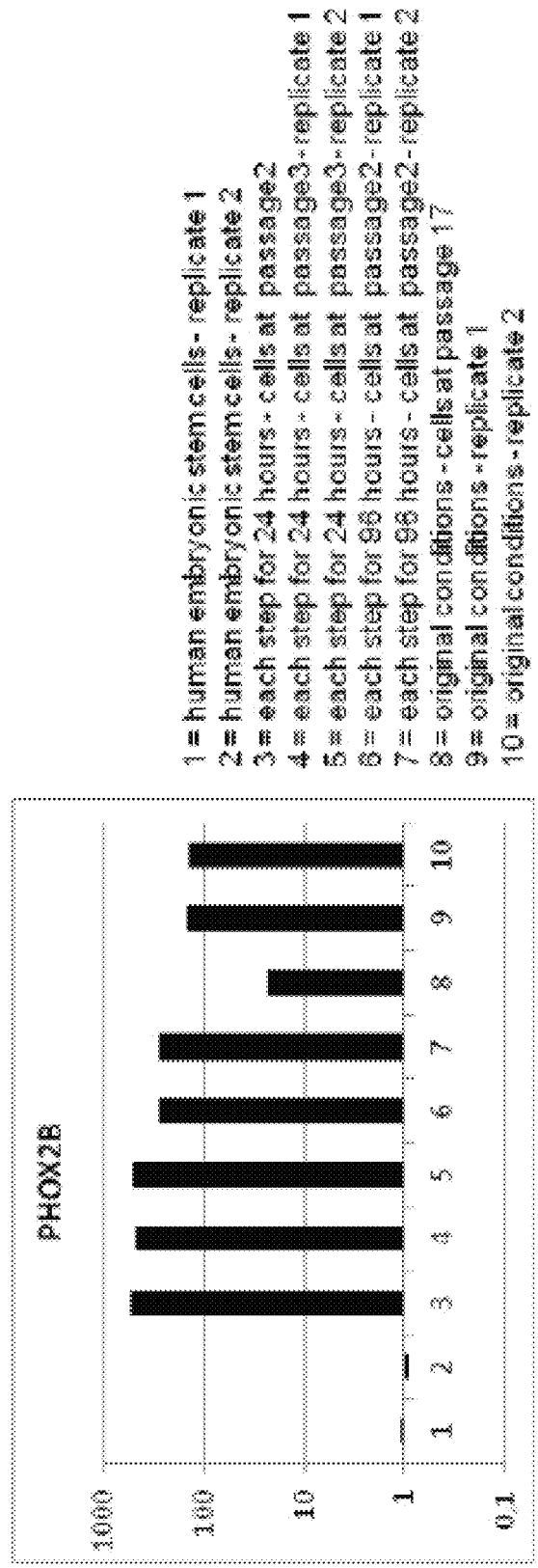

FIG. 17: Marker gene expression analysis after cell culture with different time periods of treatment employed. The numbering refers to: 1=human embryonic stem cells—replicate 1; 2=human embryonic stem cells—replicate 2; 3=each step for 24 hours—cells at passage 2; 4=each step for 24 hours—cells at passage3—replicate 1, 5=each step for 24 hours—cells at passage3—replicate 2; 6=each step for 96 hours—cells at passage2—replicate 1; 7=each step for 96 hours—cells at passage2—replicate 2; 8=original conditions—cells at passage 17 9=original conditions—replicate 1; 10=original conditions—replicate 2.

Figure 18:
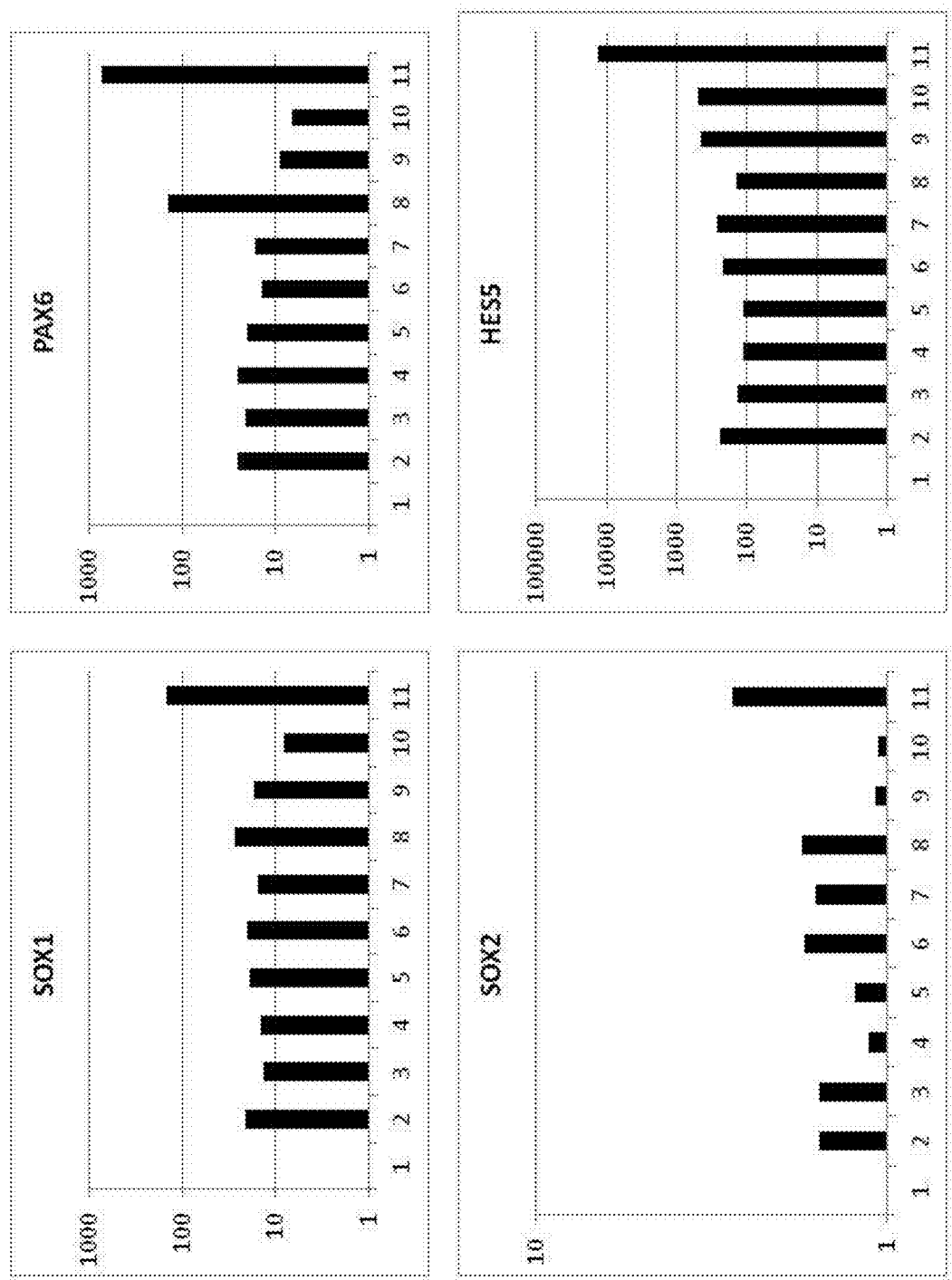
Figure 18:
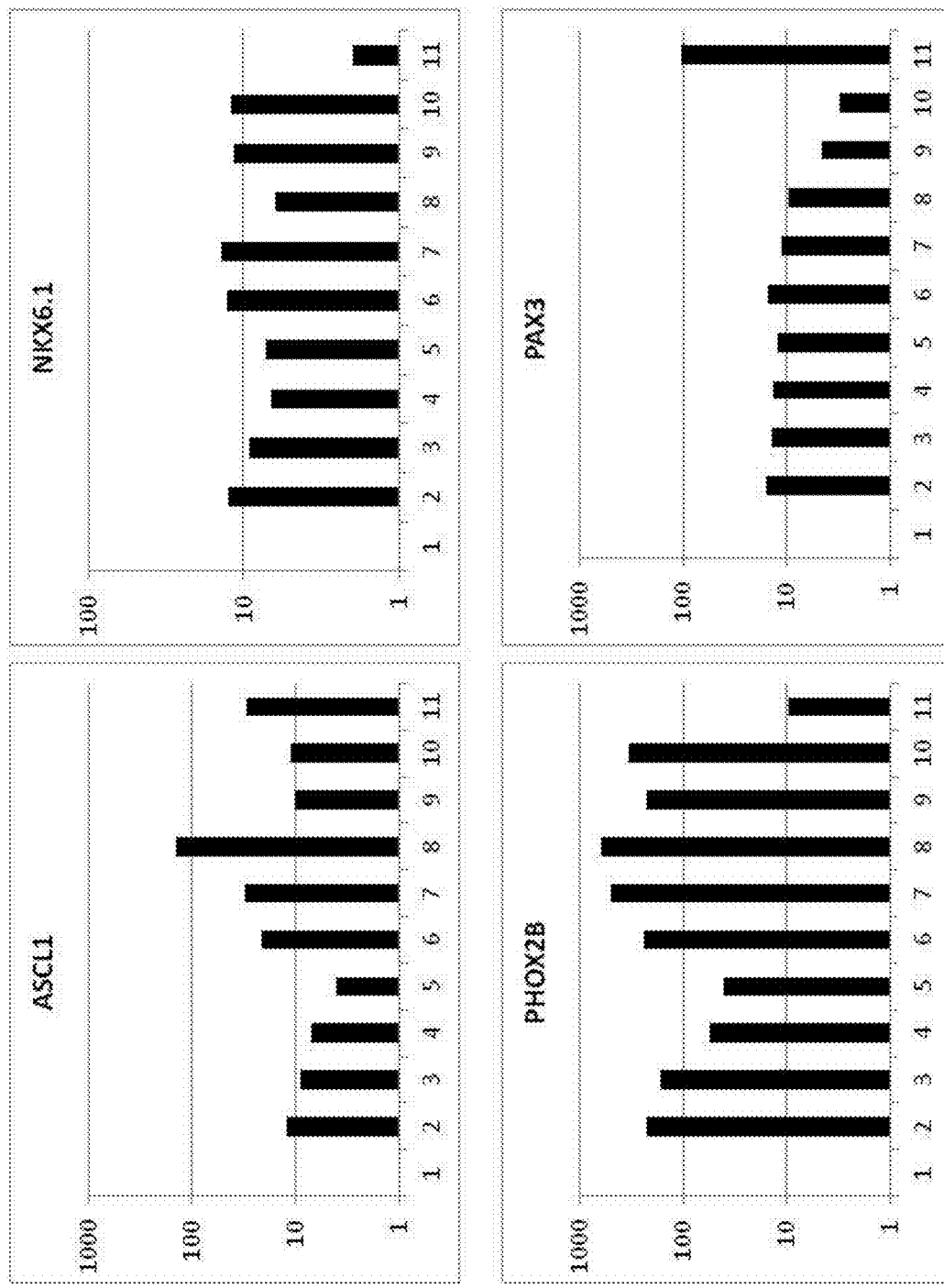
Figure 18:
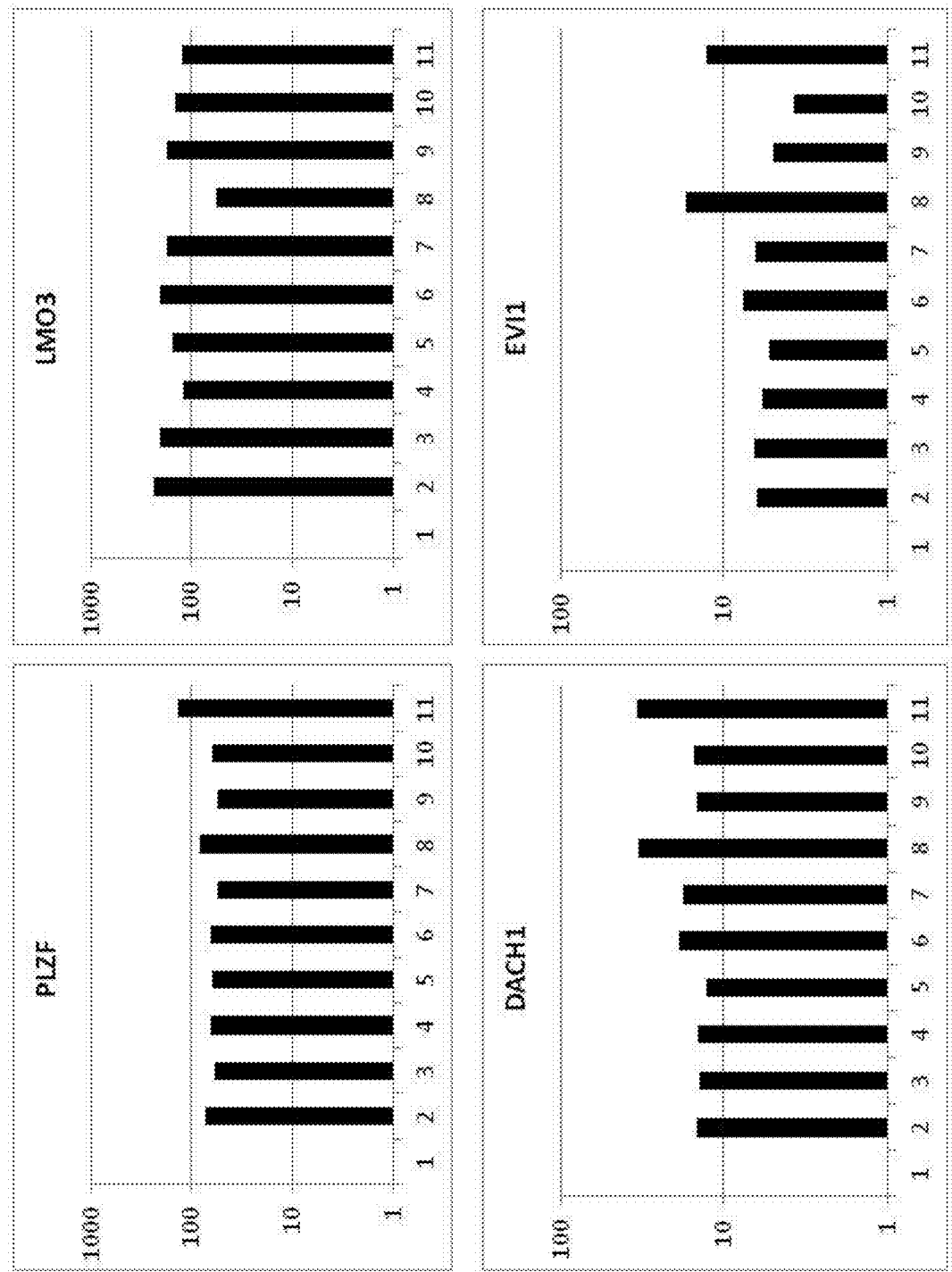
Figure 18:
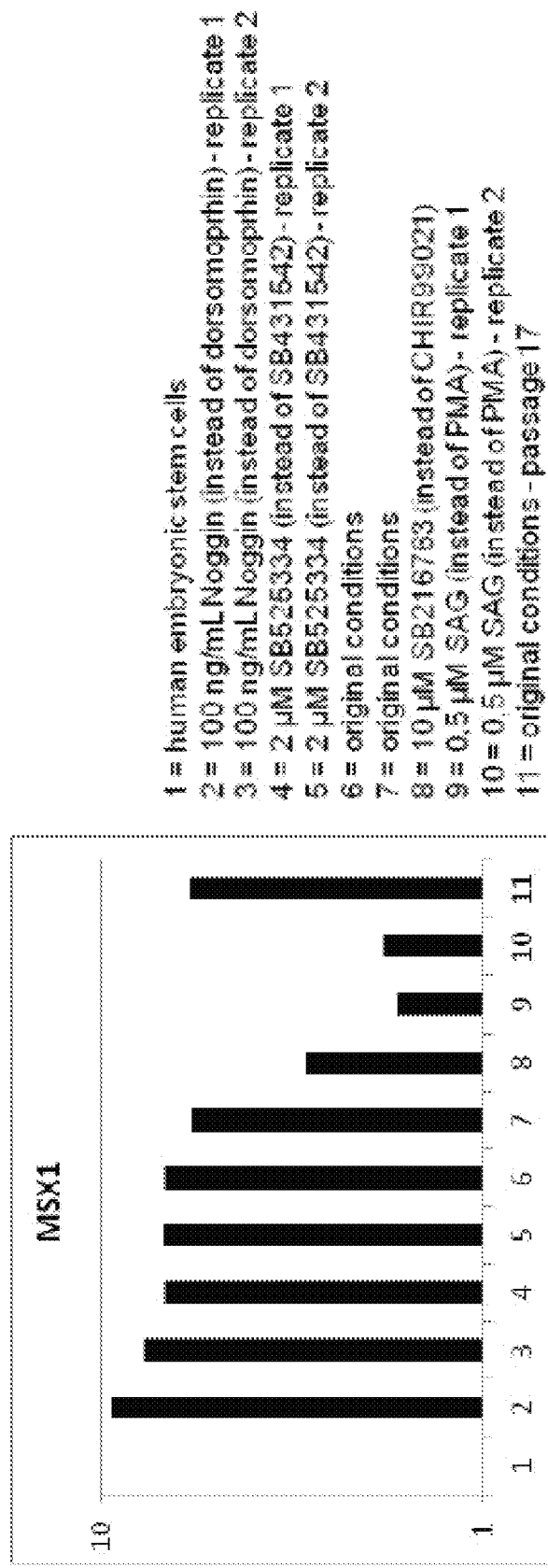

FIG. 18: Marker gene expression analysis after cell culture with varying compounds. The numbering refers to: 1=human embryonic stem cells; 2=100 ng/mL Noggin (instead of dorsomoprhin)—replicate 1; 3=100 ng/mL Noggin (instead of dorsomoprhin)—replicate 2; 4=2 µM SB525334 (instead of SB431542)—replicate 1; 5=2 µM SB525334 (instead of SB431542)—replicate 2; 6=original conditions; 7=original conditions; 8=10 µM SB216763 (instead of CHIR99021); 9=0.5 µM SAG (instead of PMA)—replicate 1; 10=0.5 µM SAG (instead of PMA)—replicate 2; 11=original conditions—passage 17.

Figure 19:
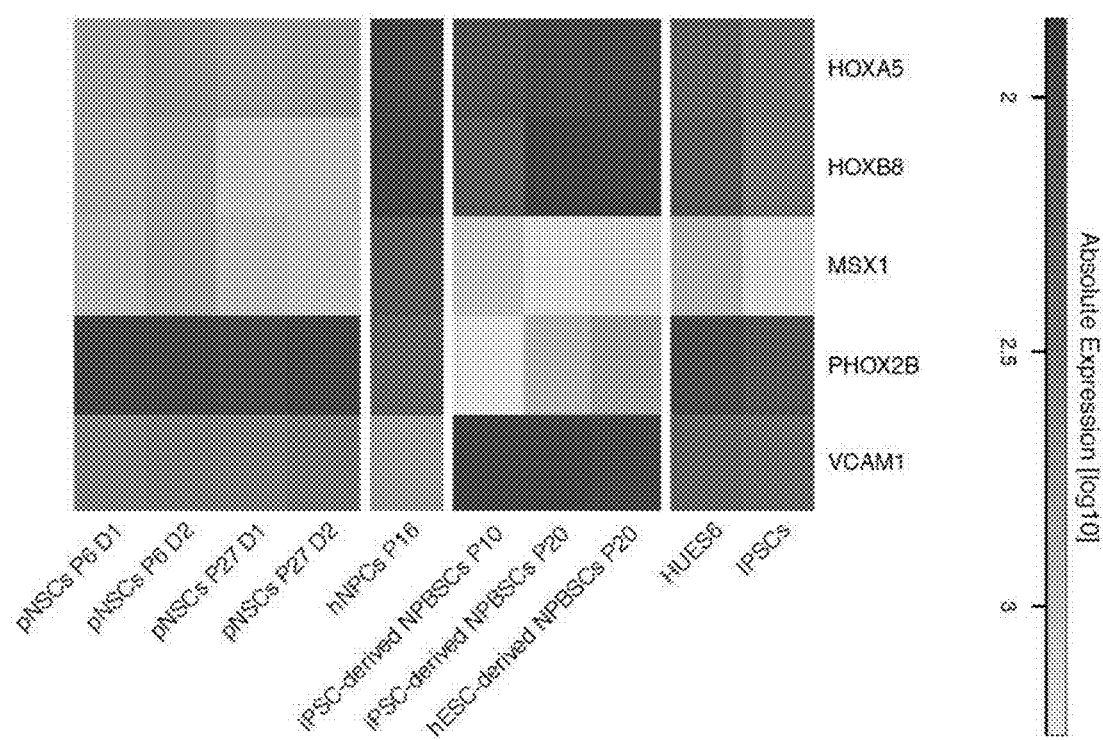

FIG. 19: Heatmap demonstrating that NPBSCs express markers that are unique to them and distinguish NPBSCs from the other cell types previously published. P10=passage 10, P20=passage 20, HUES6=human embryonic stem cells, IPSCs=induced pluripotent stem cells, pNSCs=primitive neural stem cells, hNPCs=human neural progenitor cells.

The examples illustrate the invention:

Example 1: Methods and Materials

Pluripotent Stem Cell Culture

Human ESCs and iPSCs were cultured on a layer of mitotically inactivated with mitomycin c (Tocris) mouse embryo fibroblasts (MEFs) in hESC medium. hESC medium consisted of Knockout DMEM (Invitrogen) with 20% Knockout Serum Replacement (Invitrogen), 0.11 mM beta-mercaptoethanol (Invitrogen), 1% non-essential amino-acids (NEAA, Invitrogen), 1% Penicillin/Streptomycin/Glutamine (PAA), freshly supplemented with 5 ng/ml FGF2 (Peprotech). Pluripotent stem cells were split 1:5 to 1:8 every five to seven days. Colonies were mechanically disaggregated with 1 mg/ml collagenase IV (Invitrogen). 10 μM ROCK Inhibitor (Ascent Scientific) was added for 24 hours after splitting.

NPBSC Derivation

For generation of NPBSCs from pluripotent stem cells, colonies were detached from the MEFs three to four days after splitting, using 2 mg/ml collagenase IV (Invitrogen). Colony pieces were collected by sedimentation and resuspended in hESC medium (without FGF2) supplemented with 10 μM SB-431542 (Ascent Scientific), 1 μM dorsomorphin (Tocris) for neural induction, as well as 3 μM CHIR 99021 (Axon Medchem), 0.5 μM PMA (Alexis) and cultured in petri dishes. Medium was replaced on day two by N2B27 supplemented with the same small molecule supplements. N2B27 consisted of DMEM-F12 (Invitrogen)/Neurobasal (Invitrogen) 50:50 with 1:200 N2 supplement (Invitrogen), 1:100 B27 supplement lacking vitamin A (Invitrogen) with 1% Penicillin/Streptomycin/Glutamine (PAA). On day four, SB-431542 and dorsomorphin were withdrawn and 150 μM Ascorbic Acid (AA; Sigma) was added to the medium. On day six, the EBs were triturated with a 1000 μpipette into smaller pieces and plated on Matrigel-coated (Matrigel, Growth factor reduced, high concentration; BD Biosciences) 12 well plates at a density of about ten to fifteen per well in NPBSC expansion medium (N2B27 with CHIR, PMA and AA). For coating, Matrigel was diluted to a final dilution of 1:100 in Knockout DMEM (Invitrogen) prior to coat 500 μl per well of a 12 well plate over night. Coated plates were wrapped with Parafilm and kept in the fridge for up to one month. The first split was performed at a 1:5 to 1:10 ratio on day 2 to 4 after plating. All the remaining splitting ratios were 1:10. Note that higher splitting ratios selected better for NPBSC colonies and led to a high purity with fewer splits. After a maximum of five splits, cultures were virtually free of contaminating non-NPBSC cells.

NPBSC Culture

NPBSC were cultured on Matrigel-coated 12 well plates (Nunc) cell-culture plates. NPBSC expansion medium consisted of N2B27 freshly supplemented with CHIR, PMA and AA, with a medium change every other day. Typically, cells were split 1:10 every five or six days. For splitting, cells were digested to single cells for about 15 minutes at 37° C. with prewarmed Accutase (PAA). Cells were diluted in DMEM (PAA) for centrifugation at 200×g for 5 minutes. The cell pellet was resuspended in fresh NPBSC expansion medium and plated on Matrigel-coated cell culture dishes.

Differentiation of NPBSCs

For general differentiation, it is sufficient to change NPBSC expansion medium to N2B27 medium without supplements. Once cultures became too confluent, they were split at a 1:2 to 1:3 ratio by digesting with 1 mg/ml Collagenase IV for 5 minutes at 37° C., detachment with a cell spatula and replating on fresh Matrigel-coated plates.

For generation of more ventral CNS neurons, including midbrain dopaminergic neurons (mDA), NPBSC expansion medium was changed two days after splitting to N2B27 medium with 100 ng/ml FGF8 (Peprotech), 1 μM PMA and 200 μM AA. After eight days in this medium, maturation medium—N2B27 with 10 ng/ml BDNF (Peprotech), 10 ng/ml GDNF (Peprotech), 1 ng/ml TGF-b3 (Peprotech), 200 μM AA and 500 μM dbcAMP (Sigma Aldrich)—was used for the maturation of neurons. 0.5 μM PMA was added to this medium for two more days. One day after changing to maturation medium, the cultures were split at a 1:3 ratio as small clumps, using collagenase IV (Invitrogen). Cultures were analyzed after two weeks in maturation conditions unless otherwise indicated.

For induction of posterior cells, including motor neurons, NPBSC expansion medium was changed to N2B27 with 1 μM PMA three days after splitting. Two days later, 1 μM retinoic acid (RA, Sigma) and 1 μM PMA were added for eight days. Following one day in maturation medium (N2B27 with BDNF, GDNF and dbcAMP), cultures were also split as clumps at a ratio of 1:2 to 1:3. Cells were cultured in maturation medium for two weeks.

For generation of PNS neurons, NPBSCs two days after splitting were switched to N2B27 with only CHIR for two days. Afterward, 10 ng/ml BMP4 (R&D Systems) was added for eight days. Splitting and maturation was performed as described for the generation of motor neurons. For astrocyte and mesenchymal neural crest differentiation, NPBSCs were cultured with DMEM (PAA) with 10% fetal calf serum (PAA) and 1% Pen/Strep/Glutamin (PAA), beginning two days after splitting. Cultures were split twice at a 1:3 ratio when confluent using trypsin (Invitrogen).

Immunocytochemistry

For confocal microscopy, cells were plated on Matrigel-coated glass coverslips. Cultures were fixed for 20 minutes with 4% paraformaldehyde (Electron Microscopy Sciences) in PBS (Invitrogen) and washed twice with PBS. Permeabilization and blocking was done in one step using 0.1% Triton X-100 (Sigma Aldrich), 10% fetal calf serum (PAA) and 1% BSA in PBS for 45 minutes. Plates or coverslips were washed once with 0.1% BSA in PBS and the primary antibodies applied overnight at 4° C. in 1% BSA in PBS. The next day, following one washing step with 0.1% BSA in PBS, secondary antibodies were applied for one hour at room temperature in 1% BSA in PBS. Finally, cells were washed three times with 0.1% BSA in PBS-T (0.05% Tween 20), including a Hoechst counterstaining for nuclei in the second washing step. Cells were mounted in Vectashield mounting medium (Vector Labs) and imaged on a Zeiss PALM/Axiovert fluorescence microscope or a Zeiss LSM700 confocal microscope. If necessary, images were merged using ImageJ and Adobe Photoshop.

The primary antibodies used in this study are mouse anti NESTIN (1:150, R&D), goat anti SOX1 (1:150, R&D), rabbit anti PAX6 (1:300, Millipore), goat anti SOX2 (1:200, Santa Cruz), mouse anti FOXA2 (1:100, Santa Cruz), rabbit anti TH (1:500, Pel Freez), mouse anti TUBBIII (1:1000, Covance), rabbit anti OLIG2 (1:200, Sigma Aldrich), rabbit anti TUBBIII (1:2000, Covance), rabbit anti ISLET1 (1:500, Abcam), goat anti CHAT (1:100, Millipore), mouse anti BRN3A (1:500, Santa Cruz) and rabbit anti PERIPHERIN (1:200, Millipore). All secondary antibodies were obtained from Invitrogen and were conjugated to AlexaFluor fluorochromes.

Quantitative RT-PCR (qRT-PCR)

Total RNA was isolated from cultured cells using RNeasy columns (Qiagen), according to manufacturer instructions, including an on-column DNase digest. Isolated RNA was reverse-transcribed using M-MLV Reverse Transcriptase (USB) with oligo-dT$_{16}$ primers (Metabion) for 1 h at 42° C. qRT-PCR was performed on an Applied Biosystems 7500 Real-Time PCR system with SYBR green PCR master mix (ABI) and 56 ng of original RNA equivalents per 20 µl PCR reaction. Cycling conditions were 40 cycles of 15 s, 95° C./60 s 60° C. Relative expression levels were calculated using the $2^{-2\Delta}$ method, normalized to biological reference samples and using GAPDH and ACTB as housekeeping genes.

Whole Genome Expression Analysis

DNA-free total RNA samples (500 ng) to be hybridized on Illumina human-12 V3 expression BeadChips were processed using a linear amplification kit (Ambion) generating biotin-labeled cRNA (IVT duration: 14 h). This was quality-checked on a 2100 Bioanalyzer (Agilent) and hybridized as recommended and using materials/reagents provided by the manufacturer. In BeadStudio, raw data were background-subtracted and normalized using the "cubic spline" algorithm. Differential gene expression was assessed on the basis of thresholds for both expression ratios and statistical significance employing the "Illumina custom" algorithm considering standard deviations from replicate beads within each array. Signal intensities below ca. 50% of the detection threshold were arbitrarily trimmed to the value corresponding to 50% of detection. This procedure underestimates expression changes for genes undetectable in the reference sample (or vice versa) but avoids nonsense ratios, such as negative or unrealistically high values.

Karyotype Analysis

NPBSCs at passage 25 were cultured until confluent. 0.2 µg/ml colcimid (Invitrogen) was added and the cells incubated at 37° C. After 45 minutes, the colcimid containing medium was removed, the cells washed with PBS and digested to a single cell suspension with prewarmed Accutase, diluted in DMEM and collected by centrifugation. The cell pellet was resuspended in 37° C. prewarmed 75 mM KCl solution and incubated at room temperature for ten minutes. Cells were collected by 5 minutes centrifugation at 250×g, once again resuspended in prewarmed KCl solution and immediately collected by centrifugation. The pellet was resuspended in 5000 KCl solution and ice-cold fixation solution (3:1 methanol/acetic acid) was added drop wise while carefully shaking the cell suspension. Once fixed, the cells were collected by centrifugation and carefully resuspended in fresh fixative and again pelleted. This procedure was repeated until the supernatant after centrifugation remained clear. Cells were spread by dropping different dilutions in fixative on glass slides (Menzel Gläser, Thermo Scientific). One day later, cells were mounted in Vectashield with DAPI (Vector Labs) and metaphase spreads were analyzed on a Zeiss AxioVision Fluorescence microscope at 63× magnification with oil immersion. At least 10-15 countable spreads were recorded and counted for each line.

Generation of Single-Cell Clonal Lines

For the generation of single cell clones, NPBSCs were infected with a pLenti CMV-SV40-Blasticidine construct based on the pLenti6/V5 expression system (Invitrogen), which includes a blasticidin resistance cassette. Virus production was performed in 293T cells using the ViraPower packaging mix (Invitrogen). One 6 cm plate 293T cells were transfected using FuGENE 6 (Roche) according to the manufacturer's instructions with 2 µg packaging mix and 1 µg expression construct. One day after transfection, medium was changed against N2B27 medium. The following day, the medium supernatant was filtered to remove 293T cells, supplemented with 6 µg/ml protamine sulfate (Sigma), 3 µM CHIR 99021, 0.5 µM PMA, 150 µM AA and directly used for infection of freshly plated NPBSC. The next day, infected NPBSC were washed four times with PBS and fed with fresh NPBSC expansion medium. Selection with 5 µg/ml blasticidine (PAA) in NPBSC expansion medium started two days later and was maintained for two more weeks.

Blasticidin resistant NPBSC were digested and triturated to single cells using Accutase for 30 minutes and filtered using a 40 µm cell strainer (BD Biosciences) to remove remaining cell aggregates. Single cells were counted and seeded at a density of 50 cells per well on a Matrigel-coated well of a 6 well plate, together with approximately 200,000 uninfected NPBSCs in expansion medium. Four days later, cells were again selected with 5 µg/ml blasticidin, until only resistant, single colonies remained on the plate that were spotted and marked. Selection was maintained for one more week, single colonies picked, replated on 4 well-plates and expanded under standard NPBSC conditions, blasticidin resistance was continued for one more week to exclude surviving non-resistant cells. Once sufficiently expanded, single cell-derived clones were differentiated as described above.

Evaluation of Electrophysiological Function

The transmembrane currents and spontaneous activity were recorded from NPBSC-derived neurons, differentiated for 3 weeks, using the whole-cell configuration of the patch-clamp technique (Hamill et al., 1981). The patch pipettes were fabricated from borosilicate glass on a PIP-6 pipette puller (HEKA Elektronik, Lambrecht, Germany). When filled with pipette solution they had tip resistances of 5-7 MΩ. Recordings were done using a HEKA EPC-9 amplifier (HEKA Elektronik, Lambrecht, Germany) and Pulse 8.61 Aqusition Software (HEKA Elektronik, Lambrecht, Germany). Series resistance and pipette and whole-cell capacitance were cancelled electronically. Cells were perfused with a bath solution containing (mM): NaCl 140, KCl 2.4, MgCl2 1.3, CaCl2 2.5, HEPES 10, D-glucose 10, pH 7.4. The pipette solution contained (mM): K-gluconate 125, NaCl 10, EGTA 1, MgATP 4, HEPES 10, D-glucose 10, pH 7.4. All experiments were performed at room temperature. Recordings of current-voltage relationship ("I-V curves") or miniature spontaneous activity ("minis") were done in voltage-clamp mode at holding potential −70 mV. Recordings of spontaneous firing of action potentials ("AP") were performed in current-clamp mode at 0 pA holding current i.e. at own cell's membrane potential.

Data were analyzed using Patcher's Power Tool routine (developed by Dr. F. Mendez and F. Würriehausen, MPI BPC, Göttingen, Germany) for IgorPro (WaveMetrics, Lake Oswego, Oreg., USA) and Origin 7.5 (Origin Lab Corp., Northampton, Mass., USA). Minis were analyzed with Mini Analysis 6.0 software (Synaptosoft Inc., Fort Lee, N.J., USA).

Example 2: Derivation and Characterization of Human NPBSCs

Differentiation of human pluripotent stem cells via embryoid bodies (hEBs) was used to model human embryogenesis. To ensure reproducibility, all experiments were conducted with both human embryonic stem cells (hESCs; human ES cell line HUES6 from Chad A. Cowan, et al. N Engl J Med 2004; 350:1353-1356) and human induced pluripotent stem cells (hiPSCs). Neural induction was initiated through the use of dual inhibition of SMAD signaling (Chambers et al., 2009). First, we sought to determine the window of competence to respond to patterning by SHH signaling for differentiating human cells. Previously, Fasano et alia demonstrated that floor plate differentiation was most efficiently induced when SHH was added from day 1 of the differentiation of hESCs (Fasano et al., 2010). Since floor plate is most ventral portion of the neural tube, we reasoned that hESCs might have an early window of competence for the efficient specification of ventral neural tube progenitor lineages by SHH signaling. To test this, differentiating hEBs were exposed to purmorphamine (PMA), which is a small molecule agonist of the SHH receptor SMO, starting on different days (FIG. 1). Consistent with the results of Fasano et alia, quantitative RT-PCR (qRT-PCR) analysis demonstrated that the ventral neural progenitor markers NKX6.1 and OLIG2 were most efficiently upregulated when PMA was applied as early a day 2 during differentiation (FIG. 1) (Fasano et al., 2010). A significant decrease in the efficiency of ventral neural tube fate specification as marked by NKX6.1 and OLIG2 expression was observed when PMA was delayed as little as two more days (FIG. 1).

Because the temporal window for competence to respond to SHH is so narrow, it would be impossible to significantly expand the number of cells in culture while maintaining their ability to be efficiently specified by SHH signaling into ventral neural tube lineages. As such, we sought to identify culture conditions that enable the expansion of cells in vitro that retain the ability to be patterned by hedgehog signaling, which is normally lost within 4 days of the initiation of differentiation. WNT proteins are potent mitogens, and WNT signaling is known to oppose SHH signaling. We speculated that WNT signaling might facilitate the expansion of the window of competence for differentiating hESCs to remain responsive to SHH signaling. Therefore, we tested the effects of adding both WNT and SHH signals to cultures of differentiating hESCs. The small molecule CHIR99021 (CHIR), which is a GSK3B inhibitor, was added to stimulate the canonical WNT signaling pathway. Differentiating hEBs exposed to CHIR and PMA were marked by the formation and expansion of an epithelium morphologically resembling neural plate about day 6 (FIG. 2A). When disaggregated and plated on Matrigel, homogeneous colonies of epithelial cells were formed (FIG. 2B). These cells, which we named NPBSCs, could be expanded as cell lines for more than 70 population doublings and maintained a diploid karyotype (FIG. 3). Interestingly, attempts to derive NPBSCs from monolayer differentiation cultures were unsuccessful, which suggest that factors produced or the 3-dimensional environment of cells within EBs are necessary for NPBSC derivation (FIG. 4). Immunostaining demonstrated that NPBSC colonies uniformly expressed the neural progenitor markers SOX1, SOX2, NES, and PAX6 (FIG. 2C). Therefore, NPBSCs express characteristic markers of neural progenitors.

To further characterize NPBSCs, we performed microarray expression analysis. As expected, NPBSCs showed no significant expression of the pluripotent markers OCT4 and NANOG, nor mesendodermal markers AFP, T, and SOX17, nor of the trophoblast marker EOMES (FIG. 5). In contrast, NPBSCs showed high expression of neural markers including SOX2, PAX6, HES5, and ASCL1 (FIG. 5). qRT-PCR analysis confirmed that NPBSCs express markers of neural progenitors, including PAX6, SOX2, SOX1, and PAX3, which were stably expressed beginning at about passage 4 (FIG. 6). qRT-PCR also confirmed that non neural markers including OCT4, AFP, SOX17, CK8, CK18, and T were not expressed by NPBSCs (FIG. 5). An analysis of doubling time indicated that NPBSCs divided approximately once per day, which was stable over multiple passages and also multiple cell lines (FIG. 7). These results demonstrate that NPBSCs are a pure population of neural progenitors and maintain a stable expression pattern beginning at passage 4.

Interestingly, although NPBSCs do not morphologically resemble neural rosettes, microarray analysis demonstrated the expression of (pre-) neural rosette genetic markers DACH1, PLZF, and LMO3 (FIG. 5). This suggested that NPBSCs retain the ability to form neural rosettes. We tested this by culturing NPBSC colonies in the presence of FGF2, which has previously been reported to induce neural rosette formation by hEBs that have been plated (Zhang et al., 2001). After 2 days of culturing NPBSC colonies with FGF2, numerous neural rosettes were formed (FIG. 8A). For further characterization, we immunostained for ZO-1, which is expressed by neural rosettes but spatially localized to the apical surface (Elkabetz et al., 2008). Although ZO-1 expression was readily detected in colonies of NPBSCs, it demonstrated no preferential spatial localization within the colonies (FIG. 8B). In contrast, after FGF2 treatment, ZO-1 expression had re-oriented to the apical surface of the rosettes (FIG. 8B). Therefore, we conclude that NPBSCs express rosette markers and are capable of forming neural rosettes when cultured under the appropriate conditions, which suggests that they are developmentally upstream of neural rosettes.

Example 3: NPBSCs Resemble Caudal Neural Plate Border Cells

Since both WNT and SHH signaling are potent developmental morphogens, we sought to identify the regional identity of NPBSCs. As shown above, SHH signaling is a potent signal for ventralization. For this reason, we first used microarray data to determine the dorsoventral character of NPBSCs (FIG. 2A). Interestingly, NPBSCs expressed high amounts of IRX3. PAX6 and MSX1 were readily detectable, and PAX3 was present, but in smaller quantities (FIG. 2A). However, the most dorsal neural progenitor marker, GSH2, was not detectable. In addition, ventral markers such as NKX6.1, OLIG2, NKX2.2, and FOXA2 were not expressed (FIG. 2A). These results indicate that NPBSCs have a moderately dorsal character, which is consistent with the known opposing roles of WNT and SHH in specifying dorsoventral identity. Microarray data for rostrocaudal markers also demonstrated that only the genes HOXA2 and HOXB2, which mark anterior hindbrain identity, were significantly expressed (FIG. 2B). This result is consistent with the known role of WNT signaling in specifying caudal identity (Kiecker and Niehrs, 2001). Therefore, we conclude that NPBSCs are neural progenitors with a moderately dorsal, hindbrain character.

Next, we sought to determine if NPBSCs remain competent for WNT and SHH mediated patterning of neural fate commitment. NPBSCs were cultured with different concentrations of CHIR and PMA alone and in combination for 6 days. qRT-PCR analysis demonstrated that dorsal neural progenitor markers MSX1 and PAX3 were upregulated by cells cultured with CHIR in a dose-dependent manner (FIG. 9A). SHH signaling opposes dorsal neural fates and specifies ventral fates (Ulloa and Briscoe, 2007). In keeping with this, NPBSCs exposed to both PMA and CHIR together expressed significantly less MSX1 and PAX3 than NPBSCs exposed to CHIR alone (FIG. 9A). In contrast, increasing the PMA 1 μM in combination with CHIR or PMA alone (without CHIR) induced upregulation of ventral neural markers NKX6-1, NKX2-1, OLIG2, and FOXA2 in a dose dependent manner (FIG. 9A). Immunostaining for FOXA2 confirmed the dose dependent specification of floor plate by PMA (FIG. 9A). GLI2 is a mediator of SHH signaling and was likewise upregulated by PMA (Bai et al., 2002). Therefore, we conclude that NPBSCs are receptive to WNT and SHH induced dorsoventral patterning of neural fate specification.

WNT signaling has been shown to induce caudal neural plate border fate in anterior neural plate, and it is significant to note that dorsal neural progenitor markers MSX1 and PAX3 are also markers of neural plate border and neural crest cells (Goulding et al., 1991; Patthey et al., 2009; Tribulo et al., 2003). As such, the upregulation of these markers by NPBSCs could also be because of assuming a neural plate border and/or neural crest identity. To test this possibility, we assessed the responsiveness of the CNS progenitor marker SOX1 to SHH and WNT signaling. We found that SOX1 expression was induced by PMA and inhibited by CHIR (FIG. 9A). The inhibition by CHIR is the same that induced MSX1 and PAX3 upregulation. These results suggest that NPBSCs are not only capable of forming different dorsoventral neural tube lineages of the CNS, but may also be capable of forming neural plate border and neural crest lineages, which include PNS neurons.

We also assessed the responsiveness of NPBSCs to repatterning signals along the rostrocaudal axis. Retinoids are produced in vivo by somites and specify spinal cord fate, which can be mimicked in vitro with all-trans retinoic acid (RA) (Novitch et al., 2003). NPBSCs treated with RA for 8 days downregulated HOXA2, and upregulated HOXA4, HOXB4, but not HOXB9 (FIG. 9B). This demonstrates that NPBSCs can be repatterned into posterior fates, including spinal cord lineages. However, despite repeated attempts, no conditions were found to be able to induce forebrain markers such as BF1. Therefore, we conclude that NPBSCs can be respecified along the rostrocaudal axis, but are unable to for forebrain lineages. Taken together, these data demonstrate that NPBSCs most closely resemble caudal neural plate border cells.

Example 4: Directed Differentiation of NPBSCs into PNS Neurons

Since PNS neurons are derived from the neural plate border region, we tested the capacity of NPBSCs to differentiate into PNS neurons. In vivo, neural plate border cells are specified by BMP proteins (Patthey et al., 2009). Since SHH, which is used to expand NPBSCs, is known to antagonize BMP induced patterning, we cultured NPBSCs in the presence of BMP4 for 8 days. To rule out possible heterogeneity within the cultures as an explanation for differentiation results, we repeated the experiments with clonal NPBSC lines derived from single NPBSCs for all subsequent experiments. Interestingly, BMP4 did not inhibit neurogenesis (FIG. 10A). Instead, immunostaining for PERIPHERIN, a marker of PNS neurons, demonstrated that the majority of the neurons were PERIPHERIN-positive, indicative of PNS neurons (FIG. 10A). Cultures of PERIPHERIN-positive neurons also stained positive for BRN3A, which is a marker of PNS sensory neurons (FIG. 10C). qRT-PCR analyses confirmed that PERIPHERIN and BRN3A were upregulated by BMP4 (FIG. 10B). As expected, 8 days of treatment with PMA essentially abolished expression of these markers (FIG. 10B). Overall, the efficiency of directing differentiation into PERIPHERIN and TUBBIII double positive cells was about 40 to 50% when three independent NPBSC lines were treated with BMP4 (FIG. 10D). Therefore, we conclude that NPBSCs are capable of forming PNS neurons, including sensory neurons.

Since PNS neurons are derived from neural crest cells, this suggests that NPBSCs are capable of forming other neural crest-derived cell types including non-neural cells. To test this, NPBSCs were differentiated using serum containing medium for 21 days after two days of treatment with CHIR alone. NPBSCs formed VIMENTIN, CD9 and SMA positive cells, which were distinctly mesenchymal in morphology (FIG. 10E). From these data, we conclude that NPBSCs are capable of forming PNS neurons as well as mesenchymal neural crest cell derivatives.

Example 5: Directed Differentiation of NPBSCs into CNS Lineages

Having established the ability to differentiate into PNS neurons, we next assessed the ability of NPBSCs to differentiate into CNS neuronal lineages. First, we exposed NPBSCs to PMA and FGF8 for 8 days, which are the patterning factors for midbrain dopaminergic (mDA) neurons (Gale and Li, 2008). After maturation for 2 weeks, immunostaining demonstrated that NPBSCs had differentiated into TH, FOXA2, and TUBBIII positive neurons, which specifically marks mDA neurons (FIGS. 11A and B). Real-time RT-PCR showed upregulation of markers of mDA differentiation, including EN-1, LMX1A, LMX1B, NURR1, FOXA2, and AADC (FIG. 11C). The overall efficiency of differentiation of mDA neurons was consistent between 3 different NPBSC lines (FIG. 11D). Taken together, these results demonstrate the formation of mDA neurons by NPBSCs using developmentally appropriate patterning signals.

SHH and RA in combination specify the formation of motor neurons (Wichterle et al., 2002). Since we had previously observed NPBSCs respond to these signals individually, we next tested the ability of SHH and RA together to direct differentiation of NPBSCs into the motor neuron lineage. Immunostaining of NPBSCs treated for 8 days with PMA and RA showed a large number of nuclei expressing OLIG2, which is a marker motor neuron progenitors (FIG. 12A). After 8 days patterning with double PMA and 1 μM RA, and maturation for 2 weeks, qRT-PCR demonstrated that markers of motor neuron differentiation including HB9, ISLET1, CHAT and HOXB4 were significantly upregulated compared to undifferentiated NPBSCs (FIG. 12B). Immunostaining showed that most TUBBIII-positive neurons were also ISLET1 and CHAT double positive, which indicates a high frequency of motor neuron formation (FIG. 12C). Immunostaining also demonstrated the presence of HB9 and TUBIII double positive cells, which is consistent with a motor neuron identity (FIG. 12D). Immunostaining of single-cell plated cells demonstrated that NPBSCs formed motor neurons with an efficiency of approximately 50% (FIG. 12E). We also tested NPBSC capacity to form astroglial cells by exposing NPBSCs to fetal calf serum for 2 weeks. Immunostaining demonstrated the abundant formation of GFAP-positive astrocytes, indicative of glial differentiation potential (FIG. 13). Therefore, we conclude that NPBSCs have the developmental potential to form CNS lineages, including mDA and motor neurons as well as glia, and PNS neurons using developmentally appropriate specification signals.

Next, we sought to determine if the ability to form both CNS and PNS neurons is retained within a single NPBSC, or if it is due to the presence of mixed heterogeneous cultures. To answer this question, we generated three clonal NPBSC lines from single hESC-derived NPBSCs. These clonal lines expressed the neural progenitor makers NES, SOX2, SOX1, and PAX6. Finally, each of these three lines could be efficiently directed to differentiate into mDA neurons, motor neurons, and PNS neurons. Therefore, we conclude that NPBSCs are clonally competent to form both CNS and PNS neurons.

Example 6: Neurons Formed From NPBSCs are Electro-Physiologically Functional

Our final objective was to evaluate the electrophysiological function of NPBSC-derived neurons using patch clamping. On average, the recorded membrane potential from NPBSC-derived neurons was −35±2 mV (n=12) and the cell membrane capacitance was 31.88±4.36 pF (n=12). These values are consistent with previously published results of neurons differentiated from human stem cells (Coyne et al., 2011; Moe et al., 2005; Westerlund et al., 2003). Stepping the membrane holding potential from −70 to +20 mV with 10 mV increment elicited a fast-activating, fast-inactivating inward current followed by a slower activating, slowly deactivating outward current (FIG. 14A). The I-V curves of both currents are typical for sodium inward current through voltage-gated sodium channels and potassium outward current through voltage gated potassium channels (FIG. 14B) described in neurons (Cummins et al., 1994; Simard et al., 1993). Current-clamp recordings demonstrated the presence of neurons that spontaneously fired action potentials (APs) with frequencies of up to 2.1 Hz (mean 1.00±0.28 Hz, n=12; FIG. 14C)—a feature common to excitable cells like neurons or muscles.

Next, we sought to determine if NPBSC-derived neurons could form functional synaptic connections using spontaneous miniature events, which has been proposed to represent the postsynaptic the postsynaptic response, evoked by releasing of neurotransmitter from a single synaptic vesicle (Del Castillo and Katz, 1954). Spontaneous activity was measured using patch-clamp method in voltage clamp whole-cell configuration at holding potential −70 mV and appeared with the frequency 0.35±0.11 Hz. The average amplitude of miniature spontaneous postsynaptic currents was 21.18±2.47 pA (peak value; n=7 cells, 360 events analyzed). Representative trace and offline analysis results are shown in FIG. 15. The offline analysis revealed that recorded minis have the amplitude or kinetic parameters comparable to those of neurons (Edwards et al., 1990; Inenaga et al., 1998; Wyllie et al., 1994), suggesting that NPBSC-derived neurons have not only acquired the electrical properties of excitable neurons, but have even developed synaptic contacts between neurons.

Example 7: Variations of the Standard Cell Culture Conditions

In order to test whether variations in the cell culture conditions affect the protocol for deriving NPBSC, several modifications of the cell culture conditions were tested. As a control, NPBSC were derived using standard conditions (each step following the other) as follows:
1. Culturing pluripotent stem cells as embryoid bodies (EBs) in pluripotent stem cell medium containing 10 μM SB-431542, 1 μM dorsomorphin, 0.5 μM purmorphamine, 3 μM CHIR-99021 for 48 hours.
2. Culturing EBs in neural medium containing 10 μM SB-431542, 1 μM dorsomorphin, 0.5 μM purmorphamine, 3 μM CHIR-99021 for 48 hours.
3. Culturing EBs in neural medium (containing B27, which contains an antioxidant) containing 0.5 μM purmorphamine, 3 μM CHIR-99021, and 150 μM ascorbic acid for 48 hours.
4. EBs were triturated, plated, and cultured in neural medium (containing B27, which contains an antioxidant) containing 0.5 μM purmorphamine, 3 μM CHIR-99021.
5. RNA samples were taken at passage 3 and expression levels were normalized to the originating pluripotent stem cells.

Different concentrations. In addition to the standard conditions, the effects of changing the concentration of individual factors were tested, as shown in FIG. 16. Specifically, the following alternatives to the standard concentrations were tested:
SB-431542 at 5 μM and 20 μM
dorsomorphin at 0.5 μM and 5 μM,
purmorphamine at 0.25 μM and 1 μM,
CHIR-99021 at 2 μM and 4 μM,
ascorbic acid at 0 μM and 500 μM.
All data are compared to undifferentiated human embryonic stem cells.

Different timing. Further, the effect of changing the duration of treatments was analysed, as shown in FIG. 17. In particular, the effects of reducing each step to 24 hours and the effects of using 96 hours for each step were tested. Also depicted are NPBSC after prolonged passaging (passage 17).

All data are compared to undifferentiated human embryonic stem cells.

Different factors. In addition to the standard compounds, the effects of replacing several factors (see FIG. 18) were tested as follows:
SB-525334 at 2 μM was used instead of SB-431542,
Noggin at 100 ng/mlwas used instead of dorsomorphin
SB-216763 at 10 μM was used instead of CHIR-99021
Smoothened Agonist (SAG) at 0.5 μM was used instead of purmorphamine.
The derivation experiments were done in duplicates, and RNA samples taken at passage 3. Also depicted are NPBSCs after prolonged passaging (passage 17).
All data are compared to undifferentiated human embryonic stem cells.

The data provided in FIGS. 16 to 18 show that the various alterations of the standard conditions tested herein with regard to the nature of the factors, their concentrations, and the timing of their addition consistently results in the derivation of NPBSCs. Adjusting the conditions to the most advantageous combination of conditions in a particular laboratory setting is thus within the skill of the skilled person.

Example 8: NPBSCs Have a Unique Expression Signature

The Illumina microarray platform was used to profile the global gene expression of NPBSCs at passage 10 (P10) and passage 20 (P20), human embryonic stem cells (HUES6), induced pluripotent stem cells (IPSCs) as well as primitive neural stem cells (pNSCs) and human neural progenitor cells (hNPCs), which were derived as described by Li et alia 2011 and Koch et alia, 2009, respectively. The heatmap demonstrates that NPBSCs express markers that are unique to these cells and distinguish NPBSCs from the other cell types previously published.

REFERENCES

Alvarez-Medina, R., Le Dreau, G., Ros, M. and Marti, E. (2009). Hedgehog activation is required upstream of Wnt signalling to control neural progenitor proliferation. Development 136, 3301-3309.

Bai, C. B., Auerbach, W., Lee, J. S., Stephen, D., and Joyner, A. L. (2002). Gli2, but not Gli1, is required for initial Shh signaling and ectopic activation of the Shh pathway. Development 129, 4753-4761.

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nat Biotechnol 27, 275-280.

Coyne, L., Shan, M., Przyborski, S. A., Hirakawa, R., and Halliwell, R. F. (2011). Neuropharmacological properties of neurons derived from human stem cells. Neurochem Int 59, 404-412.

Cummins, T. R., Xia, Y., and Haddad, G. G. (1994). Functional properties of rat and human neocortical voltage-sensitive sodium currents. J Neurophysiol 71, 1052-1064.

Del Castillo, J., and Katz, B. (1954). Quantal components of the end-plate potential. J Physiol 124, 560-573.

Edwards, F. A., Konnerth, A., and Sakmann, B. (1990). Quantal analysis of inhibitory synaptic transmission in the dentate gyrus of rat hippocampal slices: a patch-clamp study. J Physiol 430, 213-249.

Elkabetz, Y., Panagiotakos, G., Al Shamy, G., Socci, N. D., Tabar, V., and Studer, L. (2008). Human ES cell-derived neural rosettes reveal a functionally distinct early neural stem cell stage. Genes Dev 22, 152-165.

Fasano, C. A., Chambers, S. M., Lee, G., Tomishima, M. J., and Studer, L. (2010). Efficient derivation of functional floor plate tissue from human embryonic stem cells. Cell Stem Cell 6, 336-347.

Gale, E., and Li, M. (2008). Midbrain dopaminergic neuron fate specification: Of mice and embryonic stem cells. Mol Brain 1, 8.

Goulding, M. D., Chalepakis, G., Deutsch, U., Erselius, J. R., and Gruss, P. (1991). Pax-3, a novel murine DNA binding protein expressed during early neurogenesis. EMBO J 10, 1135-1147.

Hamill, OP., Marty, A., Neher, E., Sakmann, B., and Sigworth, F. J. (1981). Improved patch-clamp techniques for high-resolution current recording from cells and cell-free membrane patches. Pflugers Arch 391, 85-100.

Inenaga, K., Honda, E., Hirakawa, T., Nakamura, S., and Yamashita, H. (1998). Glutamatergic synaptic inputs to mouse supraoptic neurons in calcium-free medium in vitro. J Neuroendocrinol 10, 1-7.

Jessell, T. M. (2000). Neuronal specification in the spinal cord: inductive signals and transcriptional codes. Nat Rev Genet 1, 20-29.

Kiecker, C., and Niehrs, C. (2001). A morphogen gradient of Wnt/beta-catenin signalling regulates anteroposterior neural patterning in Xenopus. Development 128, 4189-4201.

Koch P, Opitz T, Steinbeck J A, Ladewig J, Brustle O (2009) A rosette-type, self-renewing human ES cell-derived neural stem cell with potential for in vitro instruction and synaptic integration. Proc Natl Acad Sci USA 106: 3225-3230.

Krencik, R., Weick, J. P., Liu, Y., Zhang, Z. J., and Zhang, S. C. (2011). Specification of transplantable astroglial subtypes from human pluripotent stem cells. Nat Biotechnol 29, 528-534.

Lee, K. J., and Jessell, T. M. (1999). The specification of dorsal cell fates in the vertebrate central nervous system. Annu Rev Neurosci 22, 261-294.

Li W, Sun W, Zhang Y, Wei W, Ambasudhan R, et al. (2011) Rapid induction and long-term self-renewal of primitive neural precursors from human embryonic stem cells by small molecule inhibitors. Proc Natl Acad Sci USA 108: 8299-8304.

Moe, M. C., Varghese, M., Danilov, A. I., Westerlund, U., Ramm-Pettersen, J., Brundin, L., Svensson, M., Berg-Johnsen, J., and Langmoen, I. A. (2005). Multipotent progenitor cells from the adult human brain: neurophysiological differentiation to mature neurons. Brain 128, 2189-2199.

Nordstrom, U., Jessell, T. M., and Edlund, T. (2002). Progressive induction of caudal neural character by graded Wnt signaling. Nat Neurosci 5, 525-532.

Novitch, B. G., Wichterle, H., Jessell, T. M., and Sockanathan, S. (2003). A requirement for retinoic acid-mediated transcriptional activation in ventral neural patterning and motor neuron specification. Neuron 40, 81-95.

Patthey, C., Edlund, T., and Gunhaga, L. (2009). Wnt-regulated temporal control of BMP exposure directs the choice between neural plate border and epidermal fate. Development 136, 73-83.

Patthey, C., Gunhaga, L., and Edlund, T. (2008). Early development of the central and peripheral nervous systems is coordinated by Wnt and BMP signals. PLoS One 3, e1625.

Selleck, M. A., Garcia-Castro, M. I., Artinger, K. B., and Bronner-Fraser, M. (1998). Effects of Shh and Noggin on neural crest formation demonstrate that BMP is required in the neural tube but not ectoderm. Development 125, 4919-4930.

Simard, J. M., Song, Y., Tewari, K., Dunn, S., Werrbach-Perez, K., Perez-Polo, J. R., and Eisenberg, H. M. (1993). Ionic channel currents in cultured neurons from human cortex. J Neurosci Res 34, 170-178.

Tribulo, C., Aybar, M. J., Nguyen, V. H., Mullins, M. C., and Mayor, R. (2003). Regulation of Msx genes by a Bmp gradient is essential for neural crest specification. Development 130, 6441-6452.

Ulloa, F., and Briscoe, J. (2007). Morphogens and the control of cell proliferation and patterning in the spinal cord. Cell Cycle 6, 2640-2649.

Westerlund, U., Moe, M. C., Varghese, M., Berg-Johnsen, J., Ohlsson, M., Langmoen, I. A., and Svensson, M. (2003). Stem cells from the adult human brain develop into functional neurons in culture. Exp Cell Res 289, 378-383.

Wichterle, H., Lieberam, I., Porter, J. A., and Jessell, T. M. (2002). Directed differentiation of embryonic stem cells into motor neurons. Cell 110, 385-397.

Wyllie, D. J., Manabe, T., and Nicoll, R. A. (1994). A rise in postsynaptic Ca2+ potentiates miniature excitatory postsynaptic currents and AMPA responses in hippocampal neurons. Neuron 12, 127-138.

Zhang, S. C., Wernig, M., Duncan, I. D., Brustle, O., and Thomson, J. A. (2001). In vitro differentiation of transplantable neural precursors from human embryonic stem cells. Nat Biotechnol 19, 1129-1133.

The invention claimed is:

1. A method for producing mammalian neural plate border stem cells (NPBSCs), comprising:
   (a) differentiating mammalian pluripotent stem cells by
      (a-i) culturing mammalian pluripotent stem cells in pluripotent stem cell medium for about 24 to about 96 hours, wherein the pluripotent stem cell medium comprises:
         (i) an inhibitor of the activin/TGF-β signalling pathway;
         (ii) an inhibitor of the BMP signalling pathway;
         (iii) 6-[[2-[[4-(2,4-dichlorophenyl)-5-(5-methyl-1H-imidazol-2-yl)-2-pyrimidinyl]amino]ethyl]amino]-3-pyridinecarbonitrile; and
         (iv) an activator of the Hedgehog signalling pathway; subsequently
      (a-ii) culturing the cells obtained in step (a-i) for about 24 to about 96 hours in a neural medium, wherein the neural medium comprises:
         (i) an inhibitor of the activin/TGF-β signalling pathway;
         (ii) an inhibitor of the BMP signalling pathway;
         (iii) 6-[[2-[[4-(2,4-dichlorophenyl)-5-(5-methyl-1H-imidazol-2-yl)-2-pyrimidinyl]amino]ethyl]amino]-3-pyridinecarbonitrile; and
         (iv) an activator of the Hedgehog signalling pathway; subsequently
      (a-iii) culturing the cells obtained in step (a-ii) for about 24 to about 96 hours in a neural medium, wherein the neural medium comprises:
         (i) 6-[[2-[[4-(2,4-dichlorophenyl)-5-(5-methyl-1H-imidazol-2-yl)-2-pyrimidinyl]amino]ethyl]amino]-3-pyridinecarbonitrile;
         (ii) an activator of the Hedgehog signalling pathway; and
         (iii) an inhibitor of oxidation;
   (b) plating the obtained differentiated mammalian pluripotent stem cells in NPBSCs expansion medium, wherein the NPBSCs expansion medium comprises
      (i) 6-[[2-[[4-(2,4-dichlorophenyl)-5-(5-methyl-1H-imidazol-2-yl)-2-pyrimidinyl]amino]ethyl]amino]-3-pyridinecarbonitrile;
      (ii) an activator of the Hedgehog signalling pathway; and
      (iii) an inhibitor of oxidation;
      and expanding the cells in the NPBSCs expansion medium for about 24 to about 96 hours;
   (c) splitting the cells obtained in (b) and further expanding the cells in the NPBSCs expansion medium; and
   (d) repeating step (c) at least two times; thereby obtaining cells that
      (1) express SOX1, MSX1 and PHOX2B and do not express NKX6.1 and VCAM-1; or
      (2) express SOX2, IRX3, and MSX1 and do not express HOXB8, HOXA5 and VCAM-1;
   wherein expression of SOX1, MSX1, PHOX2B, NKX6.1, VICAM-1, SOX2, IRX3, HOXB8 and HOXA5 is determined by detecting mRNA.

2. The method of claim 1, wherein the differentiated mammalian pluripotent stem cells are plated in step (b) at a density of about 1000 to 100,000 per cm².

3. The method of claim 1, wherein the obtained NPBSCs express at least one additional marker selected from the group consisting of FORSE1, PAX3, PAX6, NESTIN, HOXA2, HOXB2, HES5, DACH1, PLZF, LMO3, EVI1 and ASCL1, wherein expression is determined by detecting mRNA.

4. The method of claim 1, wherein the obtained NPBSCs do not express at least one of the markers selected from the group consisting of OCT4, NANOG, AFP, T, SOX17, EOMES, GSH2, OLIG2, CK8, CK18, NKX2.2, and FOXA2, wherein expression is determined by detecting mRNA.

5. The method of claim 1, further comprising:
   (e) culturing the NPBSCs obtained in step (d) in a neural medium comprising 6-[[2-[[4-(2,4-dichlorophenyl)-5-(5-methyl-1H-imidazol-2-yl)-2-pyrimidinyl]amino]ethyl]amino]-3-pyridinecarbonitrile for about 48 to 72 hours;
   (f) adding an activator of the BMP pathway to the culture of step (e) for about 192 hours; and
   (g) culturing the cells obtained in step (f) for about 336 hours in a neural medium containing at least two different neurotrophins and an inhibitor of oxidation;
   thereby differentiating the NPBSCs into peripheral nervous system neurons.

6. The method of claim 1, further comprising:
   (e) culturing the NPBSCs obtained in step (d) in a neural medium;
   thereby differentiating the NPBSCs into central nervous system neurons.

7. The method of claim 1, further comprising:
   (e) culturing the NPBSCs obtained in step (d) in a neural medium comprising
      (e-i) an activator of the FGF signaling pathway,
      (e-ii) an activator of the hedgehog signaling pathway and
      (e-iii) an inhibitor of oxidation,
   for about 168 to about 192 hours;
   (f) changing the medium to a neural medium comprising
      (f-i) at least two different neurotrophins,
      (f-ii) an inhibitor of oxidation;
      and culturing the cells for about 24 to about 96 hours; and
   (g) further culturing the cells in a neural medium comprising
      (g-i) at least two different neurotrophins; and
      (g-ii) an inhibitor of oxidation;
   thereby differentiating the NPBSCs into midbrain dopaminergic neurons.

8. The method of claim 1, further comprising:
   (e) culturing the NPBSCs obtained in step (d) in a neural medium comprising an activator of the hedgehog signaling pathway for about 24 to about 48 hours;
   (f) adding retinoic acid to the culture of step (e) for about 168 to about 192 hours; and
   (g) further culturing the cells in a neural medium comprising at least two different neurotrophins,
   thereby differentiating the NPBSCs into motor neurons.

9. The method of claim 1, further comprising:
   (e) culturing the NPBSCs obtained in step (d) in a neural medium comprising 6-[[2-[[4-(2,4-dichlorophenyl)-5-(5-methyl-1H-imidazol-2-yl)-2-pyrimidinyl]amino]ethyl]amino]-3-pyridinecarbonitrile for about 48 to 72 hours; and
   (f) culturing the cells obtained in step (e) in a cell culture medium comprising serum, thereby differentiating the NPBSCs into neural crest-derived mesenchymal cells.

10. The method of claim 1, further comprising:
    (e) culturing the NPBSCs obtained in step (d) in a cell culture medium comprising an activator of FGF signalling for about 12 to 96 hours; and
    (f) culturing the cells obtained in step (e) in a cell culture medium comprising fetal calf serum, fetal bovine serum and/or CNTF for about 14 to 60 days;
    thereby differentiating the NPBSCs into astrocytes.

11. The method of claim 1, further comprising:
(e) culturing the NPBSCs obtained in step (d) in a neural medium comprising an activator of FGF signalling for about 12 to 96 hours;
thereby differentiating the NPBSCs into neural rosette cells.

12. The method of claim 1, in which the medium used in steps a-i to a-iii is substantially free of FGF2.

* * * * *